US010383939B2

(12) United States Patent
Nagpal et al.

(10) Patent No.: US 10,383,939 B2
(45) Date of Patent: Aug. 20, 2019

(54) LIGHT-ACTIVATED COMPOSITIONS AND METHODS USING THE SAME

(71) Applicant: THE REGENTS OF THE UNIVERSITY OF COLORADO, A BODY CORPORATE, Denver, CO (US)

(72) Inventors: Prashant Nagpal, Lafayette, CO (US); Anushree Chatterjee, Lafayette, CO (US); Colleen Courtney, Boulder, CO (US); Samuel Martin Goodman, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 15/559,577

(22) PCT Filed: Mar. 18, 2016

(86) PCT No.: PCT/US2016/023191
§ 371 (c)(1),
(2) Date: Sep. 19, 2017

(87) PCT Pub. No.: WO2016/154023
PCT Pub. Date: Sep. 29, 2016

(65) Prior Publication Data
US 2018/0043022 A1    Feb. 15, 2018

Related U.S. Application Data

(60) Provisional application No. 62/136,128, filed on Mar. 20, 2015.

(51) Int. Cl.
*A61K 41/00* (2006.01)
*A61K 9/51* (2006.01)
(Continued)

(52) U.S. Cl.
CPC ........ *A61K 41/0057* (2013.01); *A61K 9/5115* (2013.01); *A61K 31/16* (2013.01);
(Continued)

(58) Field of Classification Search
CPC ....... A61K 41/0057; A61N 5/062; B82Y 5/00
See application file for complete search history.

(56) References Cited

U.S. PATENT DOCUMENTS

2002/0127224 A1    9/2002   Chen et al.
2008/0248001 A1   10/2008   Bourke
(Continued)

OTHER PUBLICATIONS

Jin, Antimicrobial Efficacy of Zinc Oxide Quantum Dots Against Listeria Monocytogenes, *Salmonella enteritidis*, and s*Echerichia coli* 0157:H7*, Journal of Food Science, 2009, vol. 79, No. 1.*
(Continued)

*Primary Examiner* — Carlos A Azpuru
(74) *Attorney, Agent, or Firm* — Saul Ewing Arnstein & Lehr LLP; Kathryn Doyle; Domingos J. Silva

(57) ABSTRACT

The invention includes light-activated compositions and methods that are useful for promoting cell death or growth. In certain embodiments, the compositions comprise quantum dots (QD).

14 Claims, 44 Drawing Sheets

(51) Int. Cl.
*A61K 31/16* (2006.01)
*A61K 31/496* (2006.01)
*A61K 31/546* (2006.01)
*A61K 31/7036* (2006.01)
*A61K 31/7056* (2006.01)
*A61K 35/74* (2015.01)
*A61N 5/06* (2006.01)
*H01L 29/22* (2006.01)
*H01L 29/26* (2006.01)
*B82Y 5/00* (2011.01)
*H01L 29/06* (2006.01)
*H01L 29/225* (2006.01)

(52) U.S. Cl.
CPC .......... *A61K 31/496* (2013.01); *A61K 31/546* (2013.01); *A61K 31/7036* (2013.01); *A61K 31/7056* (2013.01); *A61K 35/74* (2013.01); *A61N 5/062* (2013.01); *H01L 29/22* (2013.01); *H01L 29/2203* (2013.01); *H01L 29/26* (2013.01); *A61N 2005/0661* (2013.01); *A61N 2005/0662* (2013.01); *B82Y 5/00* (2013.01); *H01L 29/0665* (2013.01); *H01L 29/225* (2013.01); *Y02A 50/473* (2018.01)

(56) References Cited

U.S. PATENT DOCUMENTS

2011/0218140 A1 9/2011 Gonsalves et al.
2012/0127224 A1* 5/2012 Martin ............... H04N 1/00188
347/9
2012/0267234 A1 10/2012 Reece et al.
2014/0242676 A1 8/2014 Abdel-Fattah et al.

OTHER PUBLICATIONS

He, et al., "Photogenerated Charge Carriers and Reactive Oxygen Species in ZnO/Au Hybrid Nanostructures with Enhanced Photocatalytic and Antibacterial Activity", J Am Chem Soc, vol. 136, 2014, pp. 750-757.

Jin, et al., "Antimicrobial Efficacy of Zinc Oxide Quantum Dots Against Listeria monocytogenes, *Salmonella enteritidis*, and *Escherichia coli* O157:H7", J Food Sci, vol. 74, No. 1, 2009, pp. M46-M52.

Kairyte, et al., "Antibacterial and Antifungal Activity of Photoactivated ZnO Nanoparticles in Suspension", J Photochem and Photobiol B: Biology, vol. 128, 2013, pp. 78-84.

Li, et al., "Mechanism of Photogenerated Reactive Oxygen Species and Correlation with the Antibacterial Properties of Engineered Metal-Oxide Nanoparticles", ACS Nano, vol. 6, No. 6, 2012, pp. 5164-5173.

Lu, et al., "Mechanism of Antimicrobial Activity of CdTe Quantum Dots", Langmuir, vol. 24, No. 10, 2008, pp. 5445-5452.

PCT International Search Report and Written Opinion dated Jun. 9, 2016 for International Application No. PCT/US2016/023191.

* cited by examiner

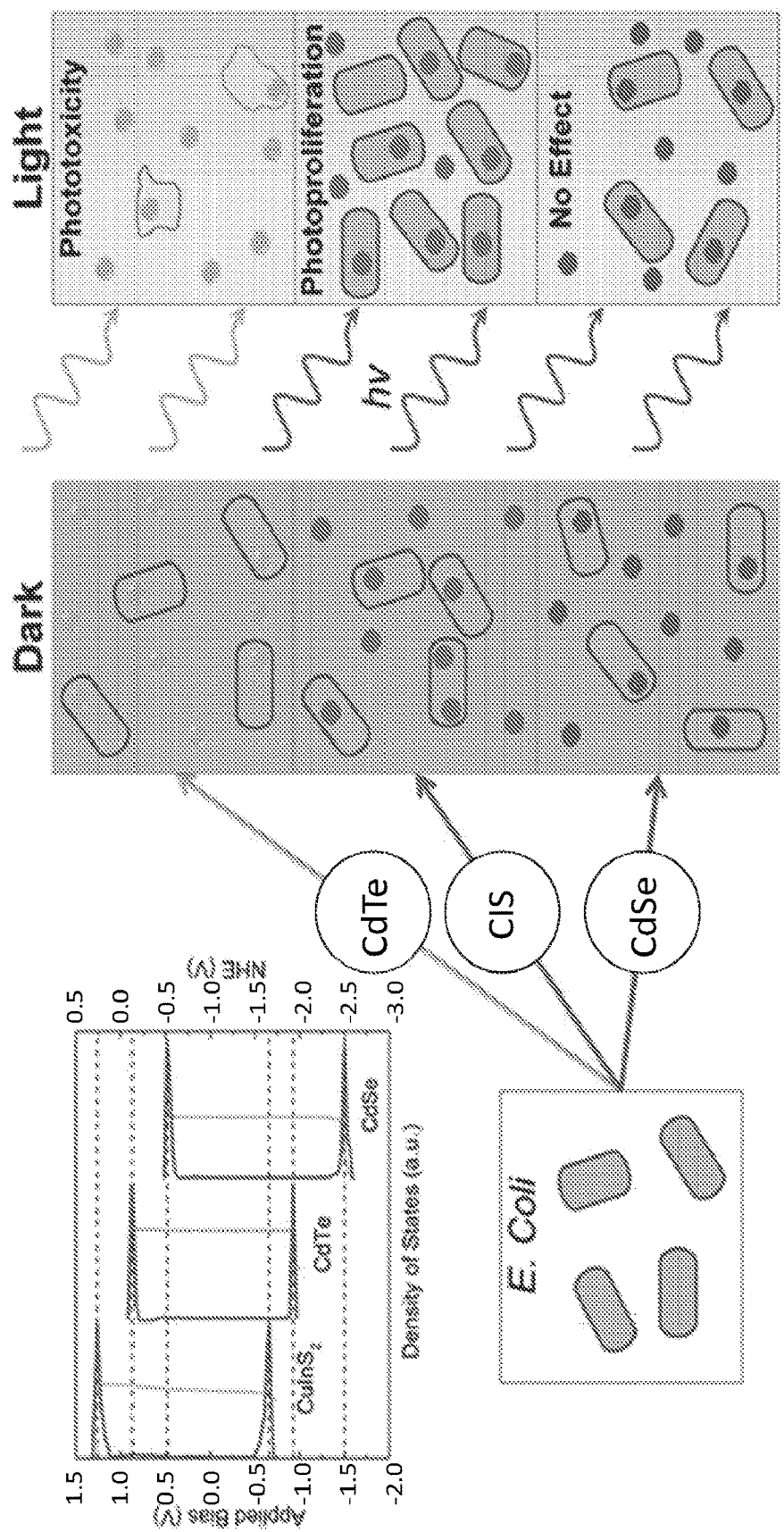

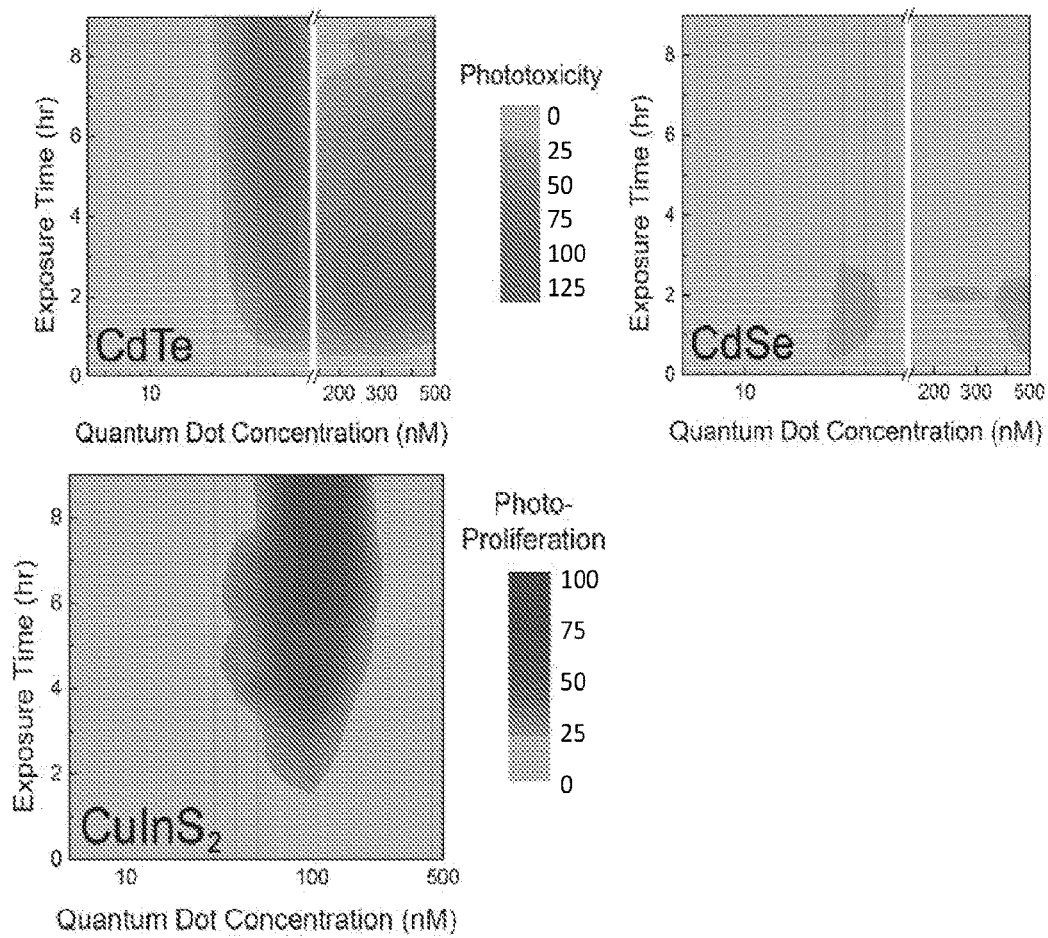

Fig. 12
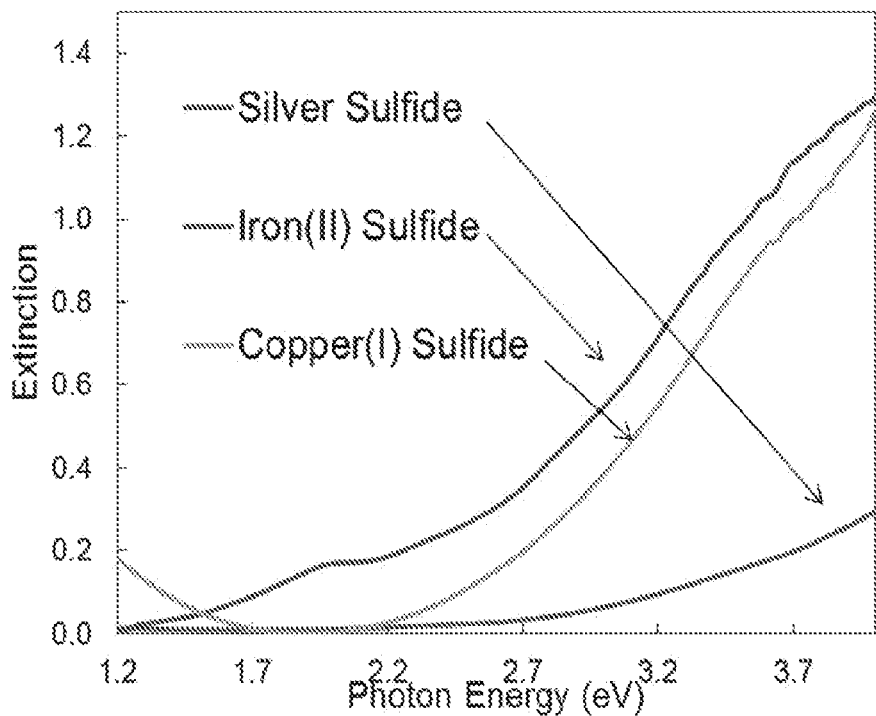
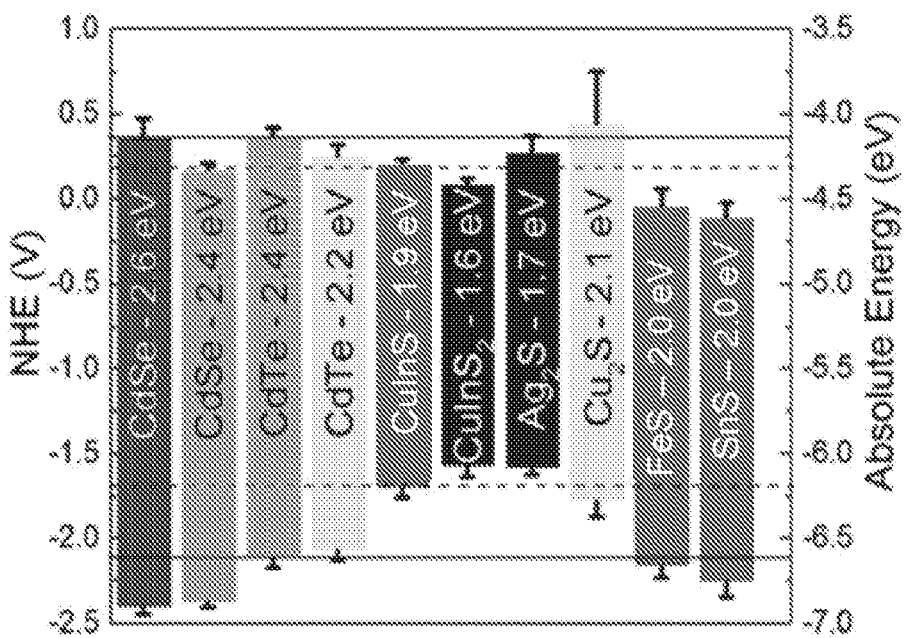

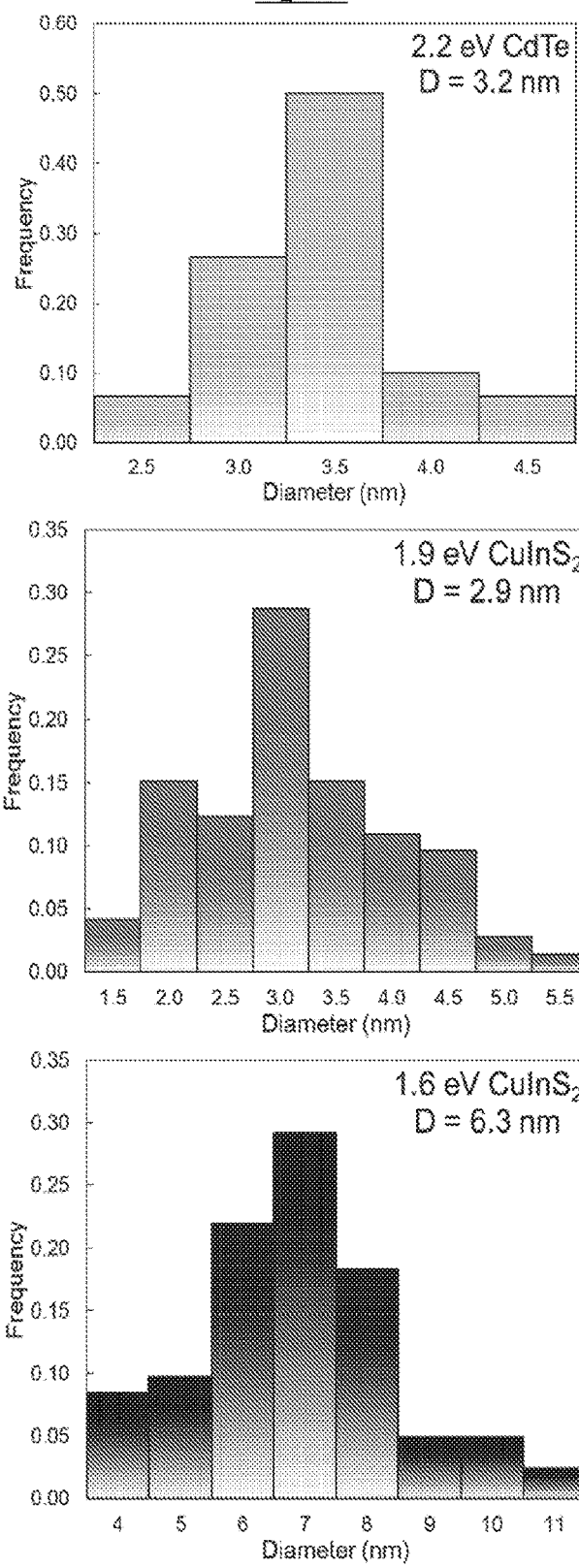

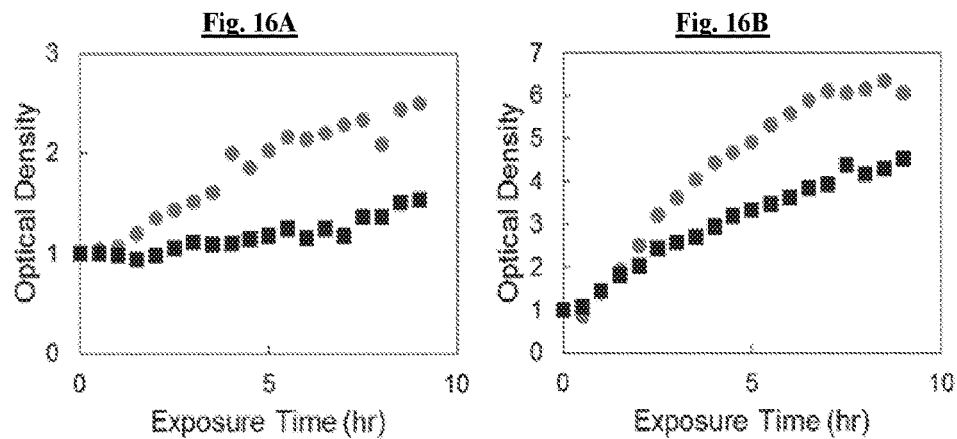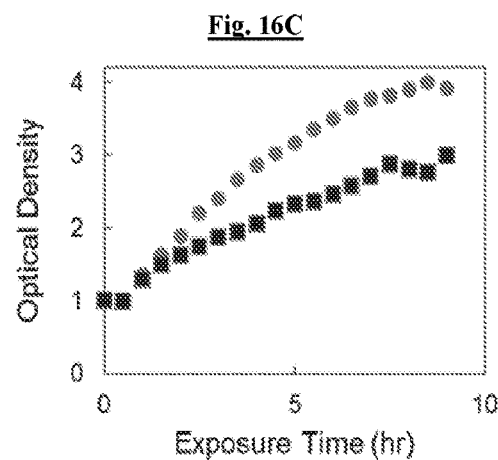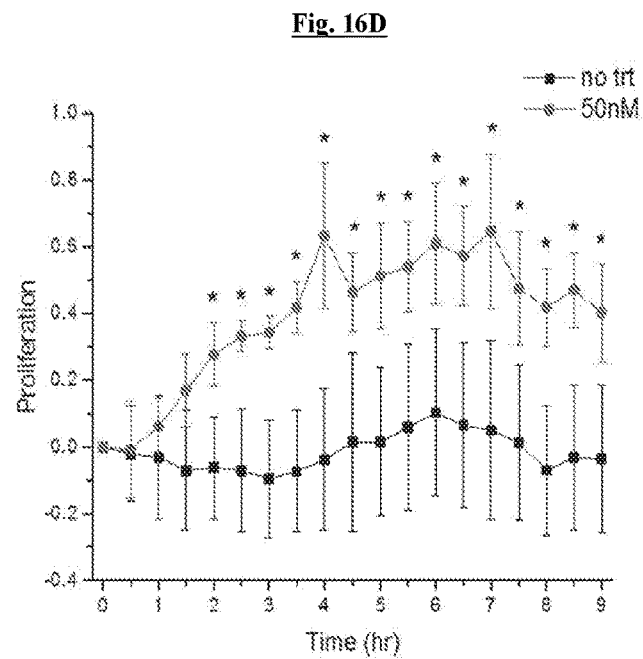

a　　　　　b　　　　　c　　　　　d

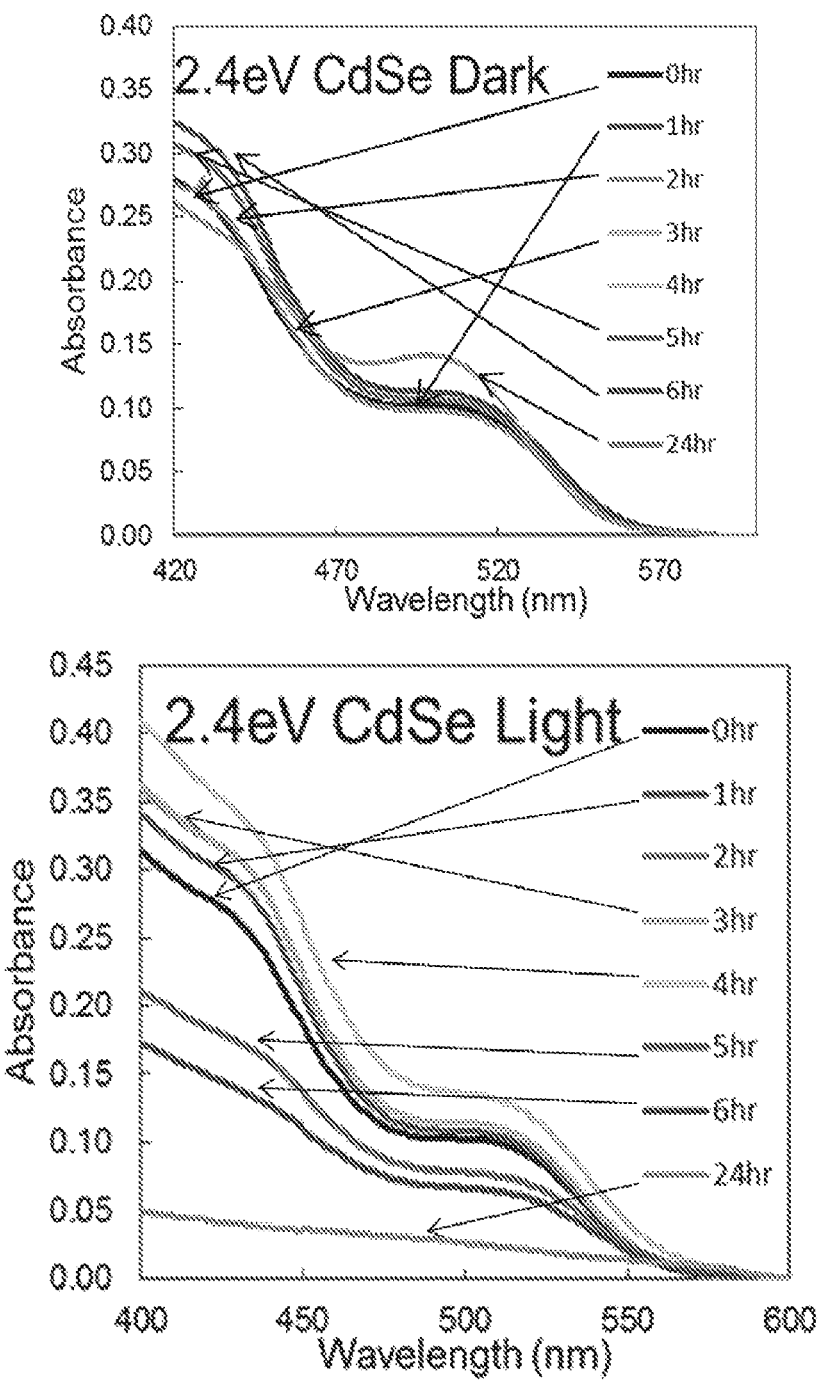

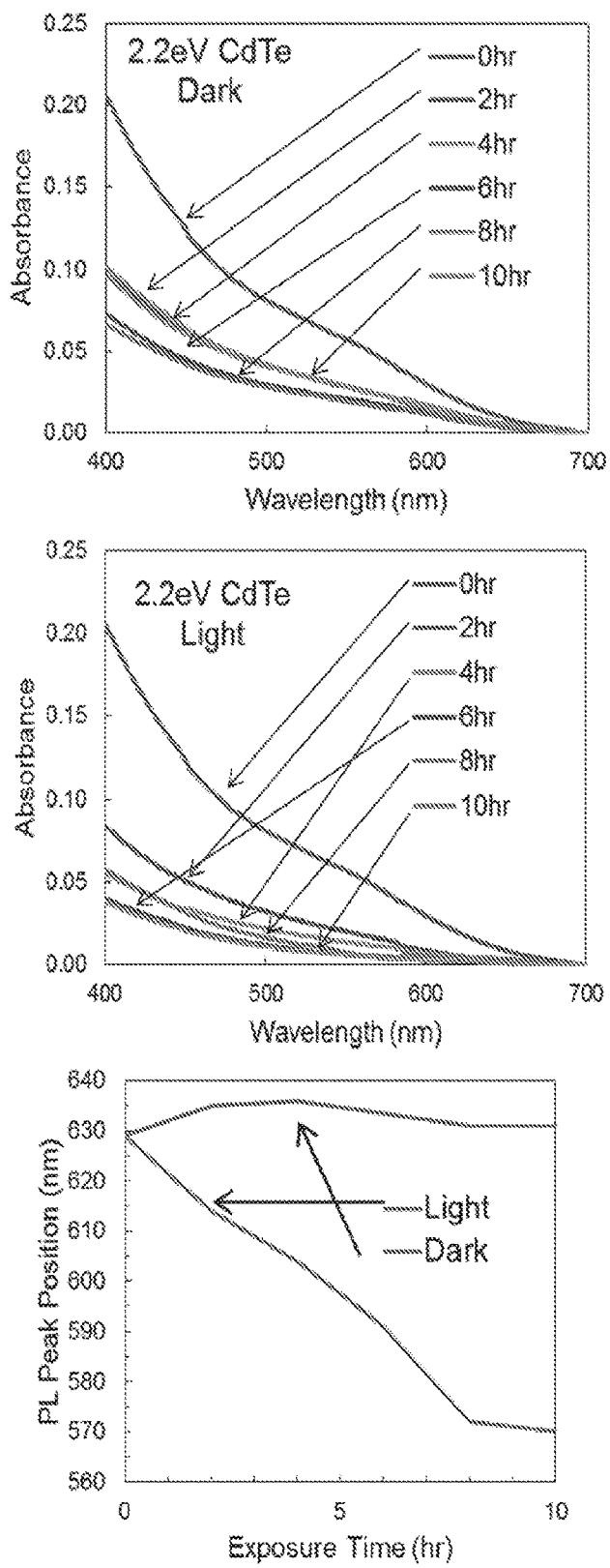

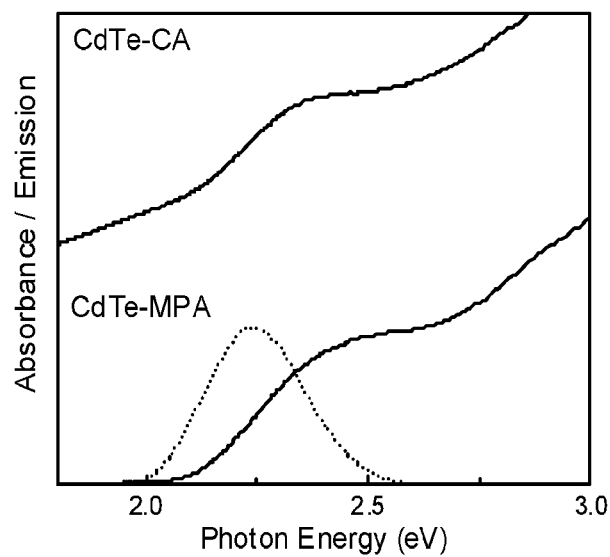
Fig. 23A
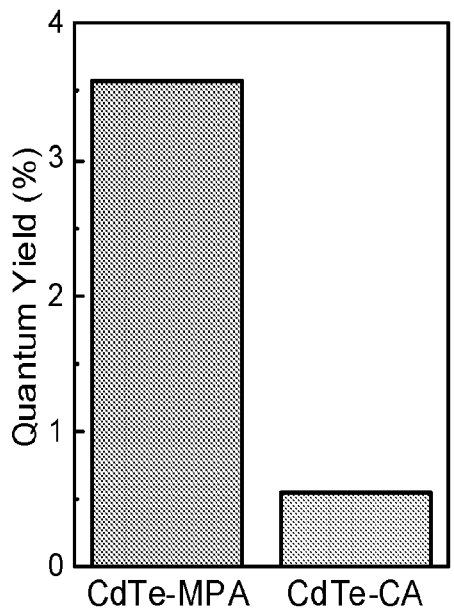

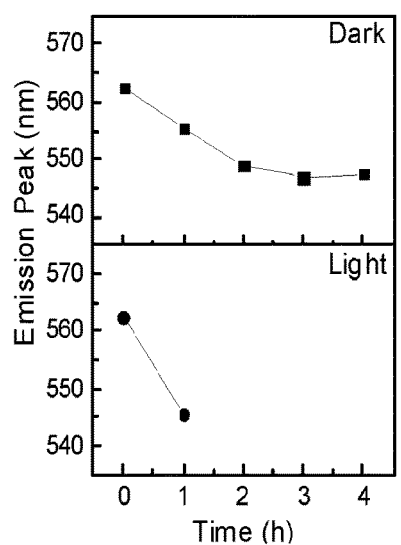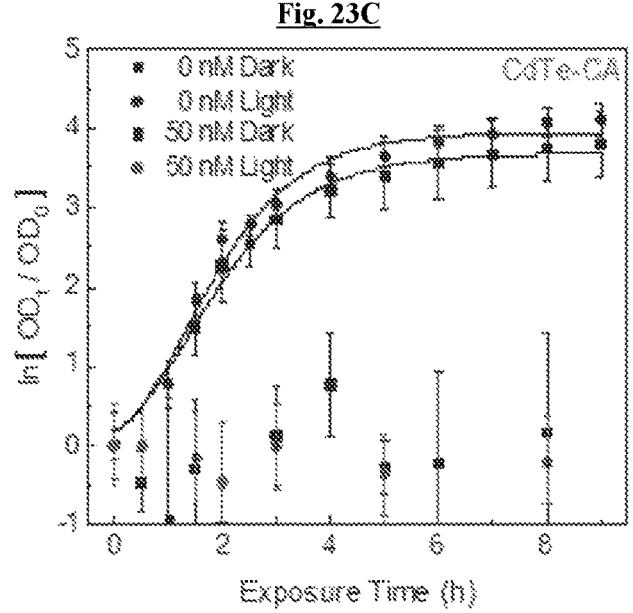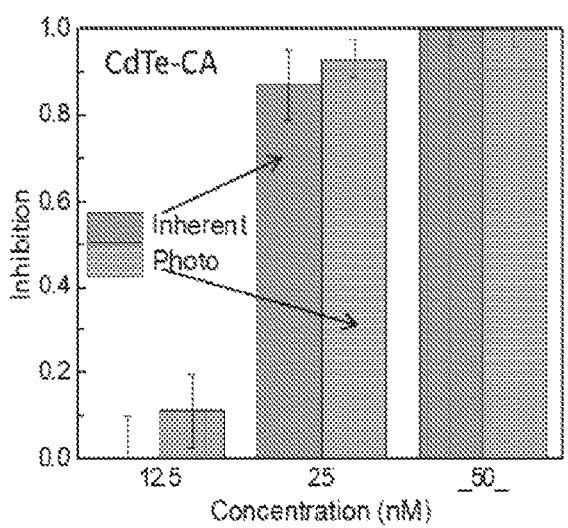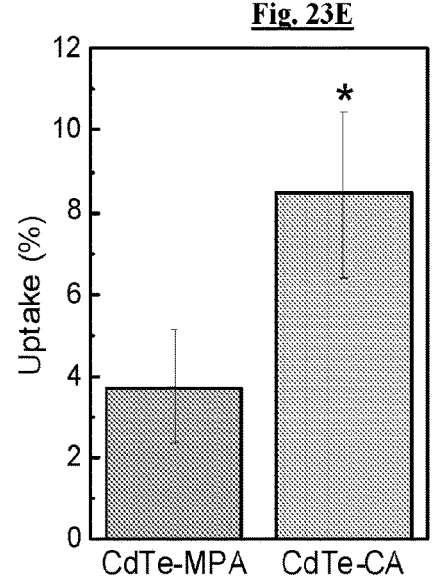

Fig. 24A
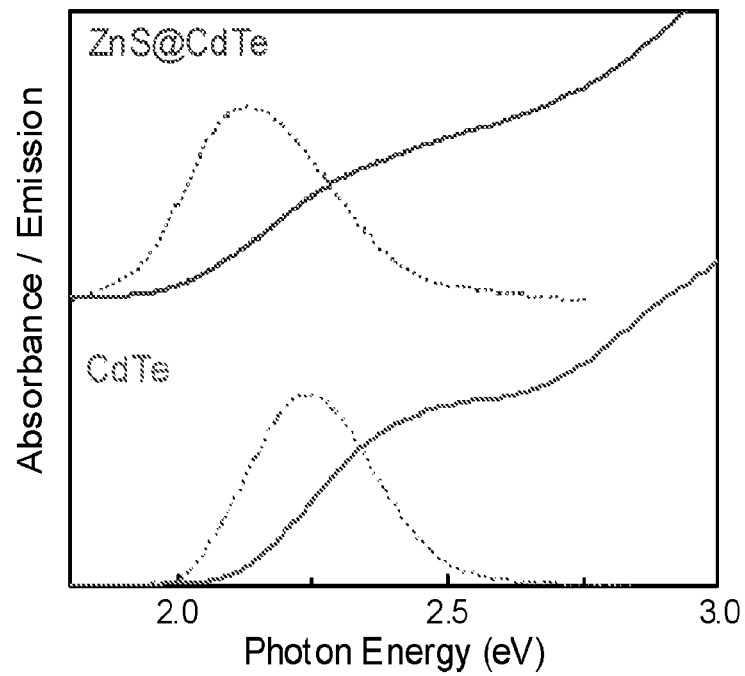
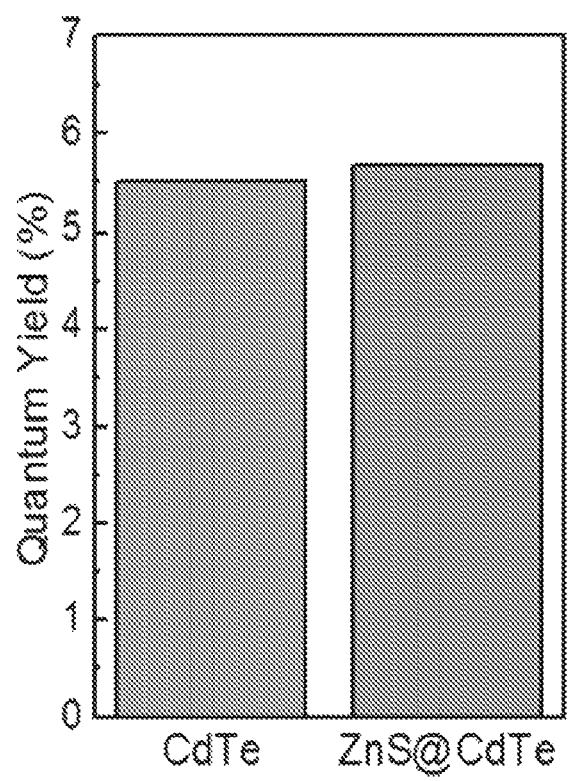

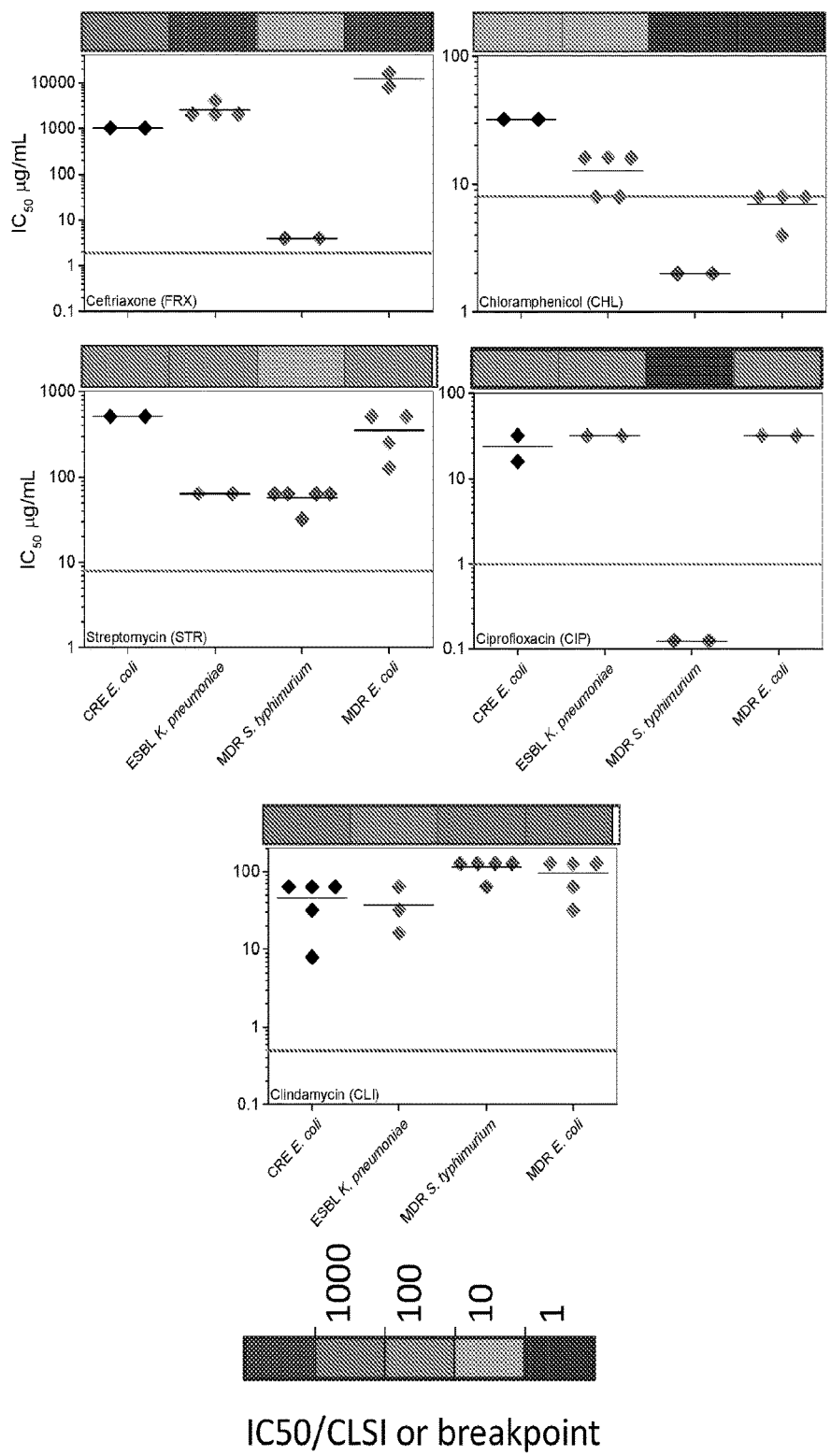

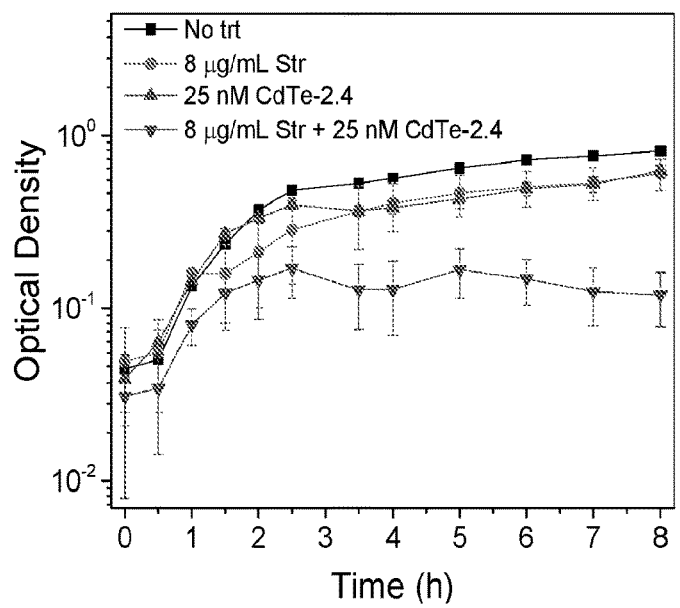
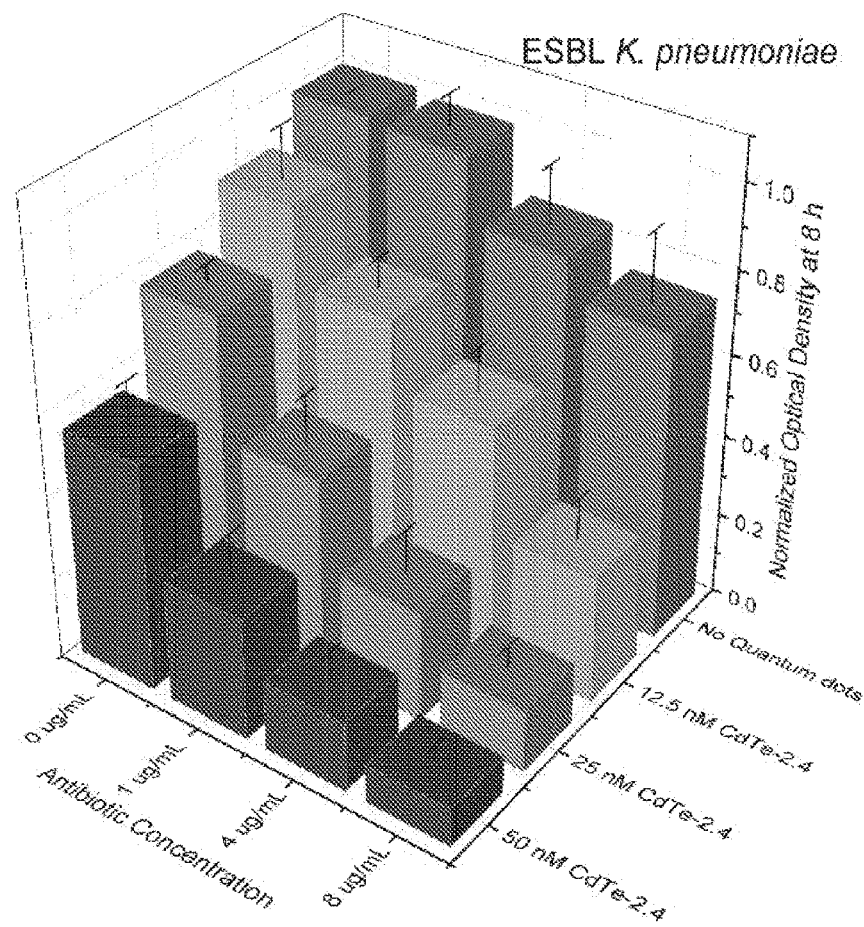
Fig. 27C

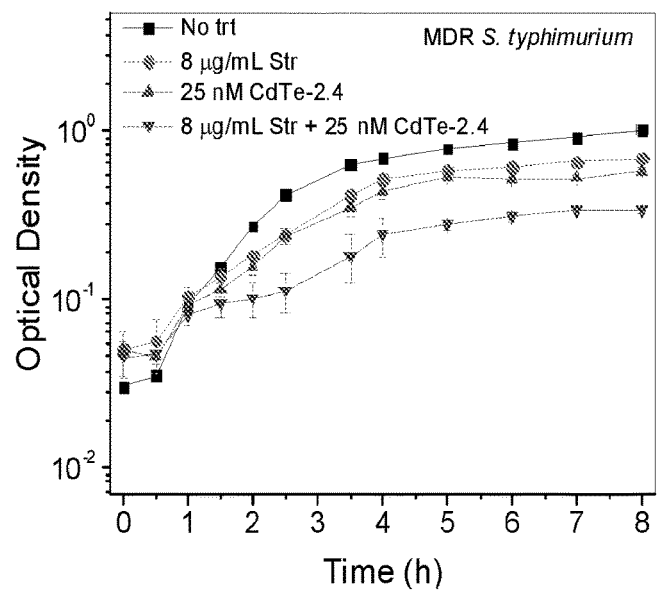
Fig. 27D
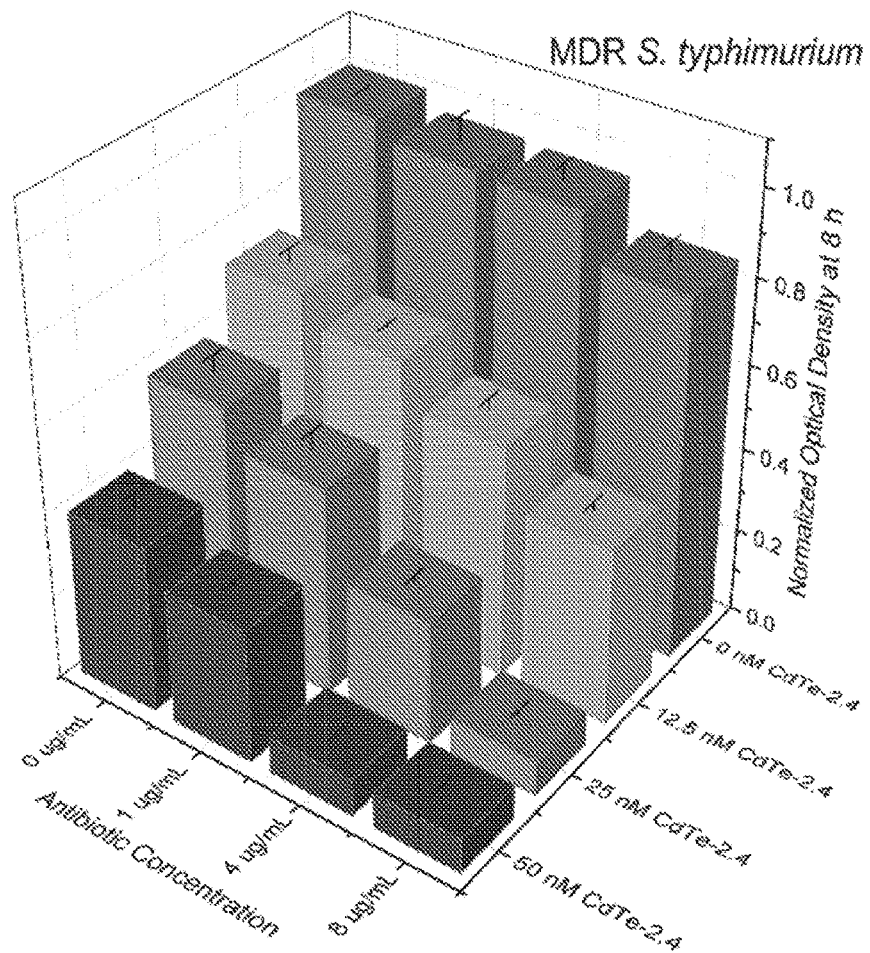

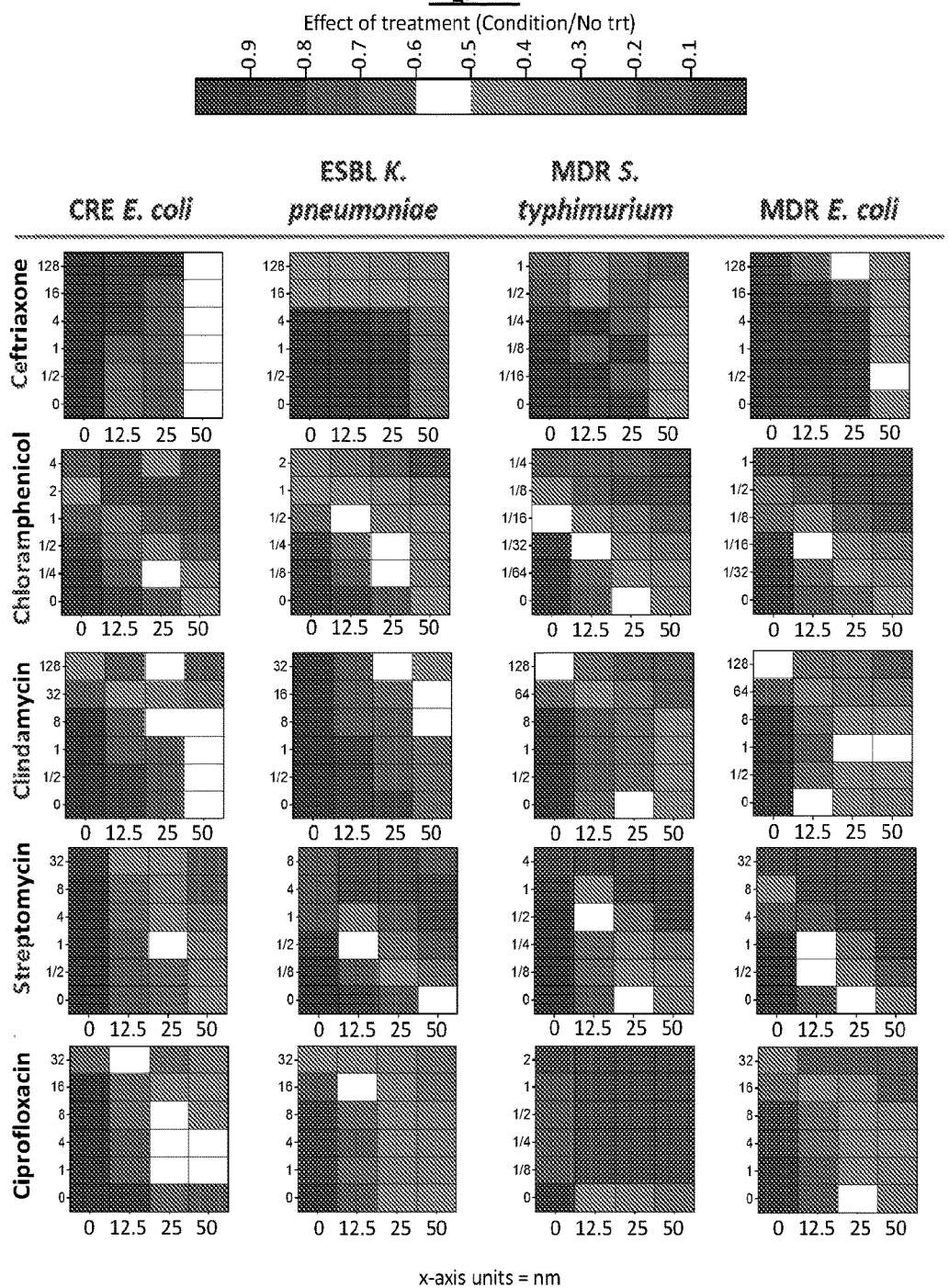

LIGHT-ACTIVATED COMPOSITIONS AND METHODS USING THE SAME

CROSS-REFERENCE TO RELATED APPLICATIONS

The present application is a 35 U.S.C. § 371 national phase application of, and claims priority to, International Application No. PCT/US2016/023191, filed Mar. 18, 2016, which claims priority under 35 U.S.C. § 119(e) to U.S. Provisional Application No. 62/136,128, filed Mar. 20, 2015, all of which applications are incorporated herein by reference in their entireties.

BACKGROUND OF THE INVENTION

The small size and tunability of nanomaterials has engendered great interest in biological applications such as diagnostics and therapeutics. Silver and metal oxide nanoparticles show bactericidal effects in a range of microorganisms. Metal nanoparticles may act as infrared absorbers and induce cell death by heating the surrounding medium. This toxic effect is generally attributed to the generation of generic reactive oxidative species (ROS) and free radicals, which can damage biomolecules such as DNA, RNA and proteins.

Cells that grow in aerobic environments have mechanisms to mitigate or use ROS through redox homeostasis processes. Within cell types, a specific redox homeostasis is maintained by the cell, and this governs the function of broad processes including metabolism and signal transduction. The generation of the specific ROS species is determined by the redox environment present in the cell. Perturbation outside of a cells redox homeostasis is linked to cell death in *Escherichia coli*, cancer, cardiovascular disease, and ageing in humans, and irreversible tissue damage in plants.

Quantum dots (QDs) are nanoparticles made of semiconductor materials and small enough to exhibit quantum mechanical properties. Specifically, the QD's excitons are confined in all three spatial dimensions. Due to quantum confinement, QDs have quantized energy states that, when photo-excited, have excited electrons and holes available for interactions.

The electronic properties of QDs are intermediate between those of bulk semiconductors and of discrete molecules. Electronic characteristics of a QD are closely related to its size and shape. For example, the band gap in a QD, which determines the frequency range of emitted light, is inversely related to its size. In fluorescent dye applications, the frequency of emitted light increases as the size of the QD decreases. Consequently, the color of emitted light shifts from red to blue when the size of the quantum dot is made smaller. This allows the excitation and emission of QD to be highly tunable. Since the size of a QD may be set when it is made, its conductive properties may be carefully tuned and/or controlled. QD dot assemblies consisting of many different sizes, such as gradient multi-layer nanofilms, can thus exhibit a range of desirable emission properties.

There is a need in the art for novel compositions that can be used to promote growth and/or death of cells. In certain embodiments, the compositions promote selective growth and/or death of a cell type in the presence of another cell type. The present invention meets this need.

BRIEF SUMMARY OF THE INVENTION

The present invention provides a composition comprising at least one semiconductor-containing nanoparticle. The present invention further provides a method of promoting growth, killing, or preventing and/or hampering growth, of a first cell. The present invention further provides a method of altering redox homeostasis in a cell.

In certain embodiments, the at least one nanoparticle has a band edge redox potential such that, under conditions whereby the at least one nanoparticle penetrates a first cell, irradiation of the composition with radiation ranging from about 400 nm to about 1,000 nm in the presence of the first cell promotes growth, kills, or prevents and/or hampers growth, of the first cell.

In certain embodiments, the at least one nanoparticle comprises a quantum dot (QD).

In certain embodiments, the composition is irradiated with radiation ranging from about 750 nm to about 1,000 nm.

In certain embodiments, the at least one nanoparticle comprises CdTe, and wherein the at least one nanoparticle is at least partially coated with at least one selected from the group consisting of ZnS and CdS.

In certain embodiments, the composition further comprises the first cell. In other embodiments, the first cell is a bacterium. In yet other embodiments, the bacterium comprises at least one selected from the group consisting of *K. pneumonia, E. coli, S. aureus, P. aeruginosa, A. baumannii* and *S. typhimurium*. In yet other embodiments, the first cell comprises a gram-negative bacterium. In yet other embodiments, the first cell comprises a multi-drug resistant gram-negative bacterium. In yet other embodiments, the composition further comprises at least one gram-negative antibacterial agent. In yet other embodiments, the at least one antibacterial agent is a cephalosporin antibiotic, fluoroquinone, or protein synthesis inhibitor. In yet other embodiments, the at least one antibacterial agent is selected from the group consisting of Amikacin, Aztreonam, Cefdinir, Cefaclor, Cefamandole, Cefditoren, Cefixime, Cefoperazone, Cefotaxime, Cefoxitin, Cefpodoxime, Cefprozil, Cefuroxime, Ceftazidime, Ceftibuten, Ceftobiprole, Ceftriaxone, Chloramphenicol, Ciprofloxacin, Clindamycin, Colistin, Ertapenem, Doripenem, Gatifloxacin, Gentamicin, Imipenem/Cilastatin, Kanamycin, Levofloxacin, Meropenem, Metronidazole, Moxifloxacin, Neomycin, Netilmicin, Ofloxacin, Paromomycin, Polymyxin B, Streptomycin, Thiamphenicol, Tigecycline, and Tobramycin.

In certain embodiments, the concentration or amount of the antibacterial agent in the composition that is required to kill, or prevent and/or hamper the growth of, gram-negative bacteria is lower than the concentration or amount of the antibacterial agent that is required to kill, or prevent and/or hamper the growth of, gram-negative bacteria when the antibacterial agent is used in the absence of the at least one nanoparticle.

In certain embodiments, the composition further comprises a second cell, wherein irradiation of the composition has no measurable effect on the growth, metabolism and/or survival of the second cell. In other embodiments, the second cell is mammalian.

In certain embodiments, irradiation of the composition in the presence of the first cell promotes growth of the first cell, and wherein the QD comprises $CuInS_2$.

In certain embodiments, irradiation of the composition in the presence of the first cell kills, or prevents and/or hampers growth of, the first cell, and wherein the QD comprises CdTe.

In certain embodiments, irradiation of the composition in the presence of the first cell promotes growth of the first cell, and wherein the band edge of the conduction band state (reduction potential) of the QD is about +0.2 V and the band edge of the valence band state (oxidation potential) of the QD is about −1.8 V, as referenced to NHE (standard hydrogen electrode).

In certain embodiments, irradiation of the composition in the presence of the first cell promotes death or prevents and/or hampers growth of the first cell, and wherein the band edge of the conduction band state (reduction potential) of the QD is about +0.35 V and the band edge of the valence band state (oxidation potential) of the QD is about −2.1 V, as referenced to NHE (standard hydrogen electrode).

In certain embodiments, irradiation of the composition has at least one effect selected from the group consisting of: changing redox homeostasis in the first cell, and generating at least one light-activated reactive species in the first cell.

In certain embodiments, the method comprises irradiating the first cell with radiation ranging from about 400 nm to about 1,000 nm in the presence of at least one semiconductor-containing nanoparticle with a band edge redox potential, under conditions whereby the at least one nanoparticle penetrates the first cell. In other embodiments, the first cell comprises a gram-negative bacterium and wherein the first cell is further contacted with at least one gram-negative antibacterial agent.

In certain embodiments, the first cell is in the presence of a second cell, and wherein irradiation of the first and second cells in the presence of the at least one nanoparticle has no measurable effect on the growth, metabolism and/or survival of the second cell. In yet other embodiments, the second cell is mammalian. In yet other embodiments, growth of the first cell is promoted, and wherein the QD comprises $CuInS_2$. In yet other embodiments, growth of the first cell is prevented and/hampered, or killing of the first cell is promoted, and wherein the QD comprises CdTe. In yet other embodiments, growth of the first cell is promoted, and wherein the band edge of the conduction band state (reduction potential) of the QD is about +0.2 V and the band edge of the valence band state (oxidation potential) of the QD is about −1.8 V, as referenced to NHE (standard hydrogen electrode). In yet other embodiments, growth of the first cell is prevented and/or hampered, or killing of the first cell is promoted, and wherein the band edge of the conduction band state (reduction potential) of the QD is about +0.35 V and the band edge of the valence band state (oxidation potential) of the QD is about −2.1 V, as referenced to NHE (standard hydrogen electrode). In yet other embodiments, the at least one nanoparticle comprises CdTe, and wherein the at least one nanoparticle is at least partially coated with at least one selected from the group consisting of ZnS and CdS. In yet other embodiments, irradiation has at least one effect selected from the group consisting of: changing redox homeostasis in the first cell, and generating at least one light-activated reactive species in the first cell.

BRIEF DESCRIPTION OF THE FIGURES

For the purpose of illustrating the invention, there are depicted in the drawings certain embodiments of the invention. However, the invention is not limited to the precise arrangements and instrumentalities of the embodiments depicted in the drawings.

FIG. 1A illustrates STS measurements of cadmium selenide (CdSe), cadmium telluride (CdTe), and copper indium sulfide ($CuInS_2$, CIS) nanoparticles with bandgaps of ~1.9 eV, demonstrating the different redox potentials of the materials. FIG. 1B is a schematic illustration of the impact on cells from exposure to quantum dots. Below a concentration threshold, the quantum dots had no effect on cell health in dark. Upon light exposure, the formation of light-activated reactive species (LARS) led to phototoxicity for CdTe, photo-proliferation (enhanced growth) for CIS, and no effect for CdSe.

FIG. 3B comprises a series of photoeffect contour plots of cell response to QDs as a function of QD concentration and light exposure duration. CdTe-2.4 and CdSe-2.4 were plotted in units of toxicity, while CIS-1.9 was plotted in units of proliferation. Grey color indicates a response was within the error threshold of the measurement ($p>0.05$).

Figure 11:
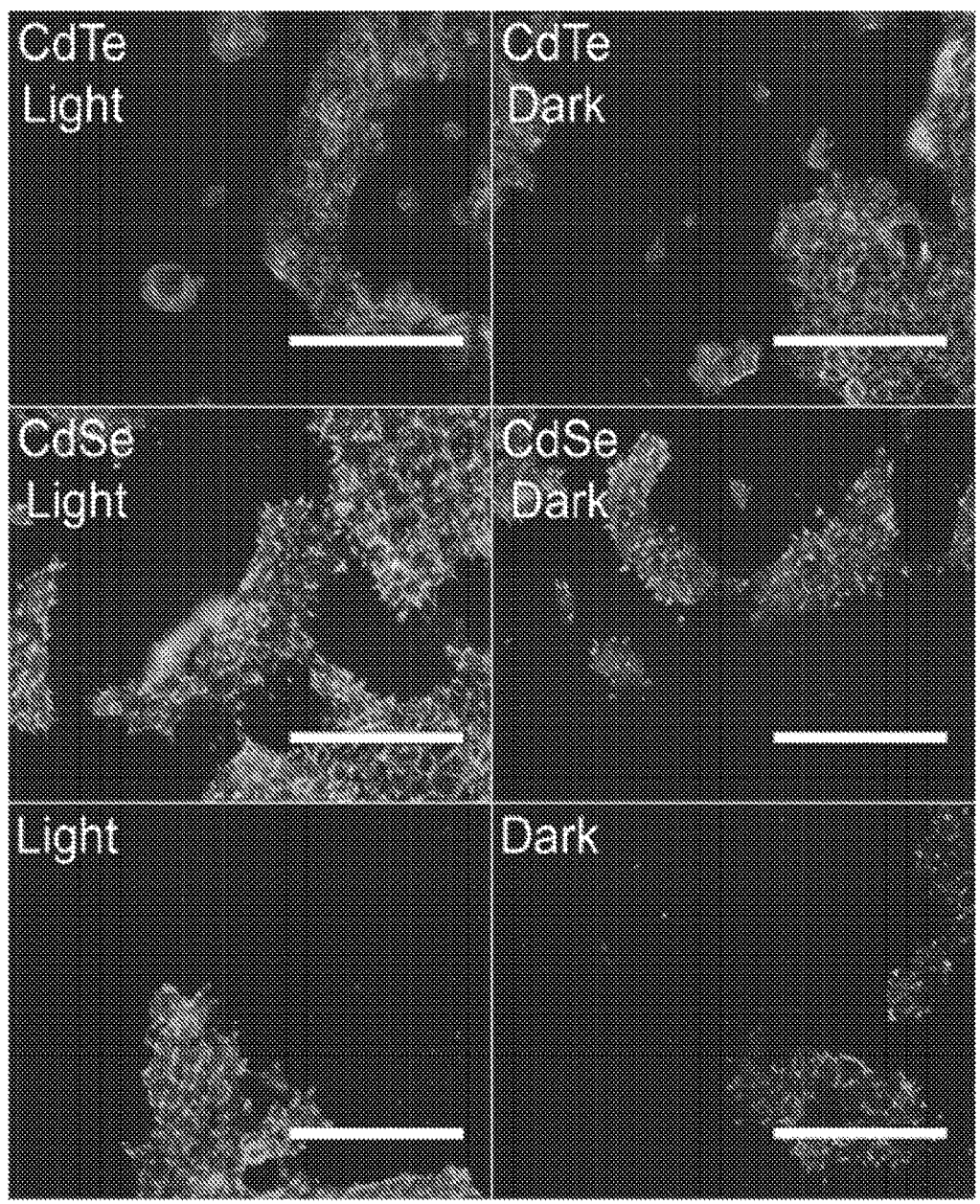

FIG. 11 comprises a series of fluorescence images of HEK293 cells and *E. coli* grown in co-culture. HEK293 cells were tagged with DAPI (blue) and Phalloidin Cruzfluor 488 conjugate (green), and *E. coli* were engineered to express mCherry (red). Scale bars were 200 µm in each image.

FIG. 12 comprises an absorbance spectra and STS measured redox potentials of silver, iron, and copper sulfides with comparison to the materials discussed elsewhere herein. Redox levels associated with photoproliferation (dashed) and phototoxicity (solid) were marked.

Figure 13:
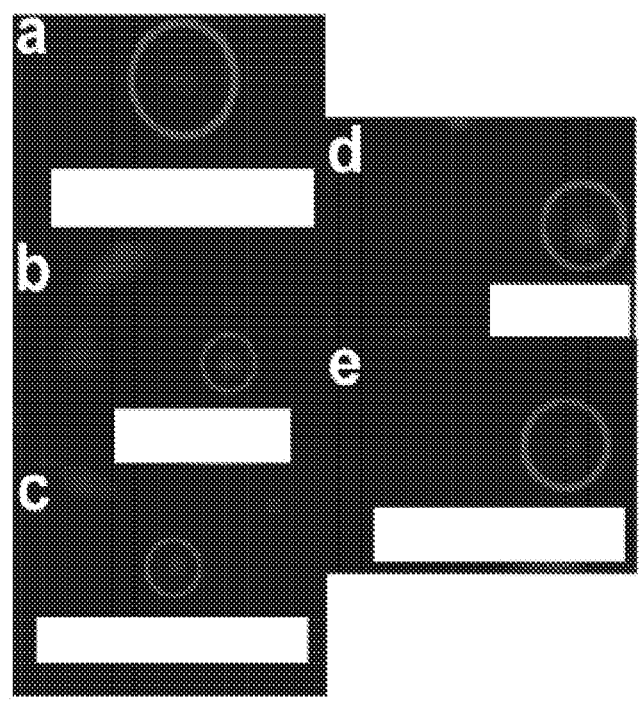

FIG. 13 comprises STM images of (a) 2.6 eV CdSe, (b) 2.4 eV CdSe, (c) 2.4 eV CdTe, (d) 2.2 eV CdTe, (e) 1.6 eV $CuInS_2$. Scale bars were 50 nm in each image. Individual QDs were circled in blue.

Figure 14:
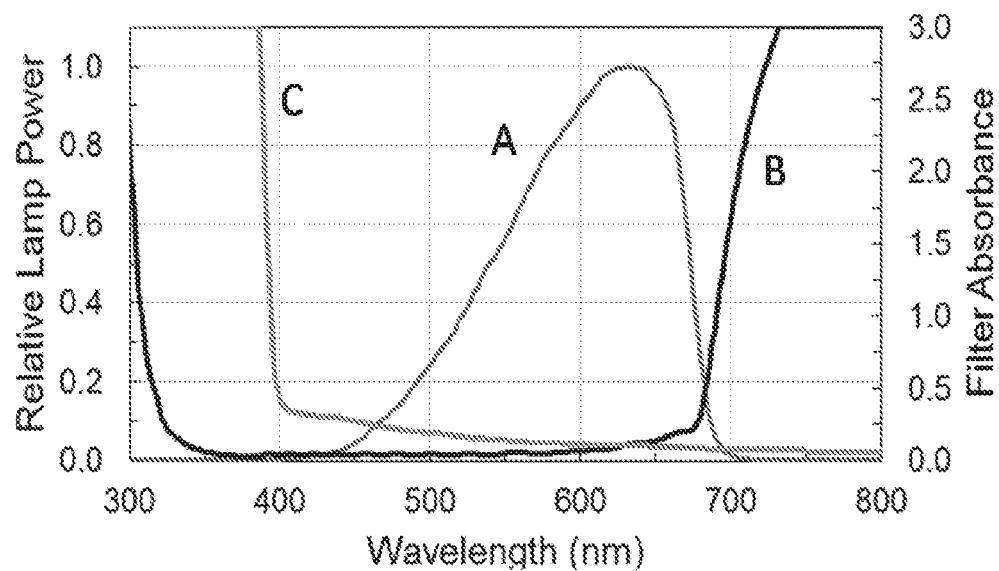

FIG. 14 comprises a graph illustrating a lamp emission spectrum (red, A) and filter absorbance spectra (IR—black, B, UV—blue, C).

Figure 15A:
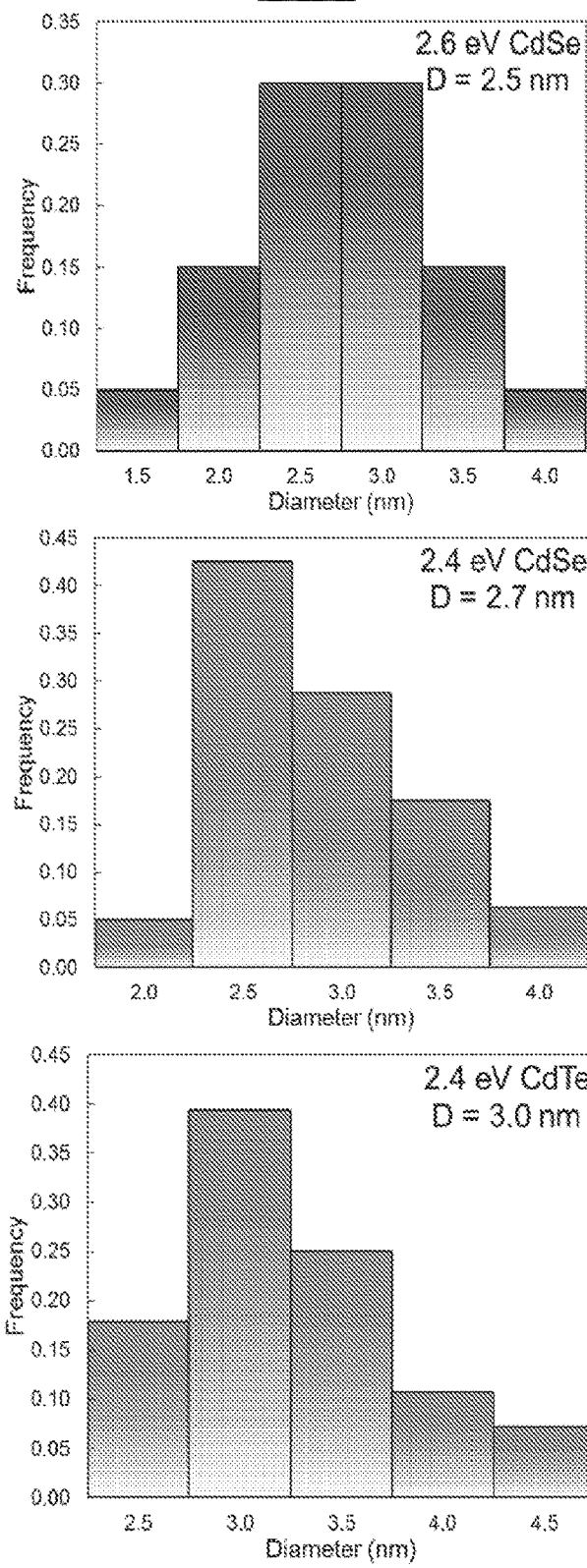

FIGS. 15A-15B comprise a series of graphs illustrating size distribution histograms of various quantum dots.

FIGS. 16A-16C comprise graphs illustrating individual replicates of CIS photoresponse. FIG. 16D comprises a graph illustrating proliferation with statistically significant points ($p<0.05$) marked.

Figure 3A:
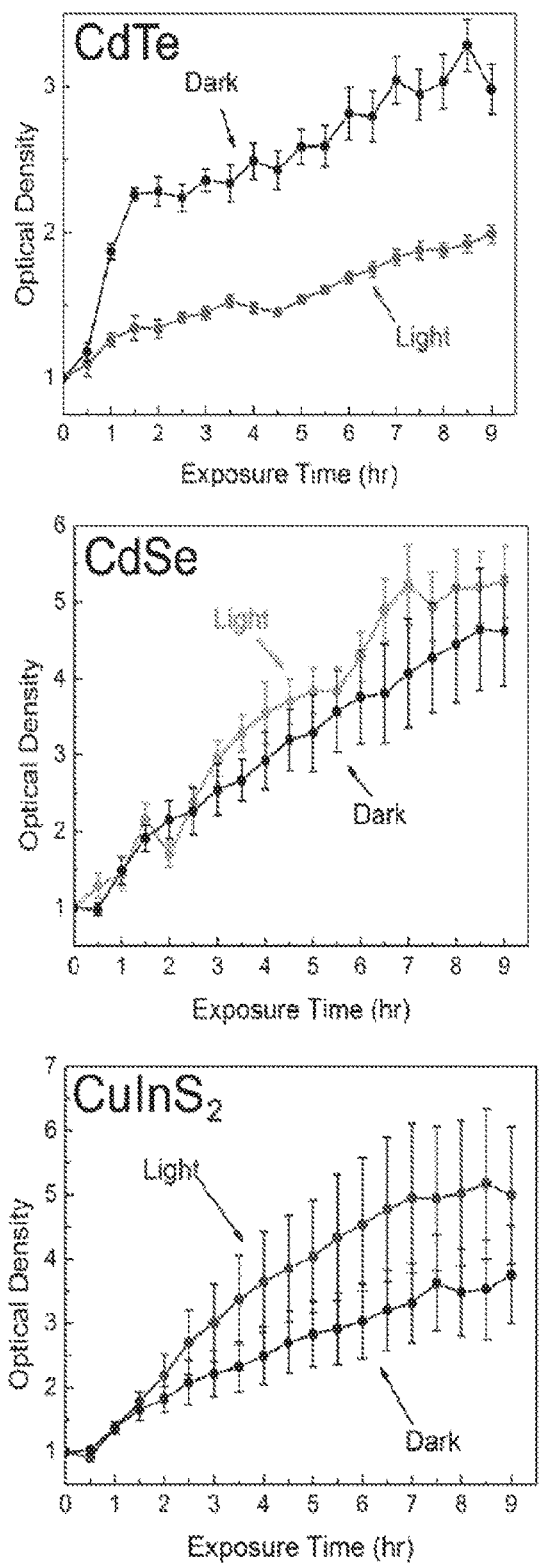
FIG. 3A comprises a series of graphs illustrating optical density curves used to track E. coli growth over time with exposure to QDs in light and dark.
Figure 3C:
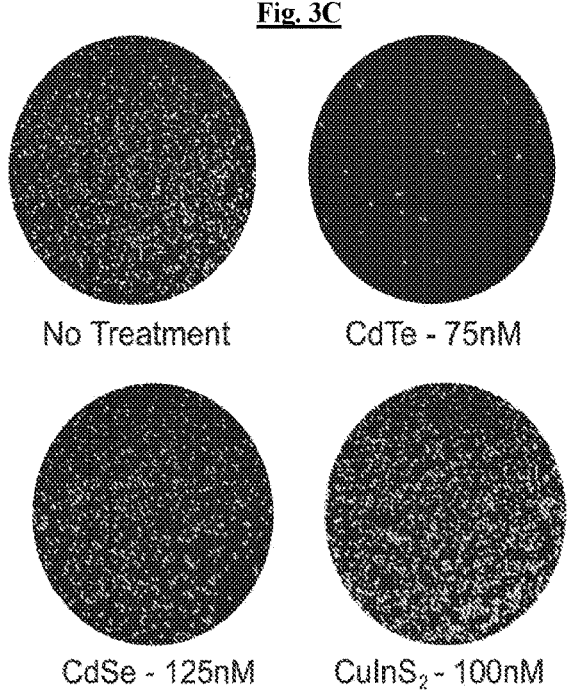
FIG. 3C comprises a series of images of cell colonies that were plated and grown following exposure to quantum dots and light.
Figure 17:
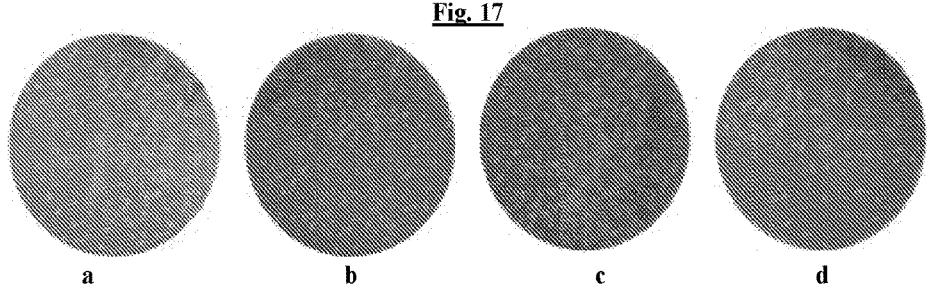

FIG. 17 illustrates plates of culture shown in FIG. 3C under dark conditions. (a) No treatment, (b) 75 nM CdTe, (c) 125 nM CdSe, and (d) 100 nM $CuInS_2$.

Figure 18:
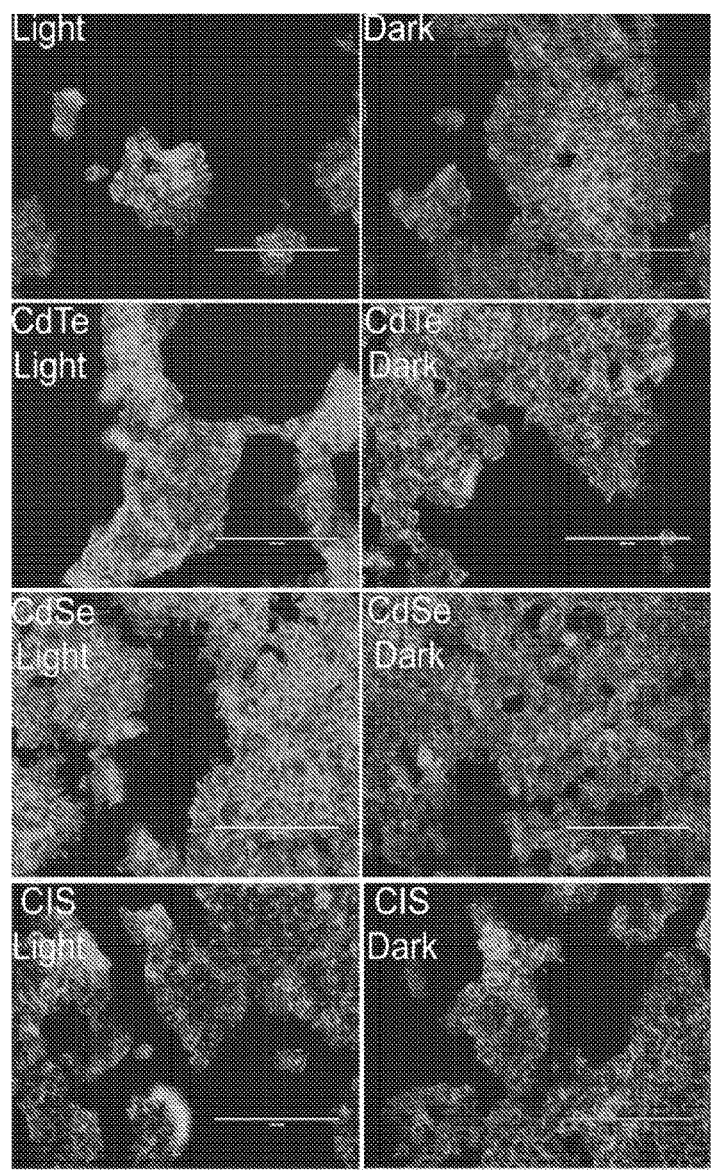

FIG. 18 illustrates images of HEK293 cells after exposure to quantum dots.

Figure 19A:
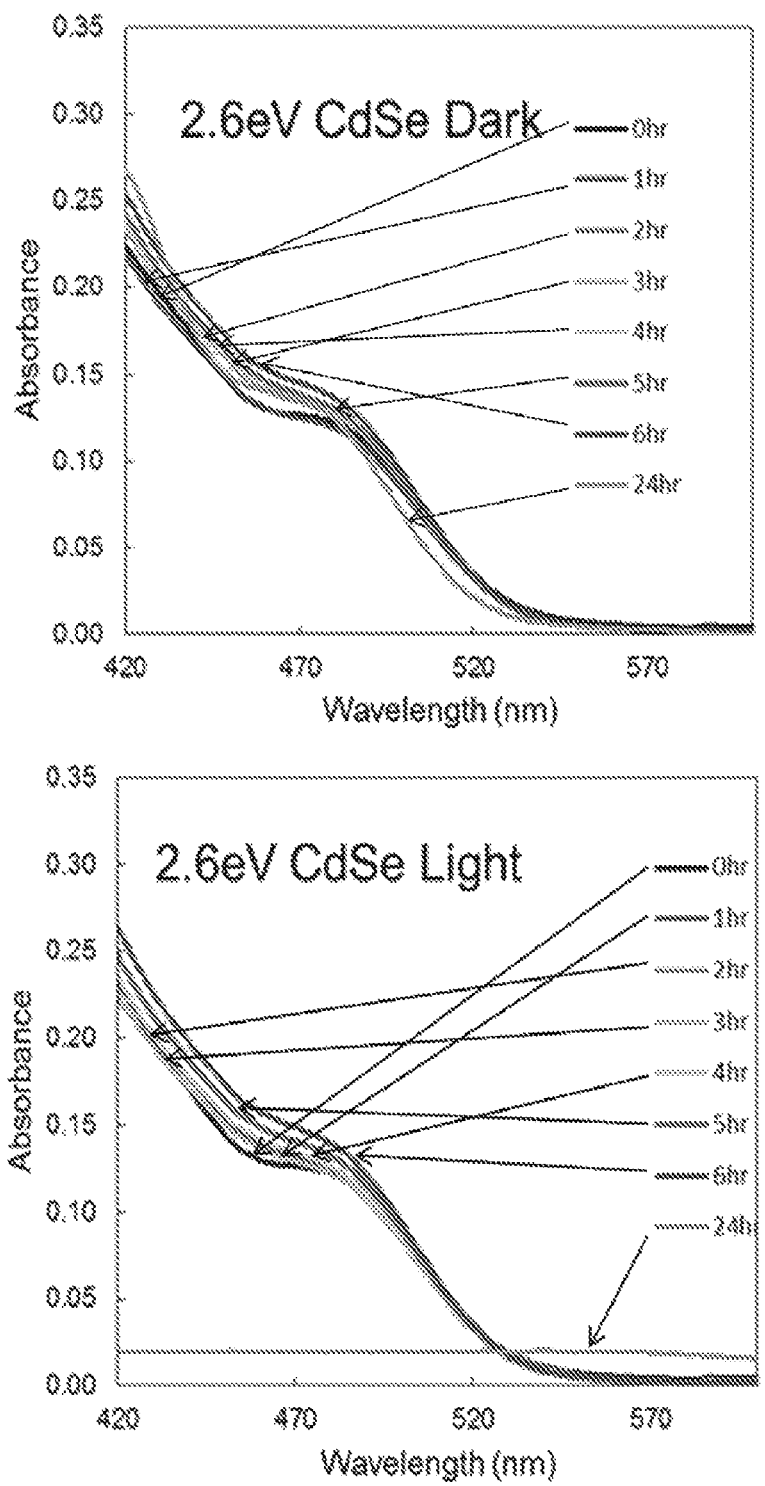

FIGS. 19A-19B comprise graphs illustrating changes in CdSe absorbance over time in light and dark while in the 37° C. incubator.

Figure 20A:
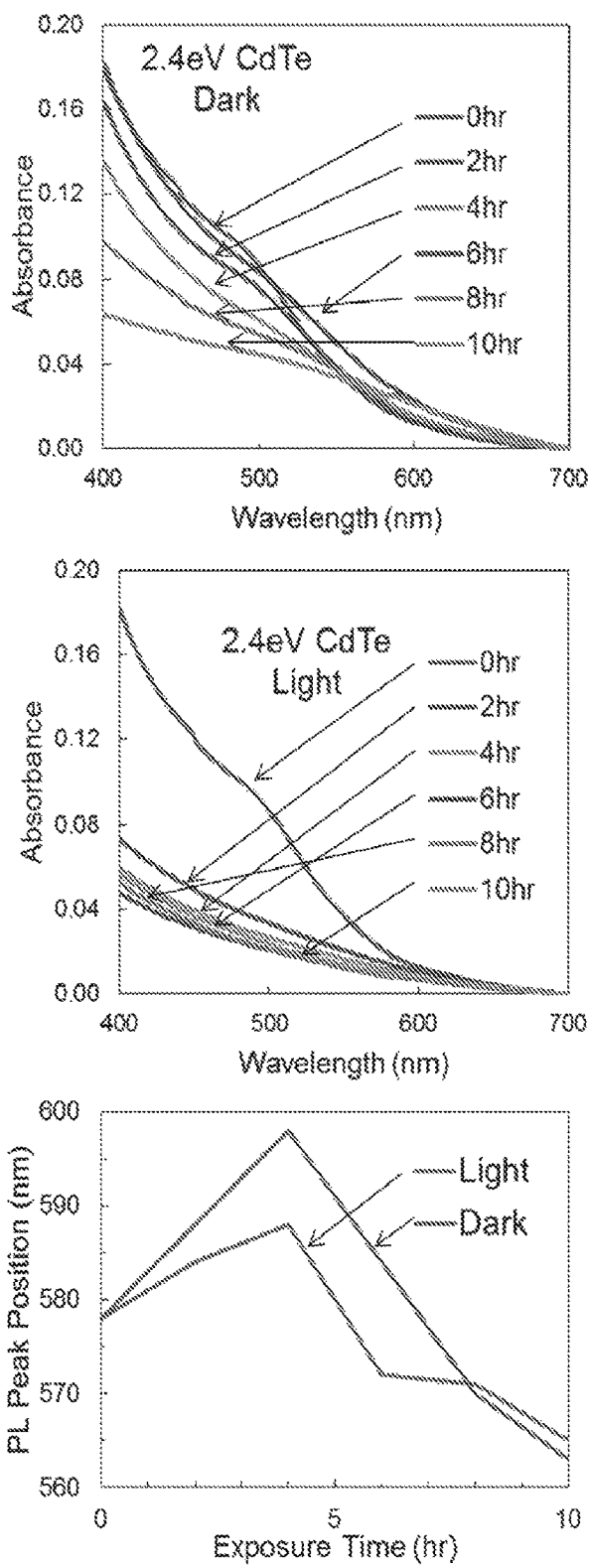

FIGS. 20A-20B comprise graphs illustrating absorbance spectra of the CdTe quantum dots over time light and dark while in the 37° C. incubator. On the bottom of FIGS. 20A-20B are plots tracking the peak position of the PL emission of the two sizes over time.

Figure 21:
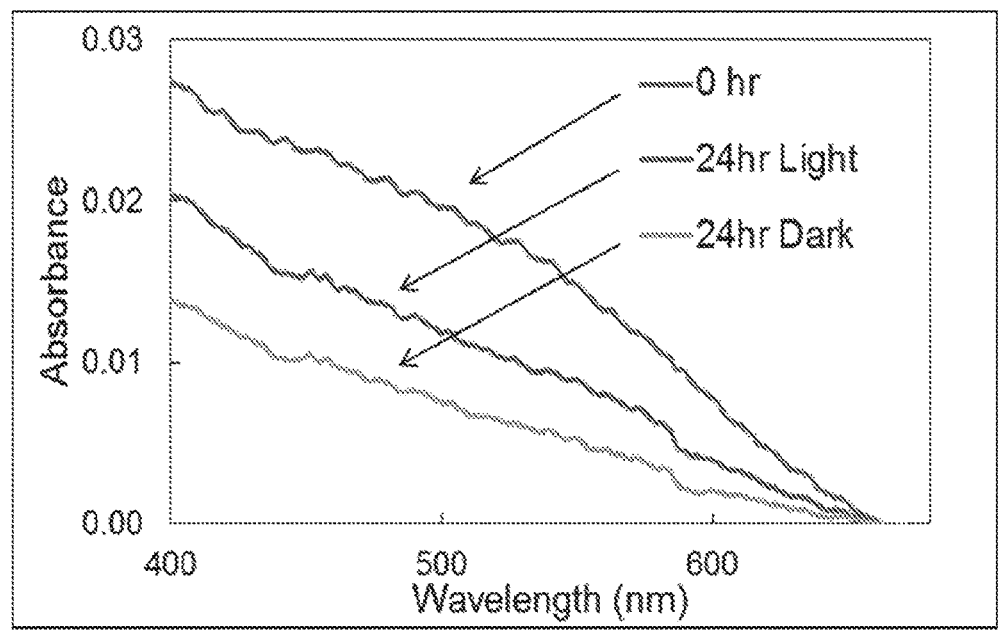

FIG. 21 comprises a graph illustrating absorbance spectra after 24 hours of incubation of the 1.9 eV $CuInS_2$ particles.

Figure 22:
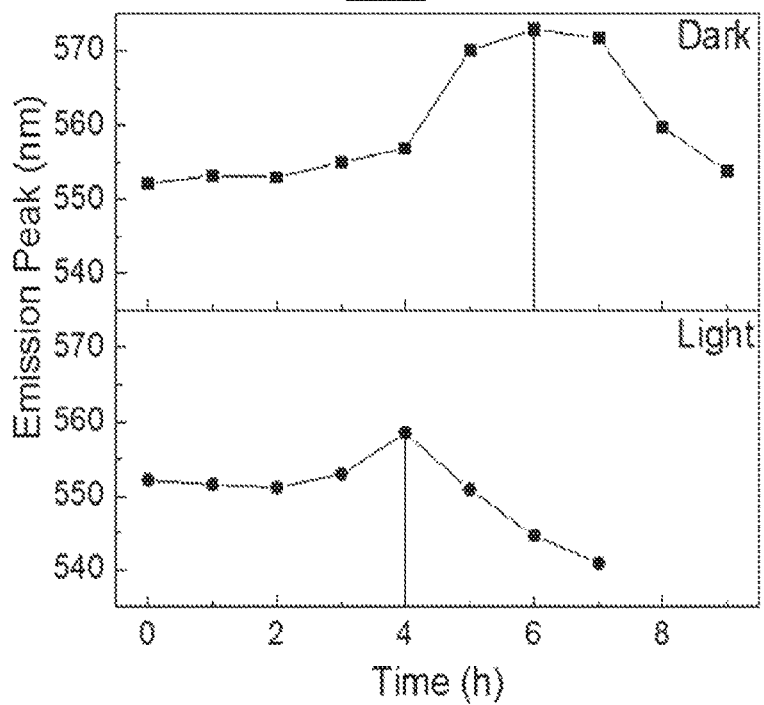

FIG. 22 comprises graphs illustrating degradation profiles of the CdTe cores in light and dark conditions.

FIG. 23A comprises graphs illustrating optical properties of CdTe-2.4 coated with MPA and cysteamine (CA). FIG. 23B comprises graphs illustrating degradation profiles of the CA-coated CdTe particles in light and ark. FIG. 23C comprises a graph illustrating optical density growth curves of MG1655 *E. coli* exposed to the CA-coated QDs in light and dark. FIG. 23D comprises a graph illustrating inhibition as a function of quantum dot concentration. FIG. 23E comprises a graph illustrating uptake of the MPA (−) and CA (+) coated QDs.

Figure 24B:
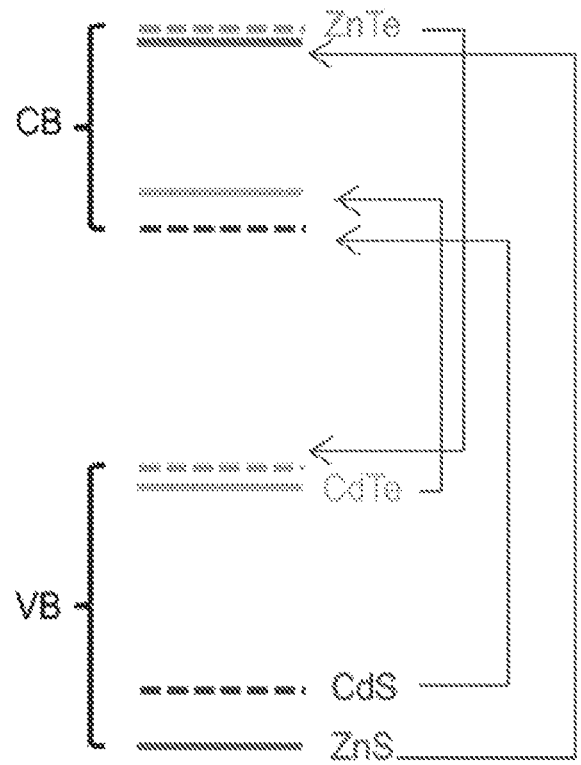
Figure 24C:
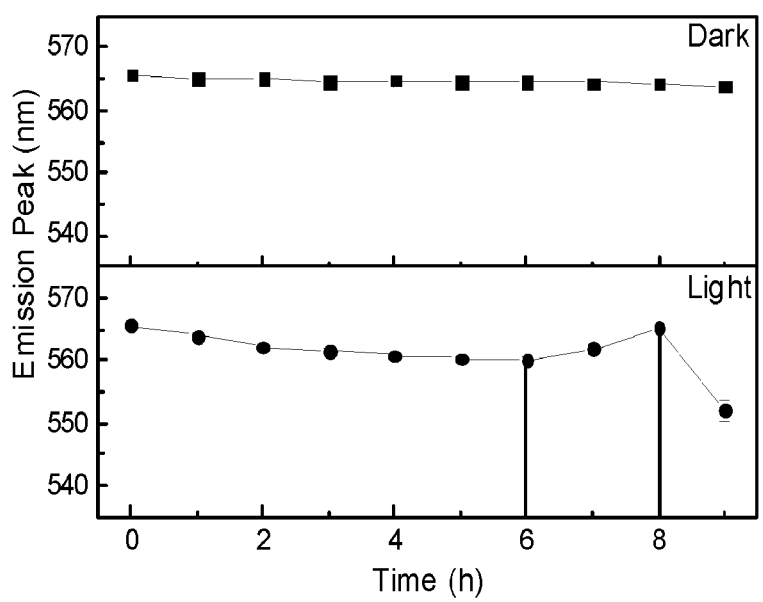

FIG. 24A comprises a graph illustrating optical spectra and quantum yields of the CdTe cores and ZnS@CdTe core-shells. FIG. 24B comprises a diagram illustrating band alignment of CdTe with ZnS and the interface materials. FIG. 24C comprises a graph illustrating degradation profiles of the core-shells in light and dark.

Figure 25A:
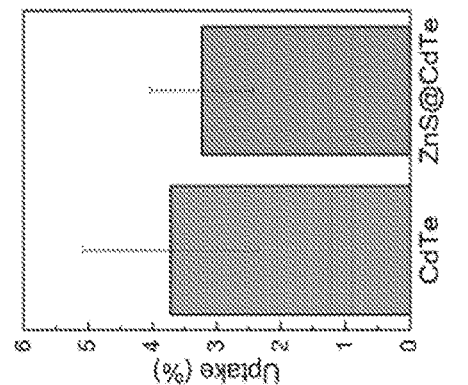
Figure 25B:
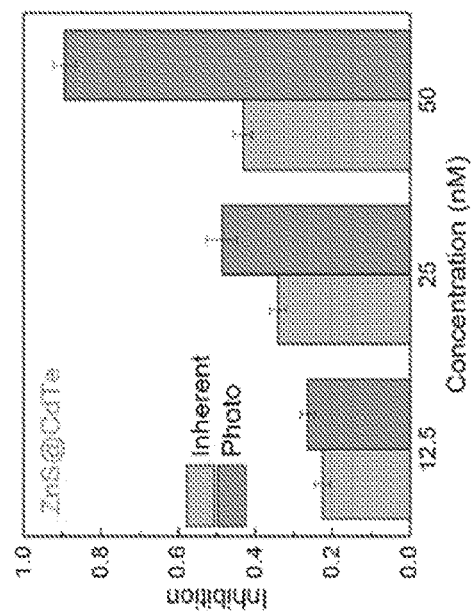
Figure 25C:
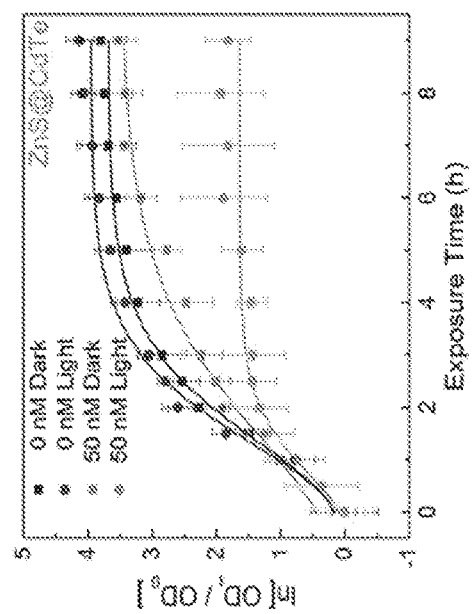

FIG. 25A comprises a graph illustrating optical density growth curves of MG1655 *E. coli* exposed to the core-shells in light and dark. FIG. 25B comprises a graph illustrating on inhibition as a function of quantum dot concentration. FIG. 25C comprises a graph illustrating uptake of the core-shells compared to cores.

Figure 26B:
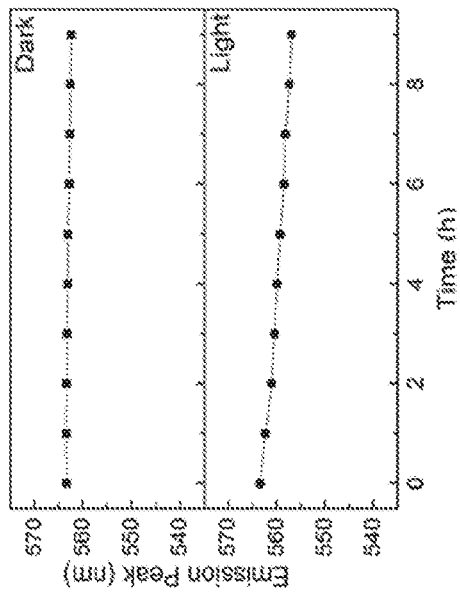
Figure 26A:
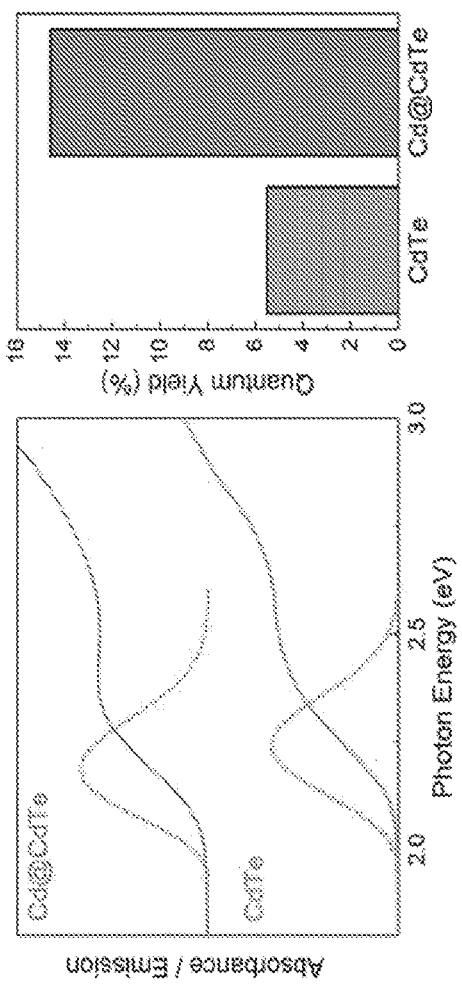
Figure 26E:
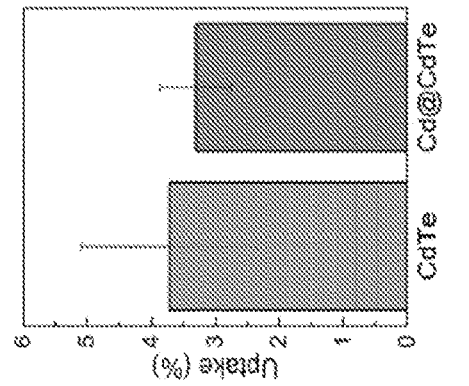
Figure 26D:
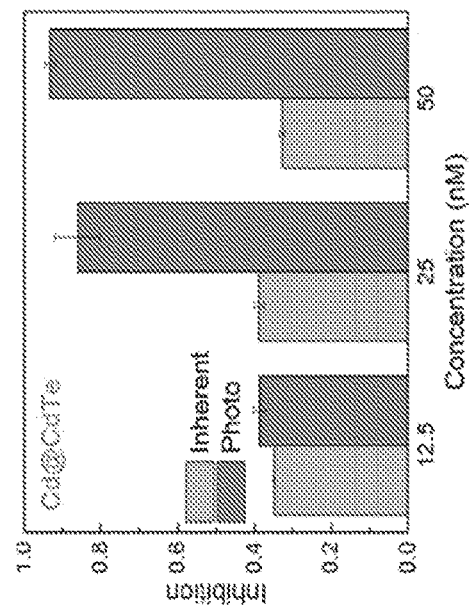
Figure 26C:
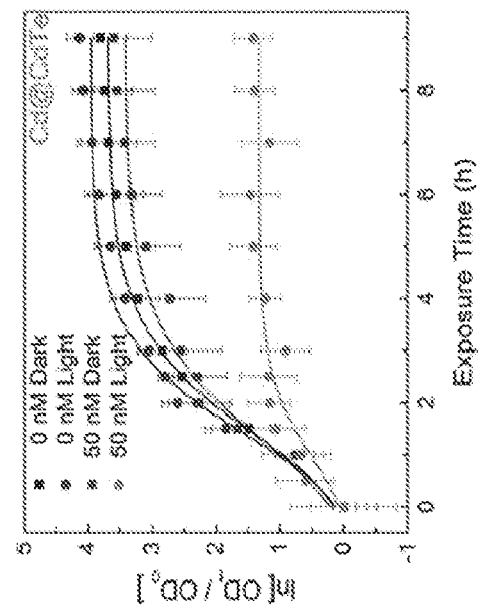

FIG. 26A comprises a set of graphs illustrating optical properties and fluorescence quantum yield of the Cd@CdTe particles compared to cores. FIG. 26B comprises a set of graphs graph illustrating emission peak changes during exposure to PBS in light and dark conditions of the core-shells. FIG. 26C comprises a graph illustrating optical density growth curves of MG1655 *E. coli* exposed to Cd@CdTe. FIG. 26D comprises a graph illustrating inhibition as a function of quantum dot concentration. FIG. 26E comprises a graph illustrating uptake of the core-shells compared to cores.

Figure 27A:
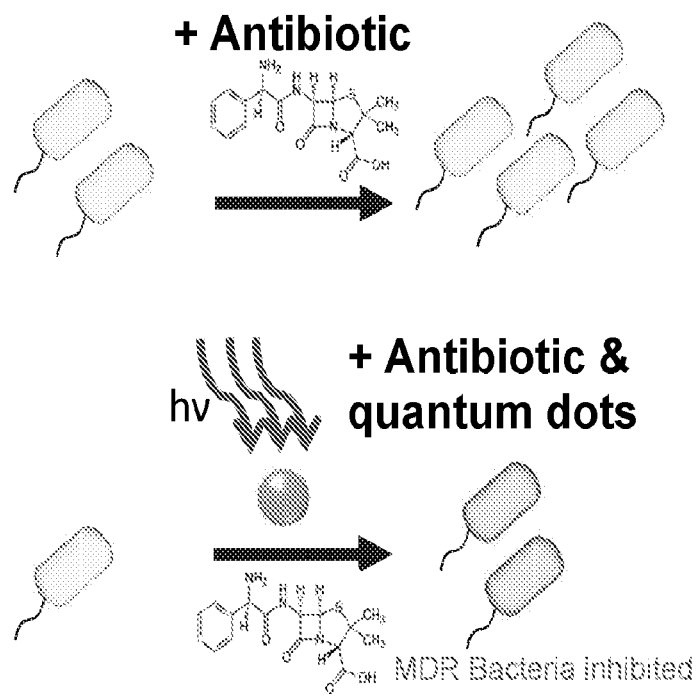

FIG. 27A comprises a schematic representation of the finding that combination of nanoparticles with antibiotics provides an efficacious combination therapy that works to inhibit multi-drug resistant bacteria. FIG. 27B comprises a series of graphs that illustrate characterization of multidrugs resistant strains used in the study, showing the high level of resistance to many classes of antibiotics. Five antibiotics are exemplified. FIGS. 27C-27D comprise a set of graphs illustrating the finding that combination of streptomycin with CdTe-2.4 quantum dot at varied antibiotic and CdTe-2.4 concentrations has significant inhibitory antibacterial effect.

Figure 28B:
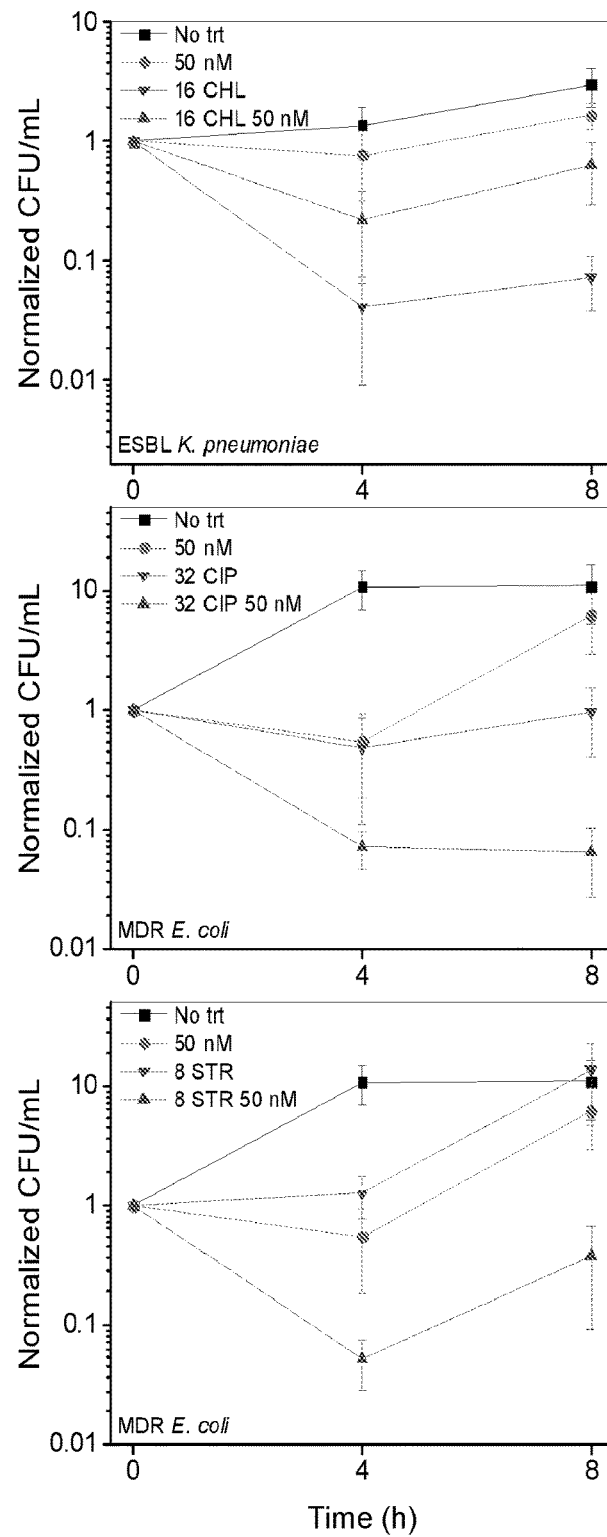

FIG. 28A comprises a set of images illustrating the combination of CdTe-2.4 with respective antibiotic (shown as the $IC_{50}$ of the strain divided by the CLSI or breakpoint) and respective strain represented as the OD at 8 h with treatment divided by the OD at 8 h in no treatment. A color of white or red indicates the combinations effect is at or greater than the $IC_{50}$ of the combination. In certain cases the combination lowers the $IC_{50}$ of the strain to below the CLSI or breakpoint value, as noted by they axis of the heat maps which is $IC_{50}$ of the strain for the antibiotic divided by the CLSI or breakpoint value seen in FIG. 27B. FIG. 28B comprises a set of graph illustrating colony forming unit analysis for 3 combinations in the respective strain, showing significant cell death with combination compared to monotherapy FIG. 29 comprises a set of images illustrating multi-drug resistant strains treated with CdTe-2.4 for 2 hours and stained with DCFH-DA. The results suggest that the mechanism of action comprises production of reactive oxidative species upon illumination inside the cell.

DETAILED DESCRIPTION OF THE INVENTION

The present invention relates, in one aspect, to the fact that therapeutics that alter redox homeostasis can be used to target unique cellular redox environments. In certain embodiments, the tunability of redox potentials of quantum dots (QDs) can be used to specifically perturb redox environments that are unique to cell types.

QDs are nanoparticles that are tunable due to quantum confinement effects resulting from their small size. Their dimensions allow them to diffuse across membranes and accumulate in the intracellular environment or associate with cellular outer membranes. Further, the tunability of QDs allows for the control of their optical absorption and band edge redox potentials. For example, as illustrated in FIG. 1A, three distinct QD materials have shifted band edge redox potentials, even though they have the same optical bandgap. This redox tunability allows for targeting specific cellular processes upon light stimulation and the inducement of desired effects.

As described herein, QDs induce light-activated reactive species (LARS) within cells, and have distinct effects on the cell, depending on the cell type studied. In certain embodiments, LARS generated from tuned QDs are herein alter cellular phenotype; QDs upon illumination with visible light may be phototoxic, benign, or photo-proliferative to *Escherichia coli* cells (FIG. 1B). As demonstrated herein, this cellular phenotype tuning is not a material-specific property but is indeed dependent on the tuned electronic properties of the QDs. Further, the results presented herein show selective, redox tuned cell death with co-culture studies of bacteria and mammalian, indicating that the compositions of the invention can be used therapeutically.

Further, as described herein, the compositions of the invention can be combined with one or more antibiotic agents, and such combinations are effective in killing, or preventing and/or hampering the growth of gram-negative bacteria. In certain embodiments, the gram-negative bacteria are multi-drug resistant. In other embodiments, the concentration or amount of the antibacterial agent in the combinations of the invention that kill, or prevent and/or hamper the growth of gram-negative bacteria, is lower than the concentration or amount of the antibacterial agent that is required to kill, or prevent and/or hamper the growth of gram-negative bacteria when the antibacterial agent is used alone.

Definitions

As used herein, each of the following terms has the meaning associated with it in this section.

As used herein, unless defined otherwise, all technical and scientific terms generally have the same meaning as commonly understood by one of ordinary skill in the art to which this invention belongs. Generally, the nomenclature used herein and the laboratory procedures in biology, chemistry and material science are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more specifically ±5%, even more specifically ±1%, and still more specifically ±0.1% from the specified value, as such variations are appropriate to perform the disclosed methods.

As used herein, the term "band edge redox potential" for a material corresponds to the band edge of the conduction band state (reduction potential) and the band edge of the valence band state (oxidation potential).

As used herein, the term "electromagnetic radiation" includes radiation of one or more frequencies encompassed within the electromagnetic spectrum. Non-limiting examples of electromagnetic radiation comprise gamma radiation, X-ray radiation, UV radiation, visible radiation, infrared radiation, microwave radiation, radio waves, and electron beam (e-beam) radiation. In one aspect, electromagnetic radiation comprises ultraviolet radiation (wavelength from about 10 nm to about 400 nm), visible radiation (wavelength from about 400 nm to about 750 nm) or infrared radiation (radiation wavelength from about 750 nm to about 300,000 nm). Ultraviolet or UV light as described herein includes UVA light, which generally has wavelengths between about 320 and about 400 nm, UVB light, which generally has wavelengths between about 290 nm and about 320 nm, and UVC light, which generally has wavelengths between about 200 nm and about 290 nm. UV light may include UVA, UVB, or UVC light alone or in combination with other type of UV light. In one embodiment, the UV light source emits light between about 350 nm and about 400 nm. In some embodiments, the UV light source emits light between about 400 nm and about 500 nm.

As used herein, the term "instructional material" includes a publication, a recording, a diagram, or any other medium of expression that may be used to communicate the usefulness of the compositions and/or methods of the invention. In certain embodiments, the instructional material may be part of a kit useful for generating compositions of the invention. The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; instructions for use of the compositions; or instructions for use of the compositions.

As used herein, the term "LARS" refers to light-activated reactive species.

As used herein, the term "MPA" refers to 3-mercaptopropionic acid.

As used herein, the term "QD" refers to quantum dot.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6, and so on, as well as individual numbers within that range, for example, 1, 2, 2.7, 3, 4, 5, 5.3, and 6. This applies regardless of the breadth of the range.

Disclosure

The present invention comprises, in one aspect, a novel nanoparticle-based therapeutic strategy using light-activated quantum dots (QDs) that specifically tune phenotypic responses of *Escherichia coli* and HEK293 to changes in redox properties of nanomaterials. The resulting light-activated reactive species are selectively phototoxic, benign, or photo-proliferative depending on the quantum dot redox potentials and cell type. The photoeffects observed in cellular phenotype are not material-dependent properties, but rather due to the tuned electronic properties of the QDs. The present studies demonstrate that the compositions of the present invention can be used in a potential therapeutic intervention, and show selective, redox tuned cell death with co-culture studies of *E. coli* and HEK293 cells. In certain embodiments, the compositions of the invention can be used as antimicrobial agents that selectively targets the redox environment of bacteria and not that of mammalian cells. In other embodiments, the compositions of the invention can be used to alter the redox state of any potential organism of interest. Changes in redox homeostasis of human cells can cause enhanced cell proliferation by interfering in signal transduction pathways in the development of cancer or by creating a reducing environment. This use has application throughout the therapeutic field, as well as a tool for studying the effect of redox states on cellular phenotypes.

As demonstrated herein, the dependence of cellular effect on the quantum dot oxidation and reduction potentials was confirmed, decoupling the effect from the material and the bandgap. A novel photo-proliferative effect with CIS-1.9 particles was observed, where cell growth was enhanced upon light stimulation and the resulting LARS. The tuned CIS-1.9 particle is the first QD study to demonstrate this effect. Taken as a whole, the present results indicate that the compositions and methods of the invention can be used for selective phenotypic tuning of cells.

Compositions

The invention includes a semiconductor-containing nanoparticle, wherein the at least one nanoparticle has a band edge redox potential such that irradiation of the composition with radiation ranging from about 400 nm to about 1,000 nm in the presence of a first cell, under conditions whereby the at least one nanoparticle penetrates the first cell, promotes growth, or kills and/or prevents growth, of the first cell. The invention further includes any compositions including such nanoparticles.

In certain embodiments, the at least one nanoparticle comprises a quantum dot (QD). In other embodiments, the composition is irradiated with radiation ranging from about 750 nm to about 1,000 nm. In other embodiments, the composition further comprises the first cell. In yet other embodiments, the first cell is a bacterium. In yet other embodiments, the bacterium comprises at least one selected from the group consisting of *K. pneumonia, E. coli, S. aureus, P. aeruginosa, A. baumannii* and *S. typhimurium*.

In certain embodiments, the composition further comprises a second cell, wherein irradiation of the composition has no measurable effect on the growth, metabolism and/or survival of the second cell. In other embodiments, the second cell is mammalian.

In certain embodiments, irradiation of the composition in the presence of the first cell promotes growth of the first cell, and the QD comprises $CuInS_2$. In other embodiments, irradiation of the composition in the presence of the first cell kills and/or prevents growth of the first cell, and the QD comprises CdTe. In yet other embodiments, irradiation of the composition in the presence of the first cell promotes growth of the first cell, and the band edge of the conduction band state (reduction potential) of the QD is about +0.2 V and the band edge of the valence band state (oxidation potential) of the QD is about −1.8 V, as referenced to NHE (standard hydrogen electrode). In yet other embodiments, irradiation of the composition in the presence of the first cell promotes death and/or prevent growth of the first cell, and the band edge of the conduction band state (reduction potential) of the QD is about +0.35 V and the band edge of the valence band state (oxidation potential) of the QD is about −2.1 V, as referenced to NHE (standard hydrogen electrode).

In certain embodiments, irradiation of the composition changes redox homeostasis in the first cell. In other embodiments, irradiation of the composition generates at least one light-activated reactive species in the first cell.

In certain embodiments, the surface of the at least one negatively charged nanoparticle is overall negatively charged. In other embodiments, the surface of the at least one negatively charged nanoparticle is essentially free of positively charged ligands. In yet other embodiments, the surface of the at least one negatively charged nanoparticle is free of positively charged ligands.

In certain embodiments, the at least one nanoparticle comprises CdTe, and the surface of the at least one nanoparticle is at least partially coated with ZnS. In other embodiments, the at least one nanoparticle comprises CdTe, and the surface of the at least one nanoparticle is essentially fully coated with ZnS. In yet other embodiments, the at least one nanoparticle comprises CdTe, and the surface of the at least one nanoparticle is fully coated with ZnS. In other embodiments, the fluorescent quantum yield of the at least one nanoparticle at least partially coated with ZnS is similar, or essentially identical, to that of the at least one nanoparticle without the ZnS coating.

In certain embodiments, the at least one nanoparticle comprises CdTe, and the surface of the at least one nanoparticle is at least partially coated with CdS. In other embodiments, the at least one nanoparticle comprises CdTe, and the surface of the at least one nanoparticle is essentially fully coated with CdS. In yet other embodiments, the at least one nanoparticle comprises CdTe, and the surface of the at least one nanoparticle is fully coated with CdS. In other embodiments, the fluorescent quantum yield of the at least one nanoparticle at least partially coated with CdS is similar, or essentially identical, to that of the at least one nanoparticle without the CdS coating.

In certain embodiments, the nanoparticle of the invention is combined with one or more antibacterial agents, and such combinations kill, or prevent and/or hamper the growth of gram-negative bacteria when irradiated. In other embodiments, the gram-negative bacteria are multi-drug resistant. In yet other embodiments, the concentration or amount of the antibacterial agent in the combinations of the invention is lower than the concentration or amount of the antibacterial agent that is required to kill, or prevent and/or hamper the growth of gram-negative bacteria when the antibacterial agent is used alone.

In certain embodiments, the antibacterial agent comprises a cephalosporin antibiotic, fluoroquinone, or protein synthesis inhibitor. In other embodiments, non-limiting examples of antibacterial agents useful for treating gram-negative bacterial infections include: Amikacin, Aztreonam, Cefdinir, Cefaclor, Cefamandole, Cefditoren, Cefixime, Cefoperazone, Cefotaxime, Cefoxitin, Cefpodoxime, Cefprozil, Cefuroxime, Ceftazidime, Ceftibuten, Ceftobiprole, Ceftriaxone, Chloramphenicol, Ciprofloxacin, Clindamycin, Colistin, Ertapenem, Doripenem, Gatifloxacin, Gentamicin, Imipenem/Cilastatin, Kanamycin, Levofloxacin, Meropenem, Metronidazole, Moxifloxacin, Neomycin, Netilmicin, Ofloxacin, Paromomycin, Polymyxin B, Streptomycin, Thiamphenicol, Tigecycline, and Tobramycin.

Methods

The invention includes a method of promoting growth, or killing or preventing growth, of a first cell. The invention further includes a method of altering redox homeostasis in a first cell.

In certain embodiments, the method comprises irradiating the first cell with radiation ranging from about 400 nm to about 1,000 nm in the presence of at least one semiconductor-containing nanoparticle with a band edge redox potential, under conditions whereby the at least one nanoparticle penetrates the cell.

In certain embodiments, the method comprises irradiating the first cell with radiation ranging from about 400 nm to about 1,000 nm in the presence of at least one semiconductor-containing nanoparticle with a band edge redox potential, under conditions whereby the at least one nanoparticle penetrates the first cell, whereby growth of the first cell is promoted, growth of the first cell is prevented or killing of the first cell is promoted.

In other embodiments, the method comprises irradiating the first cell with radiation ranging from about 400 nm to about 1,000 nm in the presence of at least one semiconductor-containing nanoparticle with a band edge redox potential, under conditions whereby the at least one nanoparticle penetrates the first cell, whereby redox homeostasis in the first cell is altered.

In certain embodiments, the nanoparticle comprises a quantum dot (QD). In other embodiments, the first cell is irradiated with radiation ranging from about 750 nm to about 1,000 nm. In yet other embodiments, the first cell is a bacterium. In yet other embodiments, the bacterium comprises at least one selected from the group consisting of *K. pneumonia, E. coli, S. aureus, P. aeruginosa, A. baumannii* and *S. typhimurium*.

In certain embodiments, the first cell is in the presence of a second cell, and irradiation of the first and second cells in the presence of the at least one nanoparticle has no measurable or significant effect on the growth, metabolism and/or survival of the second cell. In other embodiments, the second cell is mammalian. In yet other embodiments, growth of the first cell is promoted, and the QD comprises $CuInS_2$. In yet other embodiments, growth of the first cell is prevented or killing of the first cell is promoted, and the QD comprises CdTe. In yet other embodiments, growth of the first cell is promoted, and the band edge of the conduction band state (reduction potential) of the QD is about +0.2 V and the band edge of the valence band state (oxidation potential) of the QD is about −1.8 V, as referenced to NHE (standard hydrogen electrode). In yet other embodiments, growth of the first cell is prevented or killing of the first cell is promoted, and the band edge of the conduction band state (reduction potential) of the QD is about +0.35 V and the band edge of the valence band state (oxidation potential) of the QD is about −2.1 V, as referenced to NHE (standard hydrogen electrode).

In certain embodiments, irradiation changes redox homeostasis in the first cell. In other embodiments, irradiation generates at least one light-activated reactive species in the first cell.

In certain embodiments, the first cell is further contacted with at least one antibacterial agent. In other embodiments, the first cell comprises a gram-negative bacterium. In yet other embodiments, the first cell comprises a multi-drug resistant gram-negative bacterium. In yet other embodiments, the concentration or amount of the antibacterial agent that is required to kill, or prevent and/or hamper the growth of gram-negative bacteria in the presence of the at least one nanoparticle is lower than the concentration or amount of the antibacterial agent that is required to kill, or prevent and/or hamper the growth of gram-negative bacteria when the antibacterial agent is used alone.

In certain embodiments, the antibacterial agent comprises a cephalosporin antibiotic, fluoroquinone, or protein synthesis inhibitor.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. Although the description herein contains many embodiments, these should not be construed as limiting the scope of the invention but as merely providing illustrations of some of the presently preferred embodiments of the invention.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application. In general the terms and phrases used herein have their art-recognized meaning, which can be found by reference to standard texts, journal references and contexts known to those skilled in the art. Any preceding definitions are provided to clarify their specific use in the context of the invention.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

3-Mercaptopropionic acid (≥99%; also known as MPA) was purchased from Acros Organics. Cadmium(II) chloride (technical grade), 10 mM phosphate-buffered saline, oleic acid (90%), copper(II) acetylacetonoate (≥99.99%), indium (III) acetate (99.99%), sulfur (99.5%), and oleylamine (technical grade) were purchased from Sigma Aldrich. Tellurium-325 mesh powder (99.99% metal basis), and selenium-325 mesh powder (99.5%) were purchased from Alfa Aesar. Sodium borohydride (98%), and sodium hydroxide (≥97.0%), were purchased from Fisher Scientific. Compressed nitrogen (pre-purified), and oxygen gas (ultra-high purity) were purchased from Airgas. Ethanol (200 proof) was purchased from Decon Laboratories INC. All purchased materials were used as provided without further purification.

CdTe and CdSe Quantum Dot Synthesis and Sterilization:

For CdTe, deionized water was initially degassed using bubbling nitrogen for 30 min. 1 mL degassed water was used to dissolve $NaBH_4$ (35 mg, 0.93 mmol), and the resulting solution was transferred to a septum-capped 2 mL vial (Thermo Scientific) containing Te powder (40 mg, 0.31 mmol). Te (325 mesh) was required for the reaction, as coarser Te would not react well.

A needle was inserted into the septum for outgassing during the reaction, which was allowed to proceed until the tellurium precursor solution became optically clear and colorless (40-60 min). A cadmium precursor solution was created by dissolving $CdCl_2$ (3.7 mg, 0.020 mmol) and 3-mercaptopropionic acid (MPA, 1.8 µL, 2.2 mg, 0.021 mmol) in 10 mL of degassed water. The reaction solution was made by mixing 250 µL of the cadmium precursor solution, 250 µL degassed water, 1 µL of the tellurium precursor solution, and 10 µL 0.5 M NaOH (total volume 511 µL). Reactions were scaled up to a maximum of 1.5 mL total volume. 100 µL aliquots of the reaction solutions were divided into PCR tubes (Thermo Scientific), and placed in a thermocycler (Bio-Rad T100). The tubes were held at 98° C. for the reaction duration (1 hour for green emitting CdTe, 2 hours for yellow, 5 hours for red). The quantum dots were then filtered (Omega 4K Nanosep), and washed with pH 10 water. The purified dots were re-dispersed in 150 µL pH 10 water for storage. CdSe was prepared using the same procedure using various masses of Se (25 mg, 0.32 mmol) and $NaBH_4$ (25 mg, 0.66 mmol), the reaction between the two occurring at a much higher rate (<10 min). General procedure was adapted from Tikhomirov, et al., 2011, Nature Nanotech. 6:485-490.

Prior to integration with cells, the CdX quantum dots were sterilized in the following manner. 300 µL of stock QD solution in pH 10 aqueous media were filtered to dryness in a 4K filter. The dots were then washed with 200 µL of ethanol and filtered to dryness. A final wash with 200 µL of autoclaved PBS solutions completed the process, and the dots were re-suspended in PBS. The concentrations of these purified solutions were determined optically using published correlations (Yu, et al., 2003, Chem. Mater. 15:2854-2860).

$CuInS_2$ Quantum Dot Synthesis and Ligand Exchange:

A 100 mL three-necked flask was charged with copper(II) acetylacetonate (260 mg, 1.0 mmol), indium(III) acetate (290 mg, 1.0 mmol), oleylamine (1.0 mL, 1.2 g, 4.5 mmol), and o-dichlorobenzene (7 mL). The flask was then connected to a Schlenk line and purged with alternating vacuum and nitrogen refilling. After three cycles the temperature was increased to 110° C. using a J KEM Scientific Model 210 temperature controller. The sulfur precursor solution was made by dissolving sulfur (64 mg, 2 mmol) in o-dichloro benzene (3 mL) via gently heating. Once dissolved, the sulfur was rapidly injected into the reaction flask and the temperature was increased to 180° C. for the duration of CIS growth. Once the desired reaction time had elapsed the flask was quenched in a water bath, and the contents transferred to a centrifuge tube. Excess ethanol was added and the mixture was centrifuged at 5,000 RPM for 5 min. The precipitated particles were then re-dispersed in chloroform, and centrifuged again to remove poorly passivated dots. Dots that remained in solution were stored for further use along with excess oleylamine to promote stability. Procedure adapted from Panthani, et al., 2008, J. Am. Chem. Soc. 130:16770-16777.

The long-chain amine ligands were exchanged with MPA in the following manner. The hexane stock solution (100 µL), 0.5M NaOH (200 µL), ethanol (500 µL), and MPA (400 µL) were mixed in a 1.5 mL Eppendorf tube that was placed on an Eppendorf Mixmate at 1,000 RPM for 3 hours. The tubes were then centrifuged at 10,000 RPM for 15 min at 10° C. The liquid phase was then removed completely, and the precipitated dots were concentrated in a small volume (<50 µL) of ethanol. This was transferred to a new sterile tube and was vacuum dried to yield a powder. Sterile PBS was then used to re-disperse the dots for use with cells. Concentrations were determined optically using published correlations (Booth, et al., 2012, Chem. Mater. 24:2064-2070). This procedure yields sterile dots, and was scaled by adding more reaction tubes.

Metal Sulfide Syntheses:

Deionized water was initially degassed using bubbling nitrogen for 30 min. A second aliquot of 10 mL deionized water was then degassed in the same way. In this 10 mL metal salts were dissolved ($AgNO_3$:5.5 mg, $FeCl_2$:4.0 mg, CuCl was added until saturated) to form the metal precursor solution. 30 µL 0.5 M NaOH and 750 µL DI water were added to a 1.5 mL Eppendorf tube and placed in an ice bath. 2 µL 3-mercaptopropionic acid were added to the metal precursor solution, and 750 µL of which were added to the Eppendorf tube. 1.5 µL of 630 mM ammonium sulfide solution was then added and the vessel mixed. The tube was left in the ice bath for 30 min before being removed for further experiments, the same sterilization method was employed as used for CdSe/CdTe.

Core Synthesis:

CdTe and CdSe cores of various sizes were synthesized using the materials and methods described elsewhere herein.

Cysteamine Ligand Exchange:

A stock of cysteamine-hydrochloride (CA) was created by dissolving CA (7.7 mg, 0.10 mmol) in 1 mL of 0.1 M HCl, and the pH was adjusted to 6. This was used to re-disperse CdTe-2.4 cores which were filtered, and washed twice with double-distilled water ($ddH_2O$). The QDs were then kept in the dark at room temperature overnight. Prior to use the particles were bulk-centrifuged at 10 krpm for 5 min to remove poorly-passivated QDs, and washed in a similar manner using PBS.

ZnS Core-Shell Synthesis:

A stock 100× solution of zinc and sulphur sources was created by dissolving $Zn(NO_3)_2 \cdot 6H_2O$ (609 mg, 5.57 mmol) and thiourea (75 mg, 1.0 mmol) in 10 mL $ddH_2O$. For a synthesis, 100 µL of the 100× stock was diluted into 10 mL of freshly de-gassed $ddH_2O$ which served as the zinc-sulphur precursor stock. 200 µL of CdTe-2.4 stock were filtered, washed twice and re-dispersed with pH 11 water. This solution was then diluted to 2 µM. The reaction solution consisted of the filtered quantum dots and the precursor stock in a 1:1 ratio, with 10 µL of 0.5 M NaOH per 500 µL of reaction volume. This mixture was then divided into 100 µL PCR tubes and reacted at 98° C. for 1 h. Prior to use in cell cultures they were filtered and washed as described elsewhere herein.

Cd-Overcoat Synthesis:

A Cd-MPA stock was prepared and degassed as described elsewhere herein for the core syntheses. 200 µL of CdTe-2.4 stock were filtered, washed twice, re-dispersed with pH 11 water, then diluted to 2 µM. The QD and Cd-MPA stocks were mixed in equal volumes with 10 µL of 0.5 M NaOH per 500 µL of reaction volume. The reaction solution was then divided into 100 µL PCR tubes and reacted at 98° C. for 15 min.

Scanning Tunneling Spectroscopy:

All STM/STS measurements were taken with a modified Molecular Imaging PicoSPM II Microscope and controller. STM images were taken using a Pt—Ir tip (80:20, Agilent Technologies) with a sample bias of +1.0V and a set-point tunneling current of +0.5 nA (FIG. 13). Indium-tin-oxide (ITO) substrates (Delta Technologies) were prepared prior to use by washing with ethanol, then cleaning by $O_3$ plasma for 5 min (Jelight Company INC UVO Cleaner Model No. 42). Each QD sample was drop cast onto the ITO (10-20 µL of 100-500 nM solution). Scanning tunneling spectra were acquired by varying the voltage across the sample and Pt—Ir tip. The DOS was calculated from the first derivative of the current-voltage curves. The error bars in FIG. 2C represent the spread in CB/VB positions over ~20 independent quantum dot measurements.

Light Source for Cell Studies:

Cells were illuminated using a tungsten lamp (GE 35200-EKE) placed externally of the incubator via a fiber optic cable. The lamp was equipped with filters to remove UV (Thorlabs FEL0400) and IR light, creating a bandpass filter from 400-700 nm (FIG. 14). The lamp was operated at 75% of maximum power for all experiments.

Transmission Electron Microscopy:

TEM images of the nanoparticles were obtained on a Philips CM 100, and were used for confirmation of QD shape and size. CdSe and CIS particles were imaged at 60 kV while CdTe was imaged at 80 kV. Particle size distributions were determined using ImageJ (FIGS. 15A-15B).

Absorbance and Photoluminescence Measurements:

UV-VIS spectra were acquired on a VWR UV1600-PC spectrophotometer at 1 nm resolution. Photoluminescence spectra were measured by illuminating the sample with a UV lamp (UVP UVGL-25) and collecting the resulting emission spectrum with an Ocean Optics USB 4000 detector.

Quantum yields (QY) were determined via comparison with a fluorescein isothiocyanate (FITC, Sigma) standard using a NIST calibrated Photon Technologies International fluorimeter for each sample, with emission measured from 485-800 nm using 475 nm excitation. Each QY was calculated using Equation (1). The emission spectra used in the degradation studies were obtained using a calibrated Ocean Optics USB4000 detector.

$$\frac{\Phi_{QD}}{\Phi_{FITC}} = \frac{A_{FITC} \int_{485}^{800} I_{QD} \lambda d\lambda}{A_{QD} \int_{485}^{800} I_{FITC} \lambda d\lambda} \quad (1)$$

Bacterial Strains and Cell Culture Conditions:

Zymo DH5-α $E.$ $coli$ cells were used, and individual colonies were selected for each replicate. Liquid cultures were grown overnight in 2% lysogeny broth (LB) (incubated at 37° C.), diluted 1:10 into LB with respective quantum dots, and rocked. Solid cultures were grown on 2% LB broth, 1.5% agar at 37° C. Optical density measurements were taken at using a Tecan GENios 562 nm with a bandwidth of 35 nm. All bacterial freezer stocks were stored in 40% glycerol at −80° C.

All multi-drug-resistant (MDR) clinical strains were obtained as a gift from Dr. Nancy Madginer at the University of Colorado, Denver. MDR strains were cultured in cation adjusted Mueller Hinton broth (CAMHB) liquid or 1.5% agar solid for all studies. Cultures were started from individual colonies and grown overnight in 1 mL CAMHB. Bacteria was diluted 1:10 from the overnight for photoeffect experiments. Photoeffect experiments were carried out in 50 uL cultures in 384 well transparent flat bottom plates. Optical density measurements were taken using a Tecan GENios at 562 nm with a bandwidth of 35 nm. All MDR bacterial freezer stocks were stored in 10% glycerol at −80° C.

TABLE 1

MDR clinical isolates

| Graph label | Strain | Special Characteristics |
|---|---|---|
| S1 | MDR $Klebsiella$ $pneumoniae$ | NDM-1 |
| S2 | MDR $E.$ $coli$ | Carbapenem resistant |
| S3 | MDR $Enterococcus$ $faecalis$ | Vancomycin resistant |
| S4 | MDR $Staphylococcus$ $aureus$ | Methicillin resistant (MRSA) |

TABLE 1-continued

MDR clinical isolates

| Graph label | Strain | Special Characteristics |
|---|---|---|
| S5 | MDR $K.$ $pneumoniae$ | Extended-spectrum β-lactamases |
| S6 | MDR $Pseudomonas$ $aeruginosa$ | |
| S7 | MDR $K.$ $pneumoniae$ | |
| S10 | MDR $Salmonella$ $typhimurium$ | Extended-spectrum β-lactamases |
| S12 | MDR $E.$ $coli$ | |
| S13 | MDR $Acinetobacter$ $baumannii$ complex | |

At least for Examples 7-9, colonies of $E.$ $coli$ (MG1655) were grown on solid Luria Bertani (LB, Sigma Aldrich)-agar media overnight at 37° C. from freezer stocks (40% glycerol, −80° C.) and stored at 4° C. For a microplate assay, three individual colonies were grown overnight in LB, and diluted 1:100 when incorporated with the various quantum dots. Separate 96-well flat-bottom plates were prepared for light and dark conditions, the OD of which were measured using a Tecan GENios at 562 nm. Plates were shaken at 225 rpm in a 37° C. incubator between measurements. The dark plate was wrapped in aluminum foil while the edge of the light plate was sealed with parafilm to reduce evaporation. The light source was modulated before each experiment to provide the desired intensity, and was equipped with a 400 nm longpass filter (ThorLabs FGL400) and a 300-700 nm bandpass filter (FGS900-A) to remove UV and IR light.

Statistical Significance of Photoproliferation:

Photoproliferation was analyzed by comparing the average proliferation of the three biological replicates exposed to $CuInS_2$ (FIGS. 16A-16C) to the cell colonies that had no treatment. Comparing the proliferation of these two groups (FIG. 16D) using two-way ANOVA reveals the time points at which statistically significant proliferation occurred.

Colony Forming Unit (CFU) Analysis:

Cultures were sampled at respective time points during a bacterial toxicity study and serial dilutions were performed ranging from $10^2$-$10^{10}$. Dilutions were plated on 2% LB, 1.5% agar, grown at 37° C. for 24 hr, and counted (FIG. 17). Images shown in main text are diluted $10^3$ before plating 10 μL.

Mammalian Cell Culture:

HEK-293T cells were used between passages 11-20. Cells were recovered from freezer stocks in high glucose Dulbecco's Modified Eagle Medium supplemented with glutamine and fetal bovine serum (FBS). Cultures were grown at 37° C. in 5% $CO_2$ with controlled humidity. Cells were passaged at 80% confluency with 0.25% trypsin and seeding densities were calculated using a hemocytometer. Cells were stored in liquid nitrogen for long term storage and −80° C. for short term.

Cells were seeded at 6,000 cells per well into a tissue culture treated 96-well plate (Cellstar). Media was supplemented with penicillin streptomycin solution to minimize the chance of contamination. Quantum dot dilutions were made in sterile Dulbecco's modified phosphate buffered saline (dPBS). Images of these cells were acquired on a microscope after 24 hours of treatment. Three replicate images were taken by randomly imaging different locations in each well. Representative images under all QD conditions shown in FIG. 18.

Co-Culture Experiment:

Co-culture experiments were carried out with HEK-293T cells between passage number 18 and 24 and DH5-α *E. coli* transformed with pFPV-mCherry plasmid (Addgene). The pFPV-mCherry plasmid was used in these experiments for the constitutive production of fluorescent protein mCherry for imaging purposes. 9,000 HEK 293T cells were seeded into 96 well plates and allowed to grow for 36 hours. The 96 well plates were pretreated with 0.01% poly-L-lysine for one hour and rinsed twice with dPBS prior to seeding. Separate 96 well plates were used for the light and dark conditions. pFPV-mCherry *E. coli* were grown for 16 hr from colony under above described bacterial cell culture conditions and with 100 μg/mL ampicillin sodium salt to maintain the plasmid. DMEM was removed from the HEK 293T cultures and supplemented with DMEM containing and approximately $10^5$ bacterial cells/mL, 100 μg/mL ampicillin sodium salt, and respective quantum dots in dPBS. Plates were then placed in an incubator with 5% $CO_2$ at 37° C. for 24 hr either illuminated or shielded from light with tin foil. Media and/or bacterial culture were removed from the wells, pelleted at 7,000 rpm for 5 min, and re-suspended in the same volume of dPBS.

Mammalian cells were then staining with the following procedure; rinsed well twice with dPBS and fixed in 4% methanol free formaldehyde for 5 min. Rinsed again twice with dPBS and treated with 0.1% triton x-100. An additional two rinses with dPBS were followed by staining with a 1× dilution of Phalloidin CruzFluor 488 Conjugate (Santa Cruz Biotechnology) for 20 min. After washing twice with dPBS they were treated with 300 nM DAPI for 5 min. A final set of two washes with dPBS and covering with tin foil to protect stains completes the procedure.

Degradation Studies:

QDs were centrifuged and filtered in the same manner used to prepare stocks for biological assays. Two samples of each type were prepared in PBS to simulate a biologically relevant medium. One was kept in dark, while the other was illuminated using the 100% light intensity used in the assays. Emission spectra were recorded using 365 nm excitation and a calibrated Ocean Optics USB4000 detector.

Uptake Studies:

Three cultures were grown overnight and diluted 1:10 into phosphate-buffered saline with the quantum dots at 100 nM total concentration. The cultures were then shaken for 1 h at 37° C. and collected into centrifuge tubes. The tubes were spun at 15 krpm at 3 min and the supernatant was removed. The cell pellet was then washed twice with PBS and once with double-distilled water using this procedure. The pellet was then dispersed in ~300 μL double-distilled water for storage (final volume was recorded after dispersion).

ICP-MS samples were prepared by diluting 25 μL of the samples to 1 mL total volume. Standards were prepared within the limits of the possible concentration range for comparison. This analysis provided the raw element composition of the samples, which was used to calculate the signal corresponding to specific concentrations. The percentage uptake reported herein are defined using a mass balance comparing the total number of particles associated with the cells with the initial number introduced into the cultures.

Quantum Dot Controls:

Without wishing to be limited by any theory, CdX toxicity could in principle be attributed to release of free cadmium into the intracellular medium. The rate of cell death does not correlate with the concentration of free $Cd^{2+}$ (Cho, et al., 2007, Langmuir 23:1974-1980), which indicates this is not the source of toxicity in this concentration range. Control measurements were performed to track the changes in the QDs for the duration of the cell exposure. The changes in the quantum dots as a result of continued light illumination were examined by absorption and photoluminescense measurements. Absorbance measurements of CdSe particles indicated that the smallest particles were relatively stable in dark and under illuminated reaction conditions, experiencing an attenuation of the excitionic peak slowly over 24 hours of illumination (FIGS. 19A-19B). The largest CdSe particles were, however, less stable than their smaller counterparts, and experienced significant absorbance decreases within 5-6 hours of illumination.

While informative that changes to the particles are taking place, the exact nature of those changes were not clear, based on these absorbance measurements. Because CdTe is photoluminescent in aqueous media, changes in the PL peak position were tracked over time under the same conditions. There was an initial red shift of the emitted light, which was indicative of defect states forming on the quantum dot surfaces, likely oxygen replacing tellurium (FIGS. 20A-20B). Later, the shift reversed, such that the emitted light decreases in wavelength. This result is consistent with the continuing oxidation of the quantum dot leading to a smaller CdTe core that emits lower wavelength light. This blue shift occurs more rapidly in the larger particles, likely due to the lower relative passivation of tellurium rich facets. As CdO has very low solubility in buffered solution, the source of the quantum dot toxicity in light was indeed due to the formation of LARS, and not the release of free $Cd^{2+}$ ions. Without wishing to be limited by any theory, there was a difference between light and dark exposed quantum dots insofar as the intensity of light emission decreased much more rapidly when exposed to light; this indicated that the LARS contributed to the formation of less ordered particles, facilitating non-radiative recombination.

There were less overall changes in the $CuInS_2$ over time compared to the cadmium based dots (FIG. 21), likely due to the greater oxygen stability of sulfur as an anion compared to the other chalcogens.

Example 1: Characterization of Tunable Quantum Dot Properties

Figure 2A:
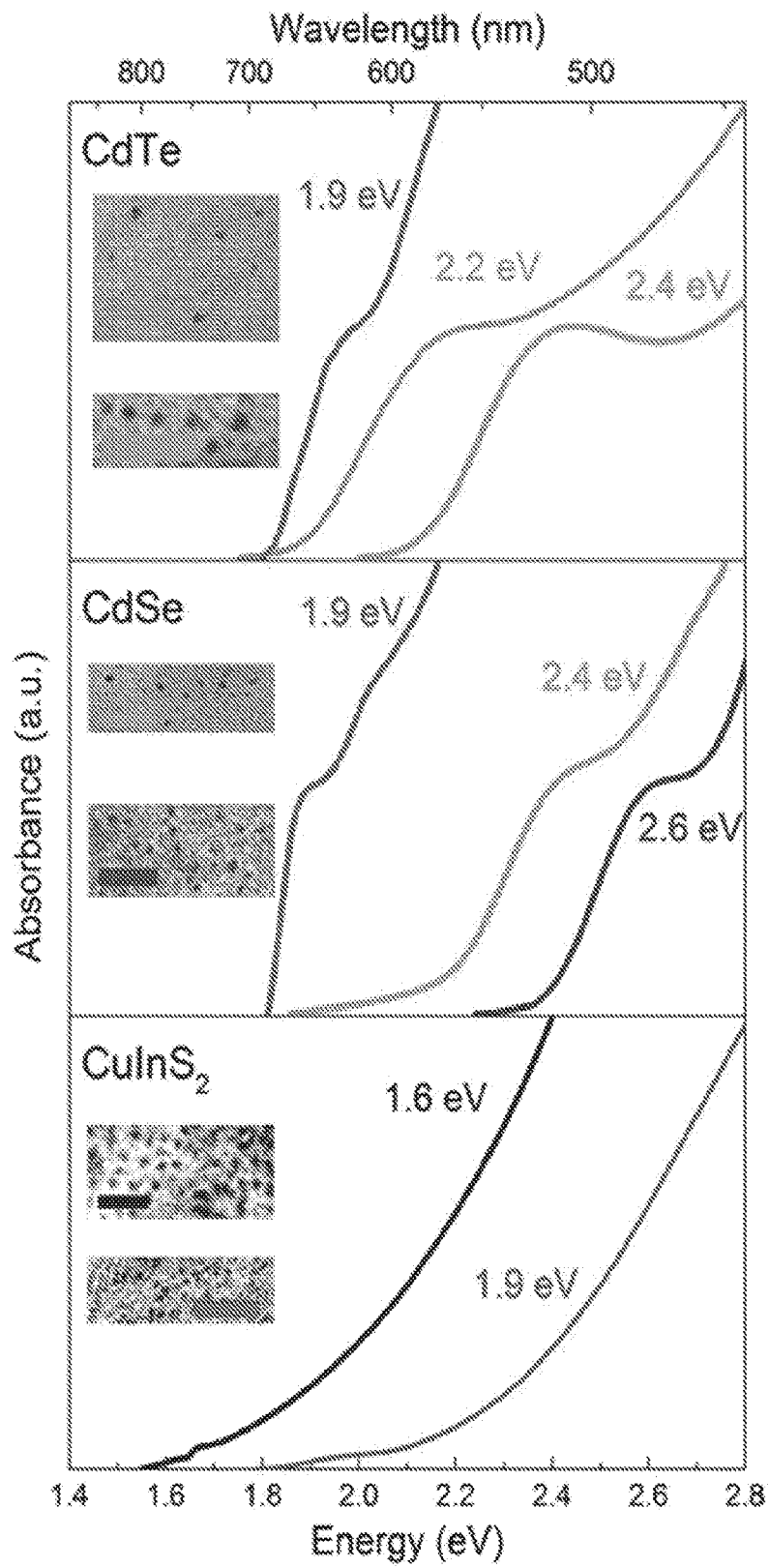
FIG. 2A comprises a series of graphs illustrating absorbance measurements of each material at various sizes. The scale bars in the inset histograms were color coded to the absorbance spectra, and were 50 nm in all cases except the 2.4 eV CdTe, which was 25 nm.

To examine the range of possible effects, cadmium telluride (CdTe), cadmium selenide (CdSe), and copper indium sulfide ($CuInS_2$, CIS) QDs of different sizes, which absorb light across the visible and near-infrared spectra, were prepared (FIG. 2A). Infrared absorbing dots are highly attractive, as human tissue is generally transparent to light from 750-1000 nm allowing in vivo stimulation.

Figure 2B:
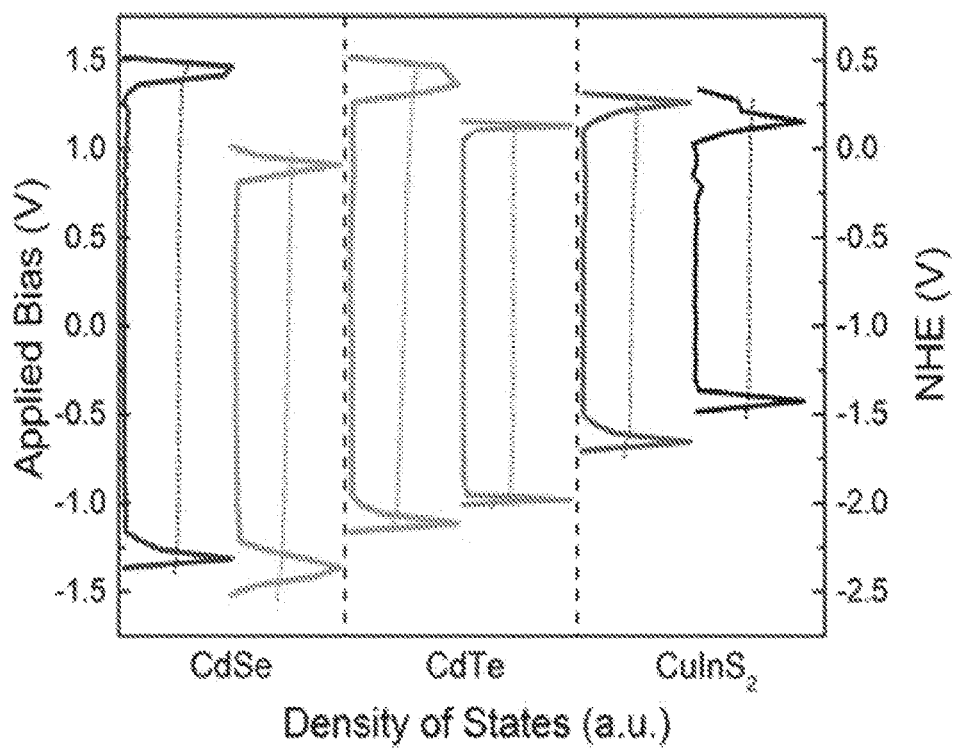
FIG. 2B comprises a graph illustrating STS measurements of individual quantum dots. Color coding matches FIG. 2A.
Figure 2C:
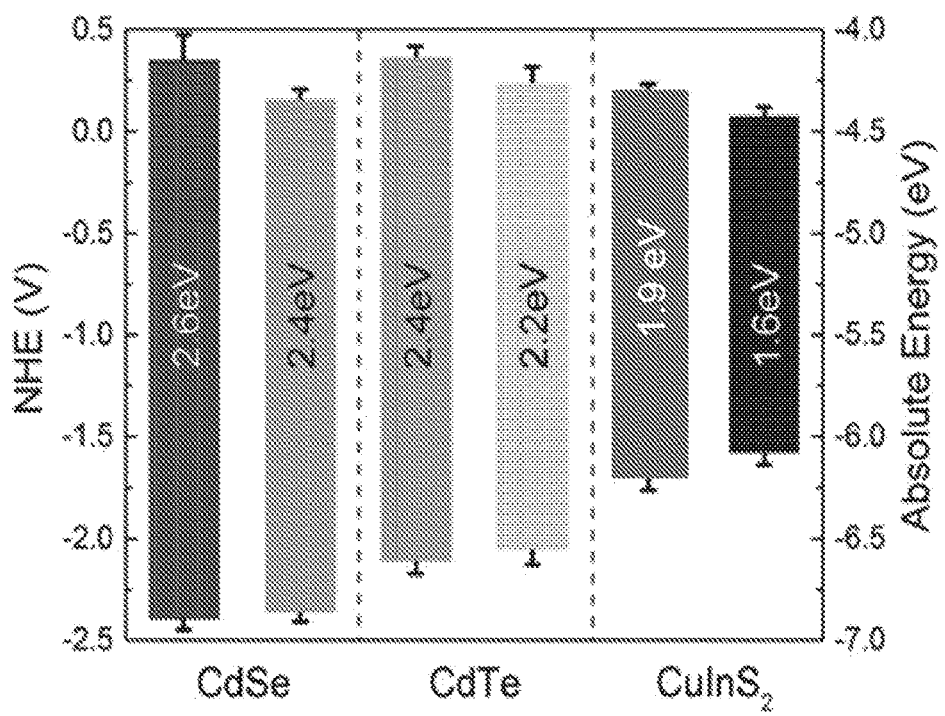
FIG. 2C comprises a graph illustrating the average CB/VB position of various individual quantum dots for each material and size. The extent of the colored box indicates the average while the error bar indicates the upper limit of the band position.

Electronic structures of these materials were quantified using scanning tunneling spectroscopy of individual nanocrystals (FIG. 2B). For clarity of comparison to biochemical systems, these measurements are compared relative to the normal hydrogen electrode potential. Based on these measurements, the band edge states of the various materials, which play the largest role in determining the redox potentials of each quantum dot, were identified. Because the samples were not perfectly mono-disperse, there was a distribution in band position for each size (FIG. 2C). There was a significant size effect with the positions of each material's band edge states. For CdSe and CdTe, a change in size most notably changed the position of the conduction states (reduction potential), while leaving the valence states (oxidation potential) relatively constant. In contrast, both potentials are altered with changing size in CIS QDs.

Example 2: Photoeffect of Quantum Dots on *Escherichia coli*

To evaluate the photoeffect of tuned QDs in a biological environment, CdTe and CdSe of the same bandgap (2.4 eV) with varying redox potentials were selected (FIG. 2c), hereafter referred to as CdTe-2.4 and CdSe-2.4, respectively. 1.9 eV bandgap CIS particles (FIG. 2C, hereafter referred to as CIS-1.9) were also evaluated, because they have the same reduction potential as the CdSe-2.4 particle and a lower oxidation potential than CdSe-2.4 and CdTe-2.4 along with a smaller bandgap. The comparison of CdSe-2.4 to CdTe-2.4 allowed for a direct observation of the effect of the redox potentials as opposed to the bandgap. The comparison of CIS-1.9 to CdSe-2.4 allows for direct observation of the effect of the oxidation potential as the reduction potential is the same for both particles.

QDs were added, in varying concentrations, to *E. coli* cultures and grown rich media while the optical density was monitored using a microplate reader. Cultures were grown in the absence and presence of QDs with and without visible light illumination (lamp spectra with UV and IR filters, FIG. 14).

Exposure in dark was used as a control, as cadmium based QDs can be intrinsically toxic to cells; however, the present studies were performed below reported toxic levels. Further, any intrinsic toxicity would be accounted for in the dark control analysis. Degradation studies of cadmium QDs upon light illumination showed a red shift in quantum dot emission as opposed to a blue shift that would be indicative of free, toxic cadmium release (FIGS. 19A, 19B, 20A, 20B, 21A, 21B).

The studies showed a significant reduction in growth of *E. coli* grown in the presence of CdTe-2.4 particles in light compared to dark (FIG. 3A). If the phototoxicity were an effect of generic ROS, as opposed to the tuned response, higher phototoxicity with illumination of CdSe-2.4 particles would be expected due to their higher oxidation potential. In contrast to this hypothesis, in the presence of CdSe-2.4 and illumination, no significant phototoxicity was observed in *E. coli* (FIG. 3A). Surprisingly, CIS-1.9 particles upon illumination displayed a photo-proliferative effect in *E. coli*.

Evaluating these particles over a concentration range allowed for the determination of the threshold where a photoeffect was observed. In order to assess the photoeffect of the QDs, parameters for phototoxicity (Equation 2) and photo-proliferation (Equation 3) were defined to observe the optical density of cultures in light relative to dark. There was a strong phototoxic effect above 35 nM CdTe-2.4 (FIG. 3B). Contrastingly, there was no significant photoeffect even up to a CdSe-2.4 concentration of 500 nM (FIG. 3B). Plating the cells post exposure confirmed that the CdTe-2.4 is bactericidal in light and not in dark, as evidenced by a large decrease in the number of viable cells whereas CdSe-2.4 did not exhibit a bactericidal photoeffect (FIGS. 3C and 17). Thus, the source of the photoeffect is the specifically tuned redox potentials of the QDs and not the bandgap, which remained constant at 2.4 eV.

$$\text{Phototoxicity}=[(OD_{dark}/OD_{light})-1]\times 100 \qquad (2)$$

$$\text{Photo-proliferation}=[(OD_{light}/OD_{dark})-1]\times 100 \qquad (3)$$

Examining the concentration dependence of CIS-1.9 showed a statistically significantly region of photo-proliferation centered at 100 nM CIS-1.9 (FIG. 3B). There were thresholds below which the generated LARS were at too low of concentration to greatly impact the cell, and above which the LARS are in excess and overwhelm redox homeostasis. The measured photo-proliferation observed with CIS-1.9 differed greatly in the no photoeffect observed for CdSe-2.4. As the bandgap was not the source of the difference in photoeffect between CdTe-2.4 and CdSe-2.4, without wishing to be limited by any theory, a possible conclusion is that the CIS-1.9 photo-proliferation compared to CdSe-2.4 derives from the 0.5 V shift in oxidation potential between the two materials.

Example 3: Confirming *E. coli* Response is Non-Material Dependent

Figure 4:
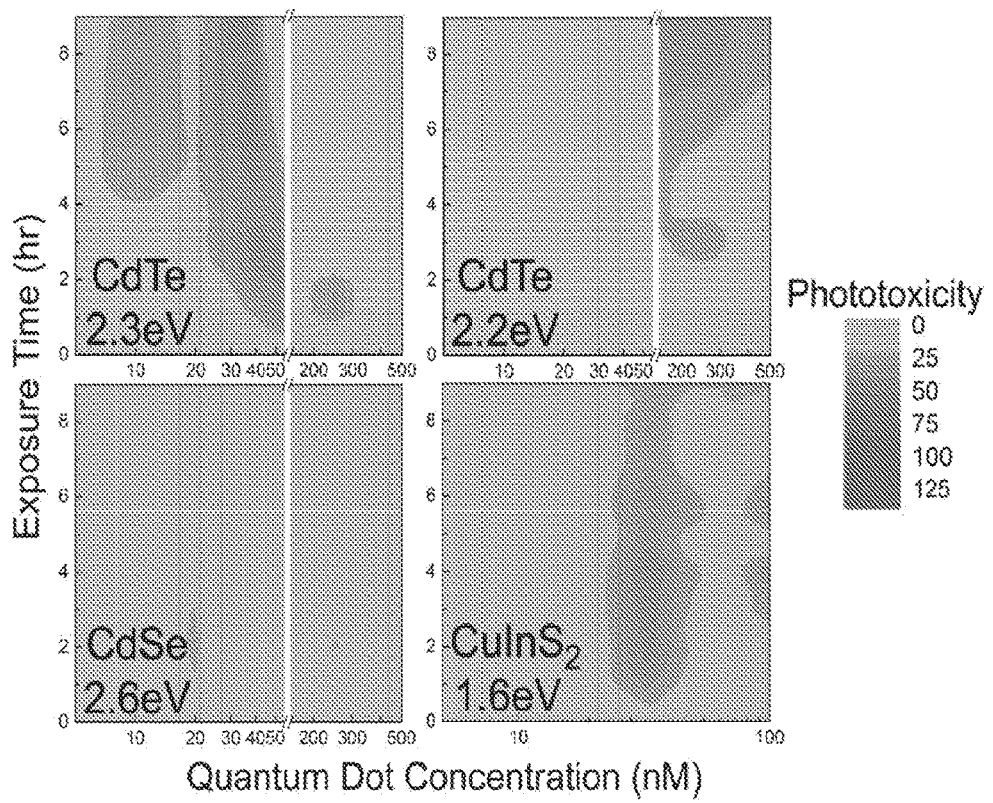
FIG. 4 comprises a series of photoeffect contours comparing the effect of changing quantum dot size for the materials shown in FIGS. 3A-3C.

To observe fine changes in redox potential, various sizes of the three materials were examined to confirm that these were not material dependent properties. The focus was on two CdTe particles, CdTe-2.3 with a bandgap of 2.3 eV and CdTe-2.2 with a bandgap of 2.2 eV. A higher energy CdSe particle with a bandgap of 2.6 eV and a lower energy CIS particle with a bandgap of 1.6 eV, hereafter referred to as CdSe-2.6 and CIS-1.6, respectively, were analyzed as well. CdTe materials showed decrease in the phototoxic effect with decreasing reduction potential (FIG. 4). As the bandgaps changed with increasing size, their reduction potentials moved closer to those of CdSe-2.4, implying that in certain embodiments the conduction band states relate to the phototoxic effect, given the consistency in valence band position (FIG. 2C). This data further precludes the suggestion that phototoxicity is arising from degradation of the QDs, as the larger dots would be more toxic given the greater amount of material they can release.

Interestingly, CdSe-2.6 retained its benign response, even with its reduction potential closer to the CdTe-2.4 level, suggesting that in certain embodiments the oxidation potential determined by the valence band interfered with the generation of toxic LARS. The high selectivity of each redox potential was exemplified by the larger CIS-1.6 QDs. The small change in bandgap led to a slight phototoxic effect, counter to what was observed for CIS-1.9. Unlike CdTe or CdSe materials, both bands moved appreciably with changing size, making neither potential able to activate a photo-proliferative response.

Figure 5A:
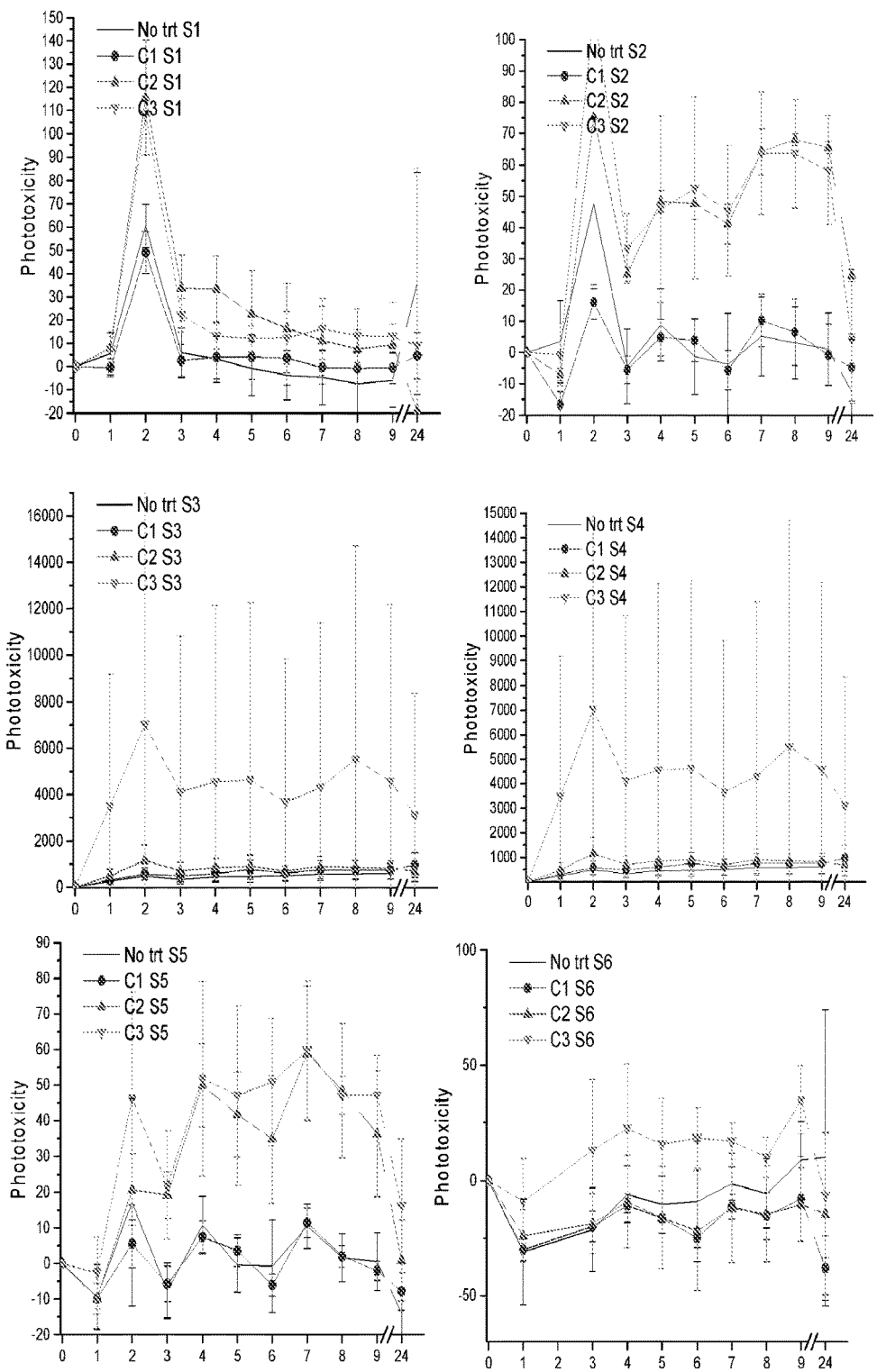
FIGS. 5A-5B comprise a series of graphs illustrating phototoxicity for CdTe-2.4 particles in MDR clinical strains. C1 was 10 nM, C2 was 50 nM, and C3 was 100 nM. Data were normalized to t=0 and the average of 3 biological replicates, and error bars represent standard deviation. Ordinates represent hours (h).
Figure 5B:
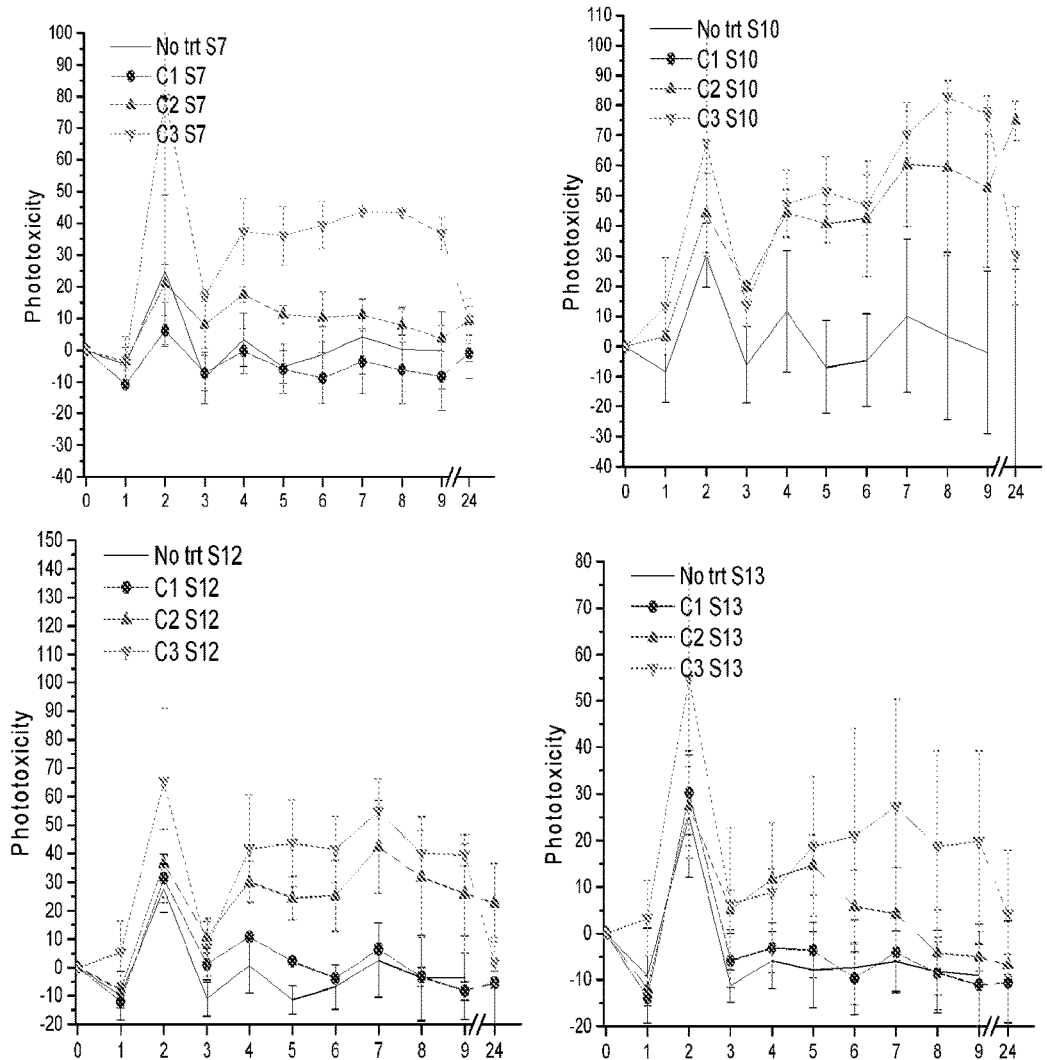
Figure 6A:
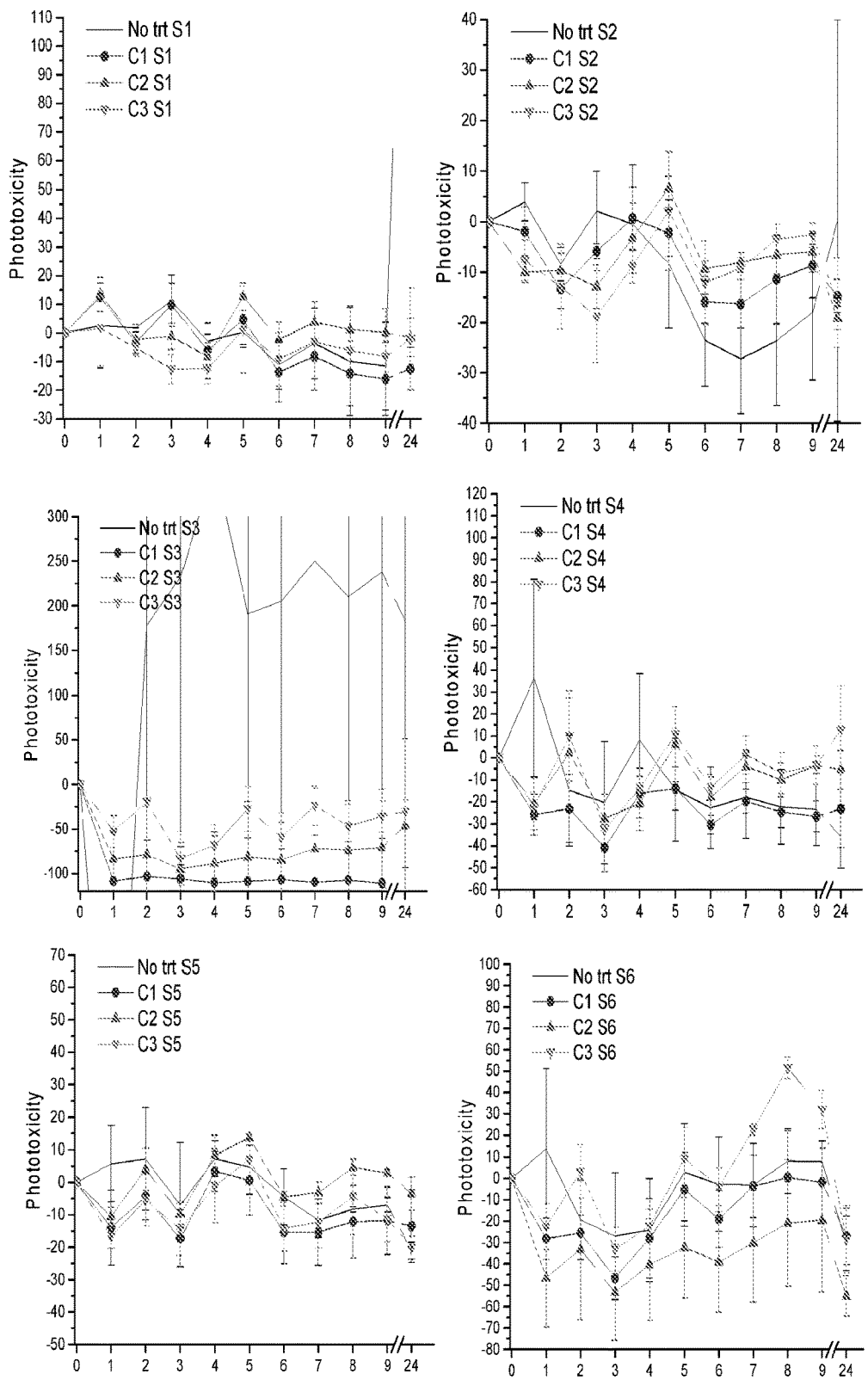
FIGS. 6A-6B comprise a series of graphs illustrating phototoxicity for CdSe-2.4 particles in MDR clinical strains. C1 was 10 nM, C2 was 50 nM, and C3 was 100 nM. Data were normalized to t=0 and the average of 3 biological replicates, and error bars represent standard deviation. Ordinates represent hours (h).
Figure 6B:
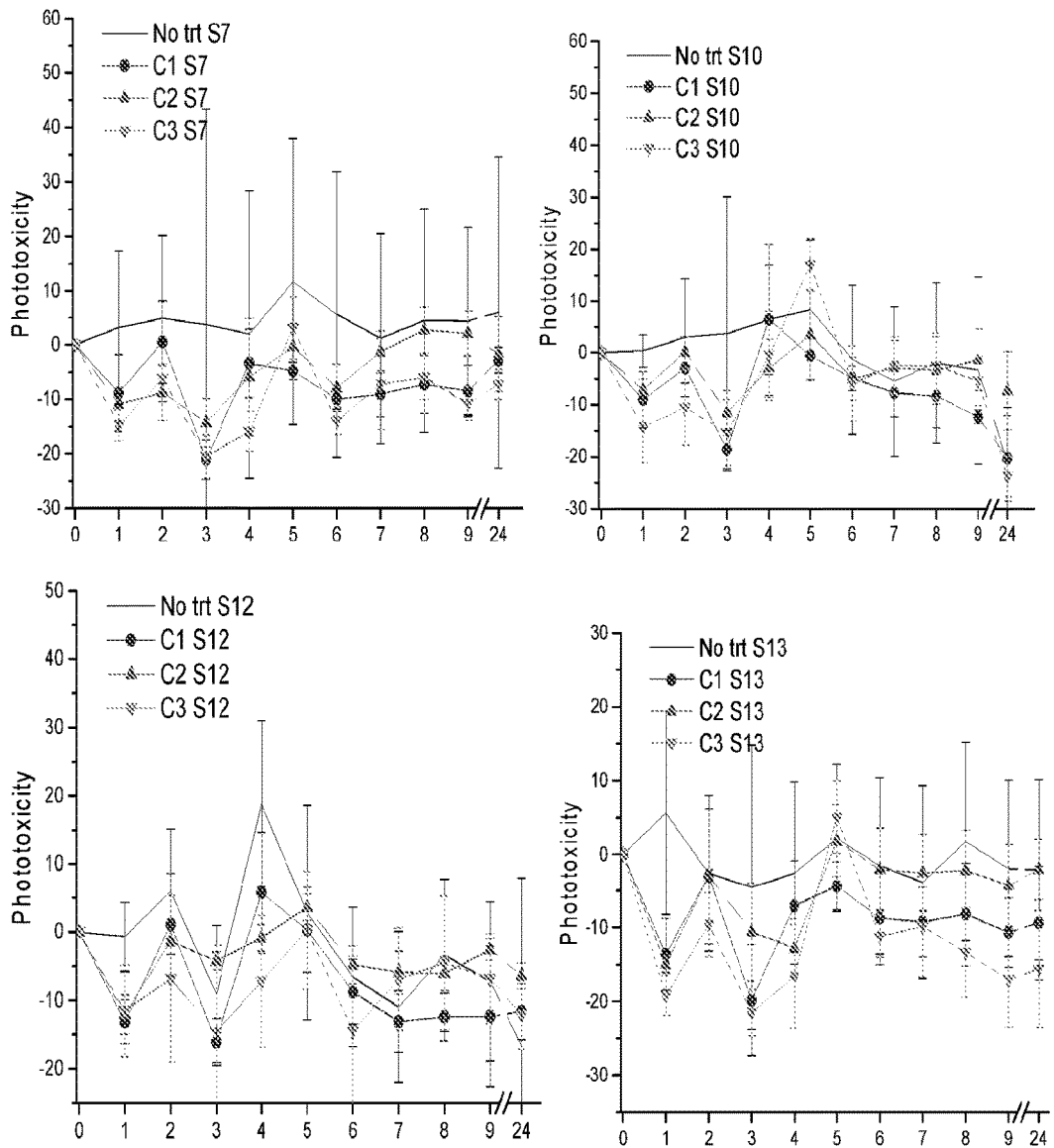
Figure 7A:
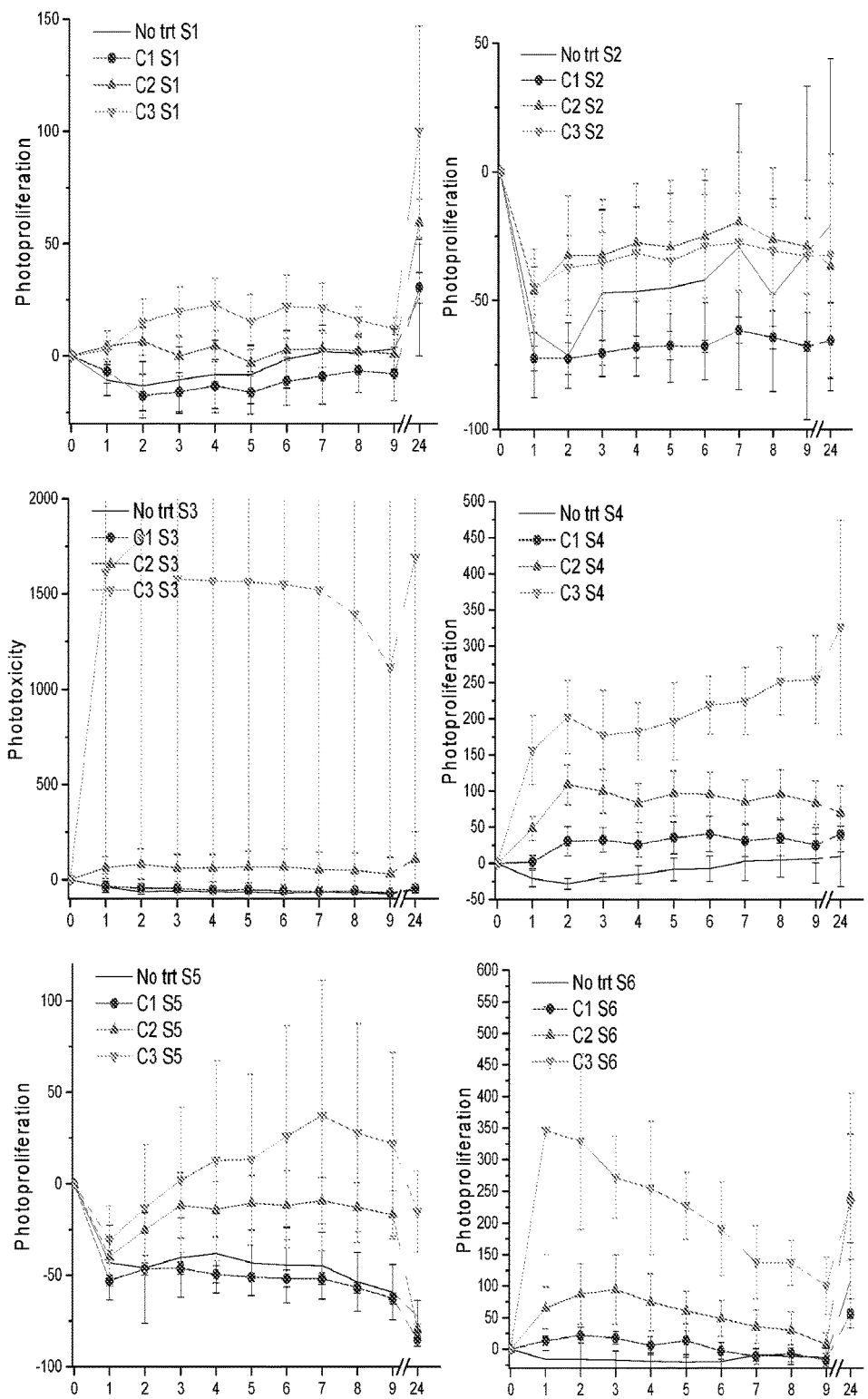
FIGS. 7A-7B comprise a series of graphs illustrating photoproliferation for CIS-1.9 particles in MDR clinical strains. C1 was 10 nM, C2 was 50 nM, and C3 was 100 nM. Data were normalized to t=0 and the average of 3 biological replicates, and error bars represent standard deviation. Ordinates represent hours (h).
Figure 7B:
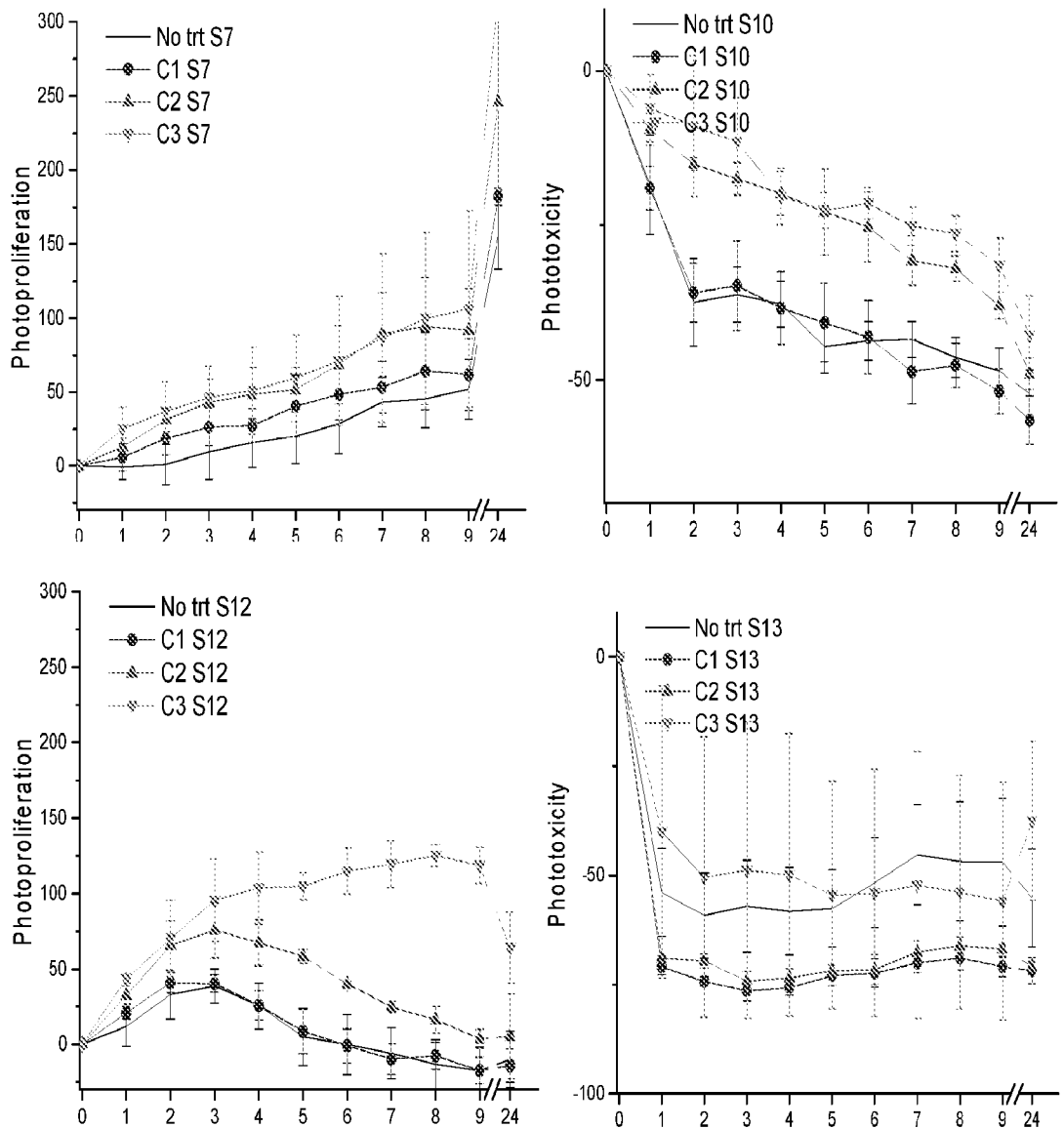
Figure 8A:
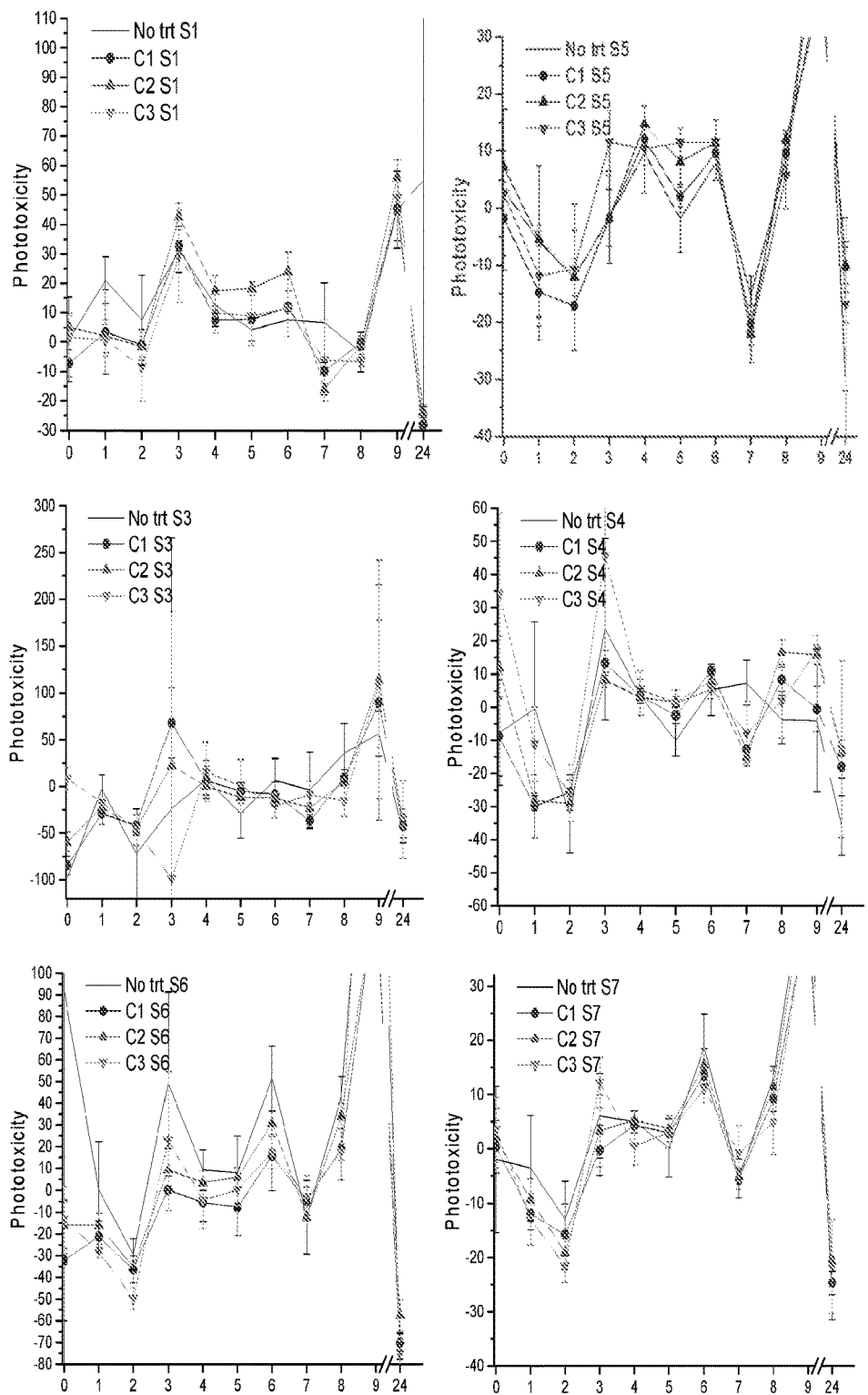
FIGS. 8A-8B comprise a series of graphs illustrating phototoxicity for $Ag_2S$-1.7 particles in MDR clinical strains. Concentrations were represented by dilution from stock of particles where C1 was 1:100 dilution, C2 was 1:1,000 dilution, and C3 was 1:10,000. Data were the average of 3 biological replicates, and error bars represent standard deviation. Ordinates represent hours (h).
Figure 8B:
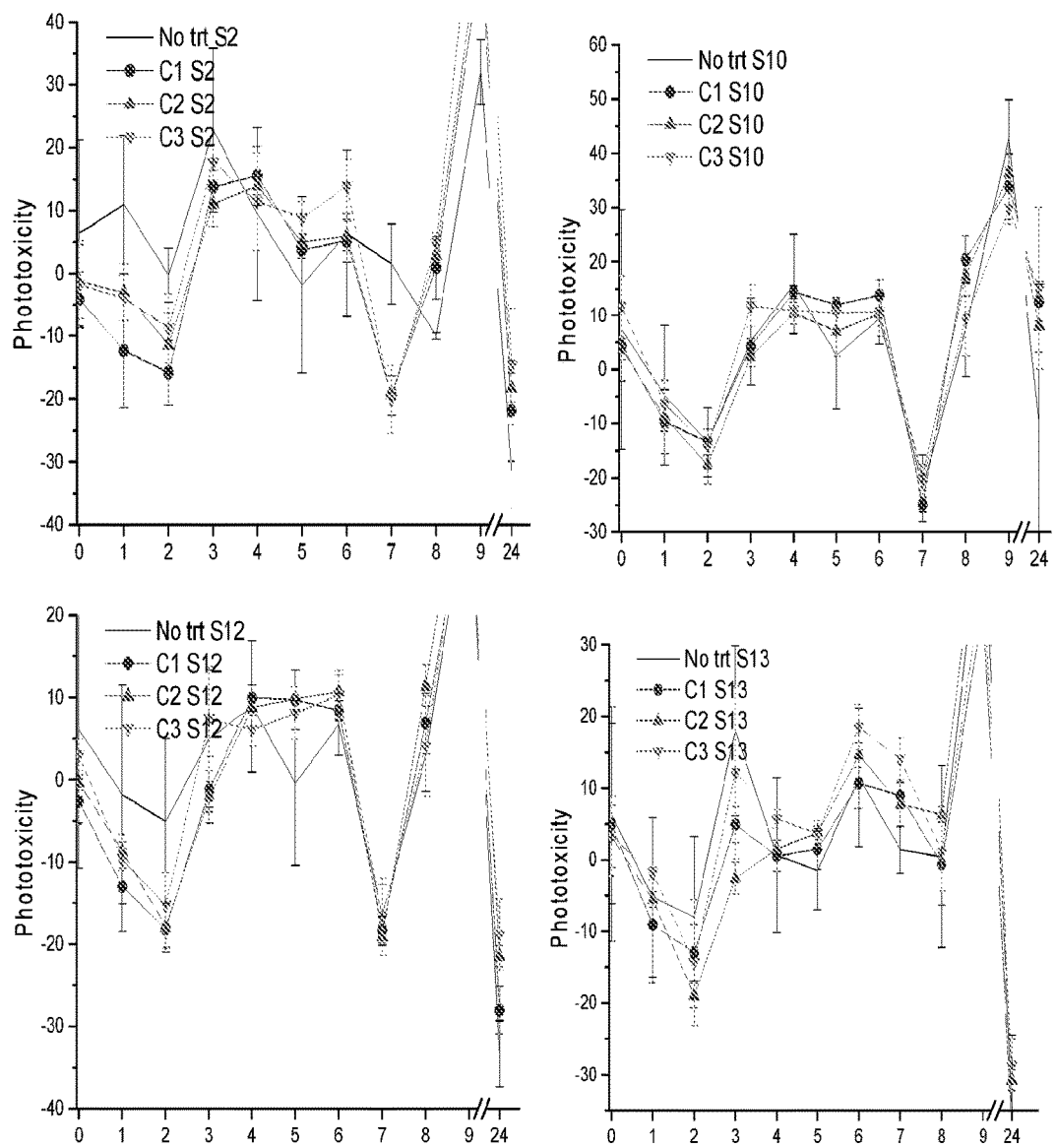
Figure 9A:
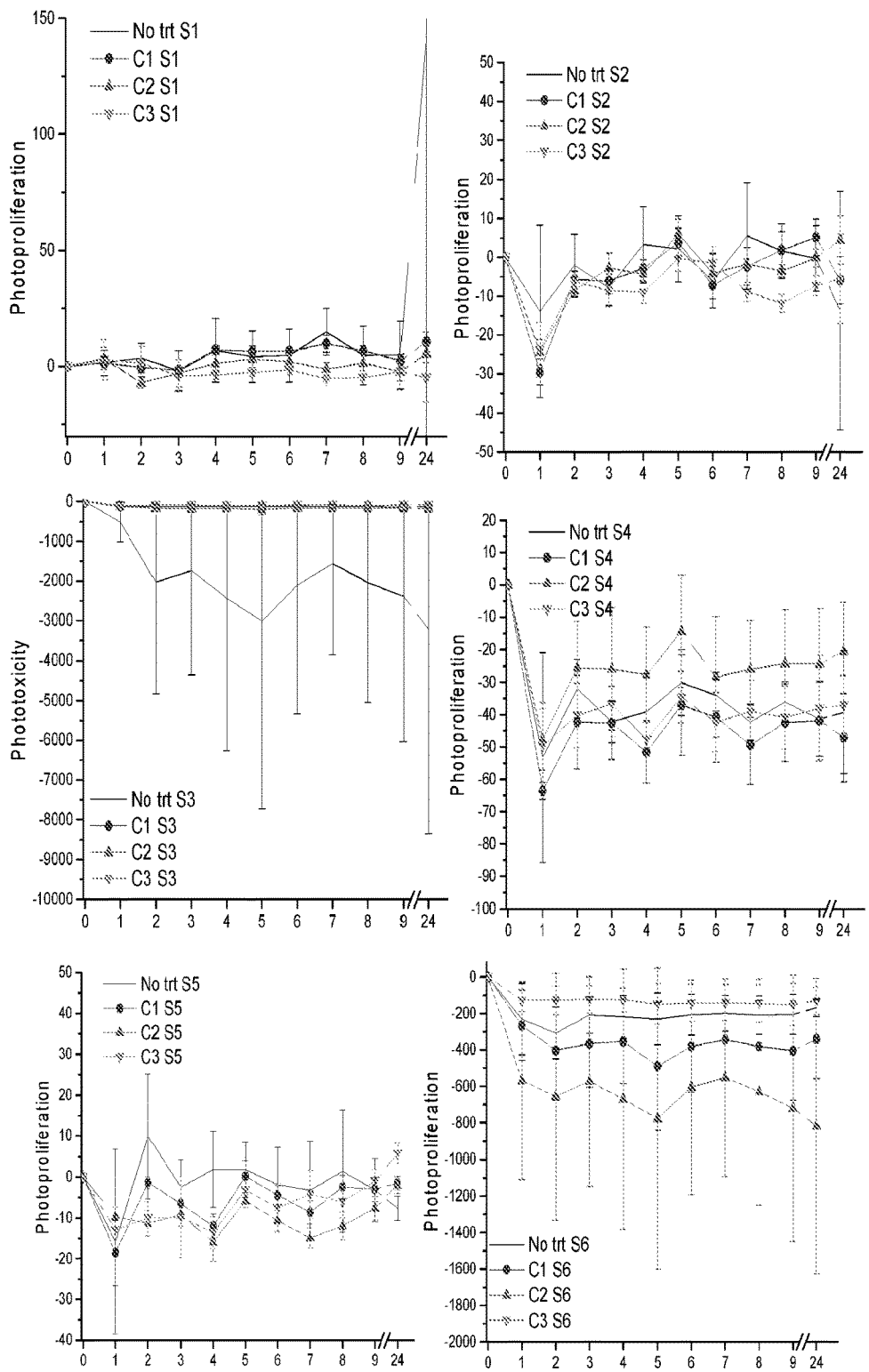
FIGS. 9A-9B comprise a series of graphs illustrating phototoxicity for $Cu_2S$-2.1 particles in MDR clinical strains. Concentrations were represented by dilution from stock of particles where C1 was 1:100 dilution, C2 was 1:1,000 dilution, and C3 was 1:10,000. Data were normalized to t=0 and the average of 3 biological replicates, and error bars represent standard deviation. Ordinates represent hours (h).
Figure 9B:
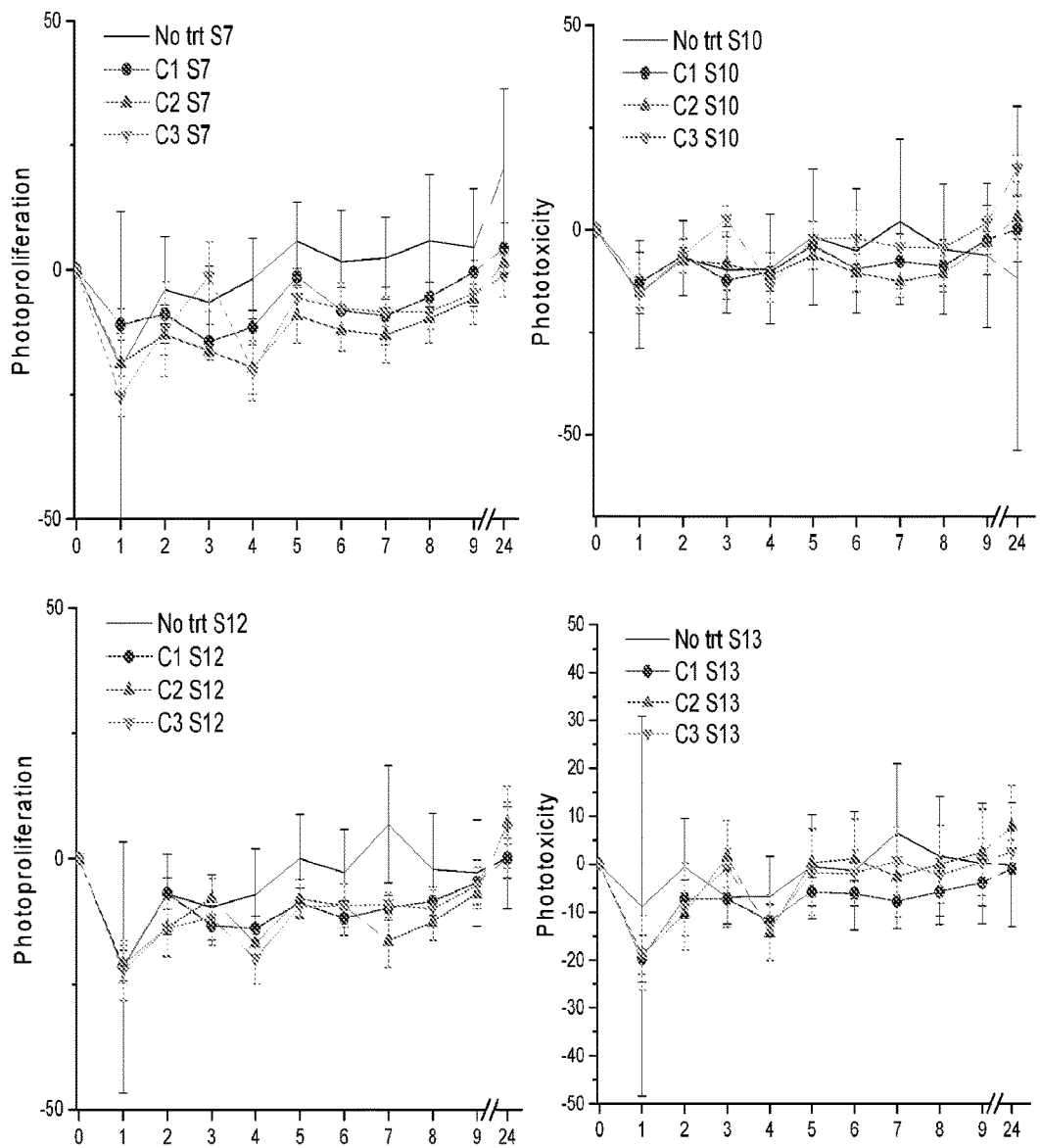
Figure 10A:
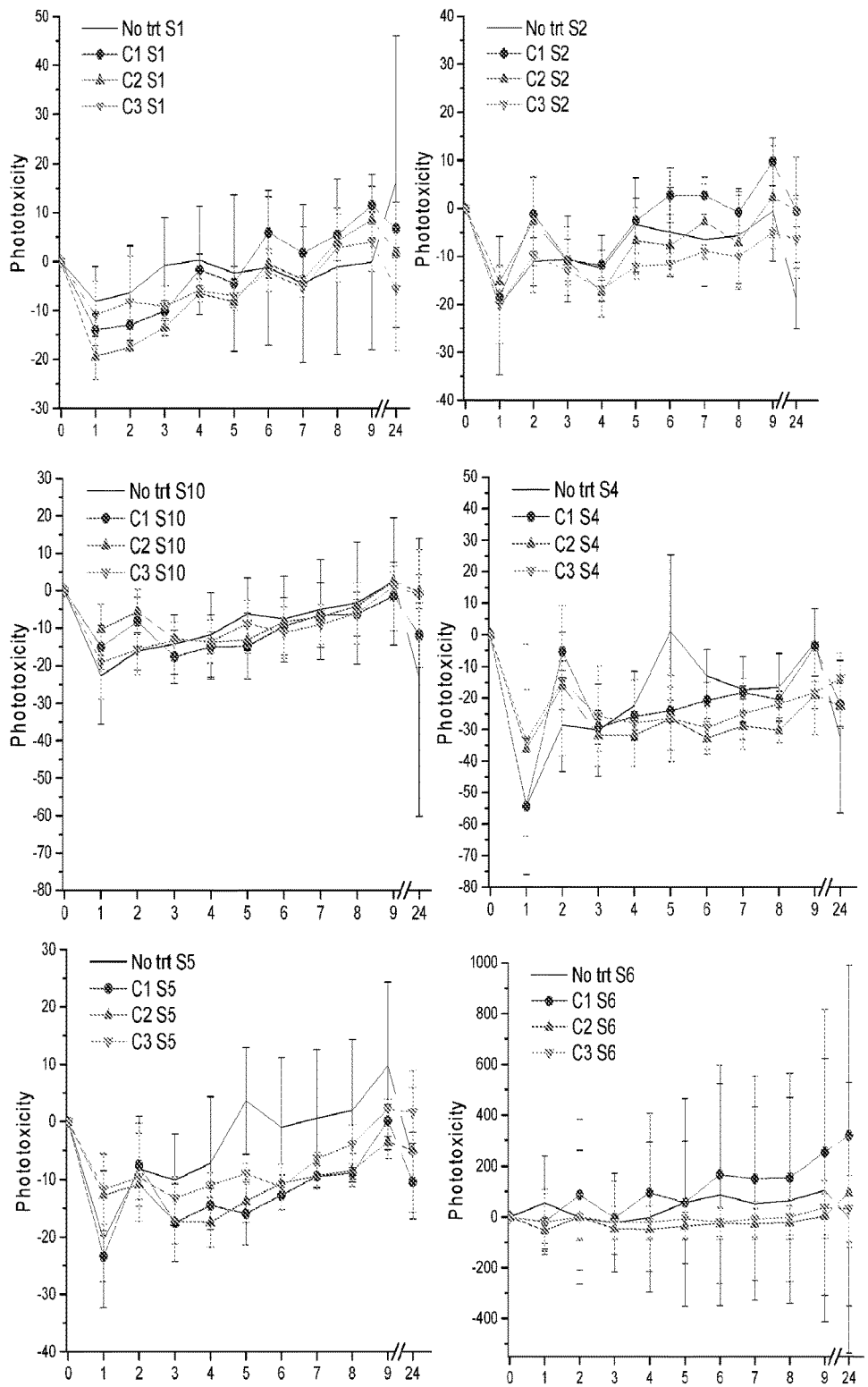
FIGS. 10A-10B comprise a series of graphs illustrating phototoxicity for FeS-2.0 particles in MDR clinical strains. Concentrations were represented by dilution from stock of particles where C1 was 1:100 dilution, C2 was 1:1,000 dilution, and C3 was 1:10,000. Data were normalized to t=0 and the average of 3 biological replicates, and error bars represent standard deviation. Ordinates represent hours (h).
Figure 10B:
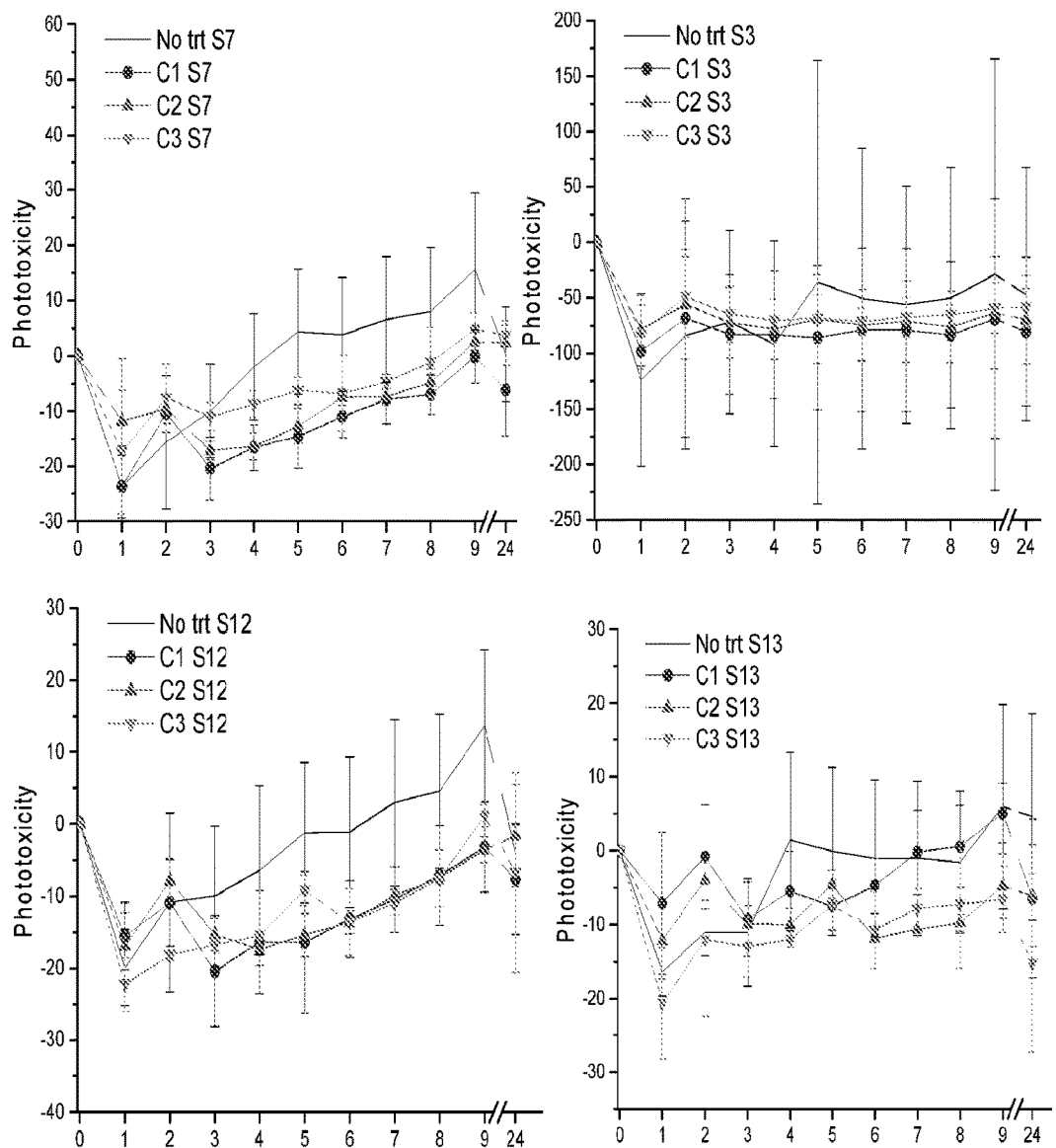

Example 4: Photoeffect of Quantum Dots on Multi-Drug-Resistant Clinical Strains of Bacteria After confirming the non-material dependent qualities of quantum dots and their photoeffects in a lab strain of *E. coli*, the particles were implemented with multi-drug resistant (MDR) clinical isolates (Table 1). CdTe-2.4 showed significant phototoxic effect for three MDR strains of *K. pneumoniae* (S1, S5, S7), two MDR strains of *E. coli* (S2, S12), methicillin resistant MDR *S. aureus* (S4), and MDR *S. typhimurium* (S10) (FIGS. 5A-5B). CdSe-2.4 was consistent with data in Dh5α and showed no photoeffect in clinical strains (FIGS. 6A-6B). CIS-1.9 showed photoproliferation in two MDR strains of *K. pneumoniae* (S1, S5), MDR *E. coli* (S12), MDR *P. aeruginosa* (S6), and MDR *A. baurnannil* (S13) (FIGS. 7A-7B). $Ag_2S$-1.7, $Cu_2S$-2.1, and FeS-2.0 shown no significant photoeffect (FIGS. 8A, 8B, 9A, 9B, 10A, 10B).

Example 5: Potential Antimicrobial Therapeutic Application and Selective Redox Tuned Cell Death In certain embodiments, the phototoxic response observed in CdTe-2.4 allows for its use as a therapeutic agent for combating localized, bacterial infections. In other embodiments, QDs kill or preclude the growth of bacteria while leaving the surrounding host tissue healthy and intact. The present study addresses in part whether selective cell death can be observed due to QDs being tuned to specific organism-dependent cellular redox environments.

To evaluate antimicrobial potential, co-culture experiments were performed with *E. coli* and HEK293 cells. HEK293 cultures were grown in tissue culture treated, 96-well plates for 24 hours to obtain 80% confluency, and then inoculated with *E. coli* and treated with quantum dots for 24 hours. To evaluate cell health, the HEK293 cells were fixed in 4% formaldehyde and dyed with the nuclear stain DAPI and actin stain Phalloidin Cruzfluor 488 conjugate to observe cell morphology. Prior to the co-culture, *E. coli* was transformed to maintain a plasmid constitutively expressing the mCherry fluorescent protein and was observed for cell density.

HEK293 cells, in absence of bacteria, did not exhibit a morphologically observable photoeffect in the presence of CdTe-2.4, CdSe-2.4, or CIS-1.9 (FIG. 18). The materials were also not inherently toxic to HEK293 at the QD concentrations studied. When co-cultured without QDs, there was comparable growth of *E. coli* and consistent cell morphology of HEK293 in light and dark. *E. coli* and HEK293 cells did not display a phototoxic effect in the presence of CdSe-2.4, as predicted by the monocultures. In contrast, CdTe-2.4 produced a phototoxic effect in *E. coli* and no observable photoeffect in HEK293 cells, as predicted by monocultures (FIG. 11). This study showed that in co-culture selective cell death by the survival of HEK293 cells and the eradication of *E. coli* cells illuminated in the presence of CdTe-2.4 was obtained.

Example 6: Exploration of Other Metal Sulfides

To examine the potential of other nanoparticles made from distinct metals, iron, silver, and copper sulfide were synthesized using ammonium sulfide (FIG. 12). Based on STS measurements of these particles, FeS possessed the nearest oxidation potential to the established required for phototoxicity with a slight overpotential. Both $Ag_2S$ and $Cu_2S$ did not align with any known photoeffect potential, and a corresponding lack of phototoxicity or photoproliferation was observed in all strains tested.

Example 7: Ligand Charge Effects

In one aspect, chemical instability of the QDs was evidenced by the change in emission spectra (FIG. 22). In another aspect, colloidal instability over time in relevant media was also observed. Without wishing to be limited by any theory, because the MPA ligands, which electrostatically stabilize the particles, remain unprotonated at pH 7.4 this instability can be due to the desorption of the ligands through the reprotonation or dimerization of the thiol termini. In the first case, it may be possible to increase colloidal stability by replacing the negatively-charged carboxylic acid ligands with an amine. This would create around the particle a layer of positive charge, which could screen incoming protons from being able to diffuse to the thiol group. CdTe with positive ligands (CdTe—CA) were obtained through ligand exchange of MPA coated dots. The initial stocks were filtered and re-dispersed in pH 6 medium containing excess cysteamine (CA) and allowed to react overnight.

The particles were initially well-dispersed, though the emission was attenuated (FIG. 23A). The degradation profile of these particles were quantified in the same manner as the MPA-coated analogues (FIG. 23B). Instead of the two-regime curve shown previously, the CA coated particles exhibited only blue-shifting emission and a rapid loss of emission intensity. After two hours of light exposure, the photoluminescence was below the detection limit of the instrument, and the population kept in dark were non-luminescent between four and five hours. This is reflected in the absorbance spectra, which showed a rapid loss of colloidal stability with the increasing contributions of scattering, and chemical instability through the loss of the primary excitionic feature. In certain embodiments, in biologically relevant media, positively charged ligands lead to lower stability overall than those coated with MPA.

From the observed growth curves the positively charged particles also exhibited much greater inherent toxicity than their negatively charged counterparts (FIGS. 23C-23D). Such an effect is also observed for other strains of bacteria and some mammalian cells. Without wishing to be limited by any theory, the positively charged CdTe-2.4 can more easily bind to the negatively charged cell membrane and thus be incorporated within the cells at a higher concentration. Based on ICP analysis of exposed cultures, the positive ligands are associated with the cells in a significantly higher concentration than the nominal cores (FIG. 23E). Thus, in certain embodiments, their poor stability and increased inherent toxicity preclude such particles from being used within the present invention.

Example 8: ZnS Core Shells

One method of potentially increasing the chemical stability of the CdTe quantum dots, while decreasing their inherent toxicity, would be to coat them with a thin shell of a more biologically compatible material. In certain embodiments, such construct is a type-I heterostructure consisting of an emissive CdX core enveloped in a thin shell of ZnS, which protects the emission and decreases the overall toxicity. Without wishing to be limited by any theory, for therapeutic applications, the increased stability with thicker shells is weighed against the increasing tunneling barrier for moving photogenerated charges from the core material to the intended targets. In certain embodiments, there is the potential effect of different binding affinities between the core and shell metals, which could possibly change the ability of the particles to efficiently interact with the necessary species in the medium. Thus, ZnS shells with sub-monolayer thicknesses were investigated.

CdTe particles were filtered to remove unreacted starting materials and diluted to 2 µM in pH 11 water. Stock solutions containing zinc nitrate and thiourea (a sulfur source) were made and mixed in a 1:1 ratio with the quantum dot stock, then allowed to react at 98° C. for 1 h. The deposition of the shell material was identified optically by changes in the absorbance features and by red-shifting emission with greater coverage (FIG. 24A). In certain non-limiting embodiments, addition of the zinc sulfide changes the electronic structure of the constituent particles, without necessarily forming a true type-I junction. In other non-limiting embodiments, zinc preferentially adds to the tellurium rich facets, and sulfur to the cadmium. Based on the bulk potentials, ZnTe's valence band may fall within the nominal bandgap of CdTe as does CdS's conduction band (FIG. 24B). In certain non-limiting embodiments, the first monolayers can alter the electronic structure of the core, either due to defect formation in the low coverage regime, or due to the creation of a closely aligned pseudo type-II junction approaching single monolayer deposition. Due to the high surface area to volume ratios in sub-5 nm diameter particles, a plurality of atoms are involved with the core-shell interface, thus having a significant effect on the hybrid electronic structure when a coating material is chosen whose individual interactions with the core elements results in similar band positions.

Quantifying the elemental composition of the ZnS coated core shells allows the calculation of the total surface coverage of the CdTe cores. A maximum coverage of about 25% Zn was obtained when the shell precursor solutions contained zinc and sulfur at a concentration equivalent to two mono-layers equivalent (MLE) concentration relative to the cores. Using higher concentrations of ZnS resulted in the nucleation of those particles directly, instead of thicker shell growth. The shell formation does not have an appreciable impact on the fluorescence quantum yield in relation to the cores alone (FIG. 24A), indicating that any benefit due to increased passivation is offset by the change in electronic structure at low loadings.

To test the stability of the core-shell structures relative to the cores an experiment was performed to track the degradation over time, and exhibited different degradation profiles (FIG. 24C). There was an initial regime of slowly blue-shifting emission, which may represent the oxidation of the shell materials, where the addition of oxygen removes some of the trap-like states and moves the emission slightly closer towards the nominal cores. However, this effect was temporary, and once the shell was fully oxidized, similar red-shifting behavior as seen in the cores begins to take place, followed by a rapid blue-shift and collapse of the emission intensity. These measurements support the assertion that the core shell particles degrade significantly slower than the naked cores, lasting about twice as long, and that the persistence of the emission implies that they are able to continue generating redox species as well.

To quantify the core shells' effects on bacterial inhibition they were directly compared to cores using the culture procedures described elsewhere herein (FIGS. 25A-25B). The photoeffect was maintained with the core shells, though there was a certain lag-time before they become effective, as evidenced by the OD growth curves. There was no significant change in particle uptake relative to the cores, indicating that when in the same size regime the primary motivator for particle association is the capping ligand.

Example 9: Cd Overcoat

In certain embodiments, the observed oxidation occurs due to the replacement of tellurium. In other embodiments, a strategy for increasing stability is to overcoat the tellurium rich facets with additional cadmium directly. The only effect this would have on the electronic structure of the particles would be a slight decrease in bandgap due to the larger diameter, which is reflected in the consistent features in the optical spectra (FIG. 26A). These particles were synthesized in a similar manner as the ZnS core shells, only reacting for 15 min. Elemental analysis of these particles indicates there was a 30% increase in cadmium content compared to the cores, which translates to 0.6 MLE coverage, showing complete passivation of the tellurium facets. The increased passivation is reflected in the luminescence quantum yield of the overcoated particles, which is over twice that of the untreated cores.

In terms of stability, the cadmium overcoated samples consistently outperformed both the cores and ZnS core shells (FIG. 26B). Unlike those other samples, the overcoated particles were still luminescent at 24 h of light illumination, and underwent much slower rates of degradation during the first nine hours than the ZnS. The degradation curve also consisted of a single monotonic phase of slow blue shifting, which appears to be characteristic of this type of treated sample. In certain non-limiting embodiments, as there are no exposed tellurium facets with which to readily exchange anions, degradation consists of only the slow diffusion of oxygen through the cadmium layer.

When tested in vitro, the overcoat quantum dots retained a similar lag phase as the ZnS core shells, but had overall higher phototoxicity and an inherent toxicity which did not as strongly depend on particle concentration (FIGS. 26C-26D). As the uptake of these particles did not significantly different than the untreated cores (FIG. 26E), their enhanced stability and consistent efficacy indicate that this passivation strategy improves the overall properties of therapeutic nanomaterials.

Example 10: Photoexcited Quantum Dot Functions in Combination with Antibiotics Against Multi Drug Resistant Gram-Negative Bacteria Methods Bacterial Cell Culture:

Clinical isolates were growth in liquid cation adjusted Mueller Hinton broth (CAMHB) (DIFCO) or on solid CAMHB and 1.5% agar. Clinical strains were stored in 10% glycerol at −80° C. for long term storage. Replicates were started from individual, single colonies off of solid plates and grown for 16 h at 37° C. with 225 rpm shaking before beginning experiments. Optical density was measured with a Tecan GENios at 562 nm with a bandwidth of 35 nm.

$IC_{50}$ Measurement:

Overnight cultures of clinical isolates were diluted to a 0.5 McFarland standard in CAMHB with respective test concentration of antibiotic. Cultures were grown for 24 h at 37° C. with 225 rpm shaking. After 24 h of growth, Resazurin sodium salt (Sigma Aldrich) solution was added and the reaction was monitored for fluorescence measuring every 5 min for 4 h at 37° C. with 225 rpm shaking using 485/610 nm filters. The slope of Resazurin fluorescence was used a quantitative measure of cell metabolism. The $IC_{50}$ was determined as the concentration of antibiotic which caused a 50% reduction in slope compared to the same biological replicate in no treatment.

Combinatorial Experiments:

Five antibiotic concentrations were selected for each strain, so that the levels tested would be below the $IC_{50}$, near the CLSI or defined breakpoint, and near the $IC_{50}$. Concentrations of CdTe-2.4 were held constant for all strains at 12.5 nM, 25 nM, and 50 nM. Using these metrics, three biological replicates were tested from each strain with 15 test conditions as well as monotherapy controls and a no treatment condition. Clinical strains were diluted 1:100 from overnight into test condition and grown at 37° C. with 225 rpm. Optical density was measured every 30 min for the first 3 h and every hour subsequently until 8 h. After 8 h of growth, Resazurin sodium salt solution was added and the reaction was monitored for fluorescence measuring every 5 min for 4 h at 37° C. with 225 rpm shaking using 485/610 nm filters. The slope of Resazurin fluorescence was used a quantitative measure of cell metabolism.

Discussion

Multi-drug resistant (MDR) bacterial infections threaten the future of our healthcare system due to pan-drug resistant bacteria. There is a need for antimicrobial agents that are efficacious, either alone or in combination with current antibiotics, to treat MDR bacteria and mitigate the antibiotic crisis. As demonstrated herein, compositions of the invention can be used in combination with current antibiotics to inhibit MDR bacteria.

Cadmium telluride quantum dots with a band gap of 2.4 eV (CdTe-2.4) were used in combination with other antibiotics to inhibit gram-negative clinical isolates of MDR bacteria (FIGS. 22A-22B). Four gram-negative clinical strains were used to investigate the ability of CdTe-2.4 to function as a therapeutic in combination with current antibiotics: a MDR strain of *Escherichia coli*, a MDR strain of *Salmonella typhimurium*, an extended spectrum β-lactamase (ESBL) producing strain of *Klebsiella pneumoniae*, and a carbapenem resistant strain of *E. coli*. The concentration of antibiotic that inhibits 50% of the cultures growth ($IC_{50}$) was measured for the four strains against five antibiotics chosen for their different mechanisms of action (FIG. 22B): a cephalosporin antibiotic (ceftriaxone), a fluoroquinone (ciprofloxacin), and three protein synthesis inhibitors (clindamycin and chloramphenicol, and streptomycin).

MDR *S. typhimurium* and MDR *E. coli* were sensitive to chloramphenicol and MDR *S. typhimurium* was also sensitive to ciprofloxacin (FIG. 22B). When ESBL *K. pneumoniae* was treated with 25 nM CdTe-2.4 and 8 µg/mL streptomycin, significant inhibition of growth was observed, in comparison with no treatment and the corresponding monotherapies (FIG. 22C). Addition of CdTe-2.4 allowed significant inhibition of growth of ESBL *K. pneumoniae* to a breakpoint amount of streptomycin that was previously ineffective.

A similar growth inhibition was observed in MDR *S. typhimurium* (FIG. 22D). The degree of growth inhibition was dependent on the concentration of CdTe-2.4 and the concentration of streptomycin (FIG. 22D).

Figure 29:
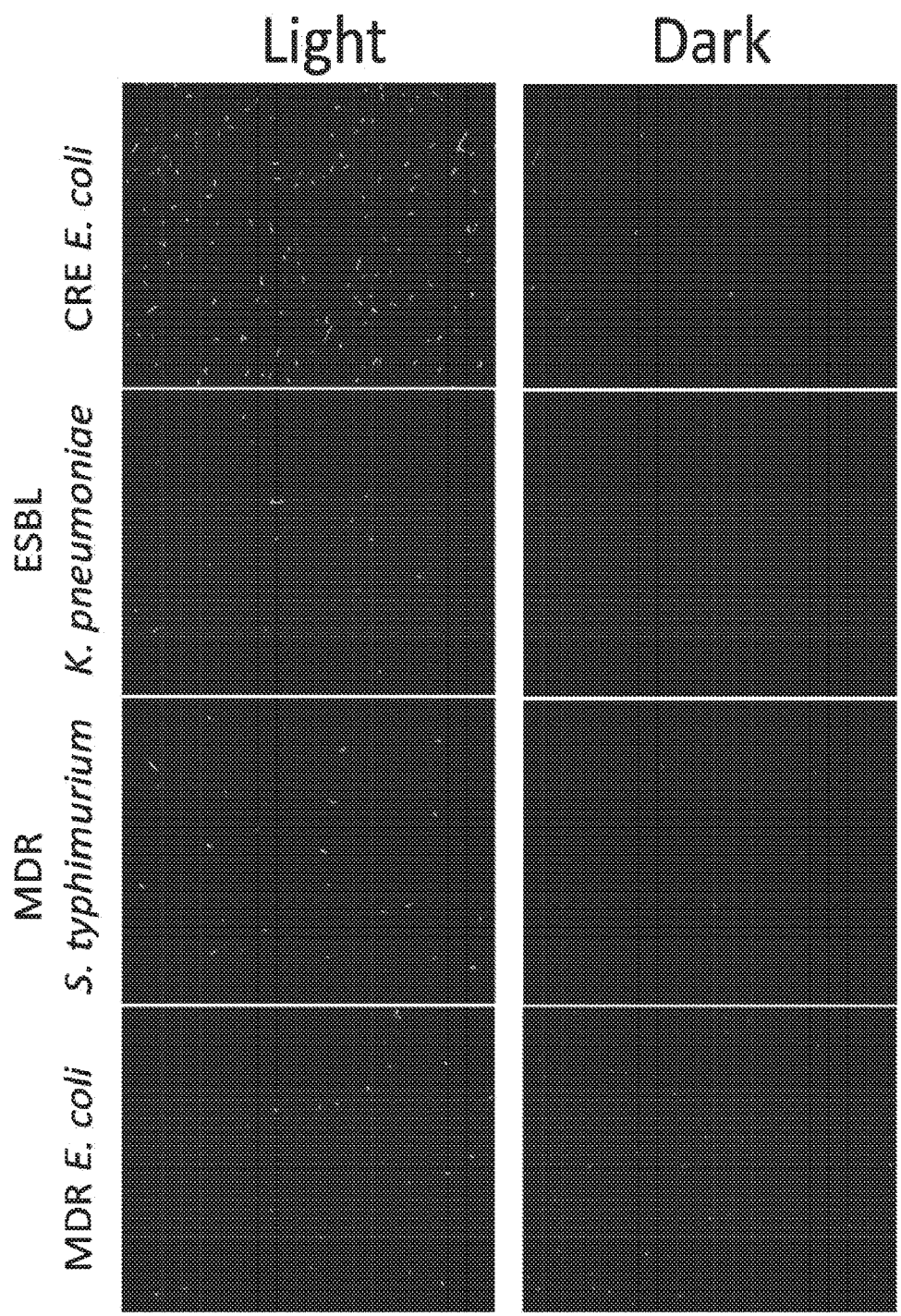

The dual treatment against the MDR gram-negative bacteria significantly reduced the number of viable cells in the culture in only 4 h of treatment (FIGS. 28A-28B). Similar to MG1655, CdTe-2.4 generated reactive oxygen species upon illumination with light in the multi-drug resistant strains, confirming the mechanism of action (FIG. 29).

The present studies have shown that multi-drug resistant bacteria can be successfully inhibited using a combination of antibiotic and tuned quantum dot or nanoparticle.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising at least one semiconductor-containing nanoparticle,
    wherein the at least one nanoparticle has a band edge redox potential such that, under conditions whereby the at least one nanoparticle penetrates a first cell, irradiation of the at least one nanoparticle with radiation ranging from about 400 nm to about 1,000 nm within the first cell promotes growth, kills, or prevents or hampers growth, of the first cell,
    wherein the at least one nanoparticle has no measurable effect on the growth, metabolism, or survival of the first cell in the absence of radiation ranging from about 400 nm to about 1,000 nm.

2. The composition of claim 1, wherein the at least one nanoparticle comprises a quantum dot (QD).

3. The composition of claim 1, wherein the at least one nanoparticle comprises CdTe, and wherein the at least one nanoparticle is at least partially coated with at least one selected from the group consisting of ZnS and CdS.

4. The composition of claim 1, which further comprises the first cell.

5. The composition of claim 1, wherein the first cell is a bacterium.

6. The composition of claim 5, wherein the bacterium comprises at least one selected from the group consisting of *K. pneumonia, E. coli, S. aureus, P. aeruginosa, A. baumannii* and *S. typhimurium*.

7. The composition of claim 5, wherein the first cell comprises a gram-negative bacterium.

8. The composition of claim 7, which further comprises at least one gram-negative antibacterial agent.

9. The composition of claim 8, wherein the concentration or amount of the antibacterial agent in the composition that is required to kill, or prevent or hamper the growth of, gram-negative bacteria is lower than the concentration or amount of the antibacterial agent that is required to kill, or prevent or hamper the growth of, gram-negative bacteria when the antibacterial agent is used in the absence of the at least one nanoparticle.

10. The composition of claim 4, further comprising a second cell, wherein irradiation of the at least one nanoparticle has no measurable effect on the growth, metabolism, or survival of the second cell.

11. The composition of claim 2, wherein (i) irradiation of the at least one nanoparticle within the first cell promotes growth of the first cell, and wherein the QD comprises $CuInS_2$, or (ii) irradiation of the at least one nanoparticle within the first cell kills, or prevents or hampers growth of, the first cell, and wherein the QD comprises CdTe.

12. The composition of claim 2, wherein:
    (i) irradiation of the at least one nanoparticle within the first cell promotes growth of the first cell, and wherein the band edge of the conduction band state (reduction potential) of the QD is about +0.2 V and the band edge of the valence band state (oxidation potential) of the QD is about −1.8 V, as referenced to NHE (standard hydrogen electrode), or
    (ii) irradiation of the at least one nanoparticle within the first cell promotes death, or prevents or hampers growth, of the first cell, and wherein the band edge of the conduction band state (reduction potential) of the QD is about +0.35 V and the band edge of the valence band state (oxidation potential) of the QD is about −2.1 V, as referenced to NHE (standard hydrogen electrode).

13. A composition comprising at least one semiconductor-containing nanoparticle,
    wherein the at least one nanoparticle has a band edge redox potential such that, under conditions whereby the at least one nanoparticle penetrates a first cell, irradiation of the at least one nanoparticle with radiation ranging from about 400 nm to about 1,000 nm within the first cell promotes growth, kills, or prevents or hampers growth, of the first cell, wherein the at least one nanoparticle has no measurable effect on the growth, metabolism, or survival of the first cell in the absence of radiation ranging from about 400 nm to about 1,000 nm, wherein:
(i) irradiation of the at least one nanoparticle within the first cell promotes growth of the first cell, and wherein the band edge of the conduction band state (reduction potential) of the QD is about +0.2 V and the band edge of the valence band state (oxidation potential) of the QD is about −1.8 V, as referenced to NHE (standard hydrogen electrode), or
(ii) irradiation of the at least one nanoparticle within the first cell promotes death, or prevents or hampers growth, of the first cell, and wherein the band edge of the conduction band state (reduction potential) of the QD is about +0.35 V and the band edge of the valence band state (oxidation potential) of the QD is about −2.1 V, as referenced to NHE (standard hydrogen electrode).

14. The composition of claim 13, wherein (i) irradiation of the at least one nanoparticle within the first cell promotes growth of the first cell, and wherein the QD comprises $CuInS_2$, or (ii) irradiation of the at least one nanoparticle within the first cell kills, or prevents or hampers growth of, the first cell, and wherein the QD comprises CdTe.

* * * * *